US010539539B2

(12) United States Patent
Garlepp et al.

(10) Patent No.: US 10,539,539 B2
(45) Date of Patent: Jan. 21, 2020

(54) OPERATION OF AN ULTRASONIC SENSOR

(71) Applicant: InvenSense, Inc., San Jose, CA (US)

(72) Inventors: Bruno W. Garlepp, Sunnyvale, CA (US); Michael H. Perrott, Nashua, NH (US); James Christian Salvia, Belmont, CA (US)

(73) Assignee: InvenSense, Inc., San Jose, CA (US)

(*) Notice: Subject to any disclaimer, the term of this patent is extended or adjusted under 35 U.S.C. 154(b) by 136 days.

(21) Appl. No.: 15/589,921

(22) Filed: May 8, 2017

(65) Prior Publication Data
US 2017/0328870 A1 Nov. 16, 2017

Related U.S. Application Data

(60) Provisional application No. 62/334,399, filed on May 10, 2016.

(51) Int. Cl.
G01N 29/34 (2006.01)
G11C 19/28 (2006.01)
(Continued)

(52) U.S. Cl.
CPC ........... *G01N 29/34* (2013.01); *B06B 1/0629* (2013.01); *G10K 11/346* (2013.01);
(Continued)

(58) Field of Classification Search
CPC ...... G01N 29/04; G01N 29/262; G01N 29/34; B06B 1/0629; B06B 1/0666;
(Continued)

(56) References Cited

U.S. PATENT DOCUMENTS 5,575,286 A 11/1996 Weng et al.
5,684,243 A 11/1997 Gururaja et al.
(Continued)

FOREIGN PATENT DOCUMENTS

EP 1214909 A1 6/2002
EP 2884301 A1 6/2015
(Continued)

OTHER PUBLICATIONS

ISA/EP, International Search Report and Written Opinion for International Application No. PCT/US2017/031120, 12 pages, dated Aug. 29, 2017 (dated Aug. 29, 2017).
(Continued)

Primary Examiner — Helen C Kwok

(57) ABSTRACT

In a method of using an ultrasonic sensor comprising a two-dimensional array of ultrasonic transducers, a plurality of ultrasonic signals are transmitted according to a beamforming pattern at a position of the two-dimensional array. The beamforming pattern focuses the plurality of ultrasonic signals to location above the two-dimensional array, wherein the beamforming pattern identifies ultrasonic transducers of the two-dimensional array that are activated during transmission of the ultrasonic signals, and wherein at least some ultrasonic transducers of the beamforming pattern are phase delayed with respect to other ultrasonic transducers of the beamforming pattern. At least one reflected ultrasonic signal is received at the position according to a receive pattern, wherein the receive pattern identifies at least one ultrasonic transducers of the two-dimensional array that is activated during the receiving. The transmitting and the receiving are repeated at a plurality of positions of the two-dimensional array.

20 Claims, 37 Drawing Sheets

(51) Int. Cl.
    *G11C 19/38*         (2006.01)
    *B06B 1/06*          (2006.01)
    *G10K 11/34*        (2006.01)
    *H01L 41/047*       (2006.01)
    *H01L 41/113*       (2006.01)
    *H03K 17/96*        (2006.01)

(52) U.S. Cl.
    CPC ............ *G11C 19/287* (2013.01); *G11C 19/38* (2013.01); *H01L 41/047* (2013.01); *H01L 41/1132* (2013.01); *H03K 17/9643* (2013.01); *G01N 2291/106* (2013.01)

(58) Field of Classification Search
    CPC ... B06B 1/0622; B06B 1/0207; G10K 11/346; G10K 11/345; G10K 11/34; H01L 41/047; H01L 41/1132
    See application file for complete search history.

(56) References Cited

U.S. PATENT DOCUMENTS

| | | | |
|---|---|---|---|
| 5,808,967 A | 9/1998 | Yu et al. | |
| 5,867,302 A | 2/1999 | Fleming | |
| 6,071,239 A * | 6/2000 | Cribbs | A61N 7/00 600/439 |
| 6,104,673 A | 8/2000 | Cole et al. | |
| 6,289,112 B1 | 9/2001 | Jain et al. | |
| 6,350,652 B1 | 2/2002 | Libera et al. | |
| 6,428,477 B1 * | 8/2002 | Mason | A61B 8/4483 600/437 |
| 6,500,120 B1 | 12/2002 | Anthony | |
| 6,676,602 B1 | 1/2004 | Barnes et al. | |
| 6,736,779 B1 * | 5/2004 | Sano | A61B 8/00 600/447 |
| 7,067,962 B2 | 6/2006 | Scott | |
| 7,109,642 B2 | 9/2006 | Scott | |
| 7,243,547 B2 | 7/2007 | Cobianu et al. | |
| 7,400,750 B2 | 7/2008 | Nam | |
| 7,459,836 B2 | 12/2008 | Scott | |
| 7,471,034 B2 | 12/2008 | Schlote-Holubek et al. | |
| 7,489,066 B2 | 2/2009 | Scott et al. | |
| 7,739,912 B2 | 6/2010 | Schneider et al. | |
| 8,018,010 B2 | 9/2011 | Tigli et al. | |
| 8,139,827 B2 | 3/2012 | Schneider et al. | |
| 8,311,514 B2 | 11/2012 | Bandyopadhyay et al. | |
| 8,335,356 B2 | 12/2012 | Schmitt | |
| 8,433,110 B2 | 4/2013 | Kropp et al. | |
| 8,508,103 B2 | 8/2013 | Schmitt et al. | |
| 8,515,135 B2 | 8/2013 | Clarke et al. | |
| 8,666,126 B2 | 3/2014 | Lee et al. | |
| 8,703,040 B2 | 4/2014 | Liufu et al. | |
| 8,723,399 B2 | 5/2014 | Sammoura et al. | |
| 8,805,031 B2 | 8/2014 | Schmitt | |
| 9,056,082 B2 | 6/2015 | Liautaud et al. | |
| 9,070,861 B2 | 6/2015 | Bibl et al. | |
| 9,224,030 B2 | 12/2015 | Du et al. | |
| 9,245,165 B2 | 1/2016 | Slaby et al. | |
| 9,424,456 B1 | 8/2016 | Kamath Koteshwara et al. | |
| 9,572,549 B2 | 2/2017 | Belevich et al. | |
| 9,582,102 B2 | 2/2017 | Setlak | |
| 9,607,203 B1 | 3/2017 | Yazdandoost et al. | |
| 9,607,206 B2 | 3/2017 | Schmitt et al. | |
| 9,613,246 B1 | 4/2017 | Gozzini et al. | |
| 9,665,763 B2 | 5/2017 | Du et al. | |
| 9,747,488 B2 | 8/2017 | Yazdandoost et al. | |
| 9,785,819 B1 | 10/2017 | Oreifej | |
| 9,815,087 B2 | 11/2017 | Ganti et al. | |
| 9,817,108 B2 | 11/2017 | Kuo et al. | |
| 9,818,020 B2 | 11/2017 | Schuckers et al. | |
| 9,881,195 B2 | 1/2018 | Lee et al. | |
| 9,881,198 B2 | 1/2018 | Lee et al. | |
| 9,898,640 B2 | 2/2018 | Ghavanini | |
| 9,904,836 B2 | 2/2018 | Yeke Yazdandoost et al. | |
| 9,909,225 B2 | 3/2018 | Lee et al. | |
| 9,922,235 B2 | 3/2018 | Cho et al. | |
| 9,934,371 B2 | 4/2018 | Hong et al. | |
| 9,939,972 B2 | 4/2018 | Shepelev et al. | |
| 9,953,205 B1 | 4/2018 | Rasmussen et al. | |
| 9,959,444 B2 | 5/2018 | Young et al. | |
| 9,967,100 B2 | 5/2018 | Hong et al. | |
| 9,983,656 B2 | 5/2018 | Merrell et al. | |
| 9,984,271 B1 | 5/2018 | King et al. | |
| 10,275,638 B1 | 4/2019 | Yousefpor et al. | |
| 2002/0135273 A1 | 9/2002 | Mauchamp et al. | |
| 2003/0013955 A1 | 1/2003 | Poland | |
| 2004/0085858 A1 | 5/2004 | Khuri-Yakub et al. | |
| 2004/0122316 A1 | 6/2004 | Satoh et al. | |
| 2004/0174773 A1 * | 9/2004 | Thomenius | B06B 1/0292 367/174 |
| 2005/0057284 A1 * | 3/2005 | Wodnicki | A61B 8/13 327/100 |
| 2005/0110071 A1 | 5/2005 | Ema et al. | |
| 2005/0146240 A1 | 7/2005 | Smith et al. | |
| 2005/0148132 A1 | 7/2005 | Wodnicki et al. | |
| 2005/0162040 A1 | 7/2005 | Robert | |
| 2006/0052697 A1 | 3/2006 | Hossack et al. | |
| 2006/0079777 A1 | 4/2006 | Karasawa | |
| 2007/0046396 A1 | 3/2007 | Huang | |
| 2007/0073135 A1 * | 3/2007 | Lee | A61B 8/08 600/407 |
| 2007/0202252 A1 | 8/2007 | Sasaki | |
| 2007/0215964 A1 | 9/2007 | Khuri-Yakub et al. | |
| 2007/0230754 A1 | 10/2007 | Jain et al. | |
| 2008/0125660 A1 | 5/2008 | Yao et al. | |
| 2008/0150032 A1 | 6/2008 | Tanaka | |
| 2008/0194053 A1 | 8/2008 | Huang | |
| 2009/0005684 A1 | 1/2009 | Kristoffersen et al. | |
| 2009/0182237 A1 | 7/2009 | Angelsen et al. | |
| 2009/0274343 A1 | 11/2009 | Clarke | |
| 2009/0303838 A1 | 12/2009 | Svet | |
| 2010/0030076 A1 * | 2/2010 | Vortman | A61N 7/02 600/439 |
| 2010/0168583 A1 | 7/2010 | Dausch et al. | |
| 2010/0195851 A1 | 8/2010 | Buccafusca | |
| 2010/0201222 A1 | 8/2010 | Adachi et al. | |
| 2010/0202254 A1 | 8/2010 | Roest et al. | |
| 2010/0239751 A1 | 9/2010 | Regniere | |
| 2010/0251824 A1 | 10/2010 | Schneider et al. | |
| 2010/0256498 A1 | 10/2010 | Tanaka | |
| 2010/0278008 A1 | 11/2010 | Ammar | |
| 2011/0285244 A1 | 11/2011 | Lewis et al. | |
| 2011/0291207 A1 | 12/2011 | Martin et al. | |
| 2012/0016604 A1 | 1/2012 | Irving et al. | |
| 2012/0092026 A1 | 4/2012 | Liautaud et al. | |
| 2012/0095347 A1 * | 4/2012 | Adam | A61B 8/12 600/459 |
| 2012/0147698 A1 | 6/2012 | Wong et al. | |
| 2012/0232396 A1 | 9/2012 | Tanabe | |
| 2012/0238876 A1 | 9/2012 | Tanabe et al. | |
| 2012/0279865 A1 | 11/2012 | Regniere et al. | |
| 2012/0288641 A1 | 11/2012 | Diatezua et al. | |
| 2013/0051179 A1 | 2/2013 | Hong | |
| 2013/0064043 A1 | 3/2013 | Degertekin et al. | |
| 2013/0127592 A1 | 5/2013 | Fyke et al. | |
| 2013/0133428 A1 | 5/2013 | Lee et al. | |
| 2013/0201134 A1 | 8/2013 | Schneider et al. | |
| 2013/0294202 A1 | 11/2013 | Hajati | |
| 2014/0060196 A1 * | 3/2014 | Falter | G01N 29/262 73/632 |
| 2014/0117812 A1 * | 5/2014 | Hajati | B06B 1/0276 310/314 |
| 2014/0176332 A1 | 6/2014 | Alameh et al. | |
| 2014/0208853 A1 | 7/2014 | Onishi et al. | |
| 2014/0219521 A1 * | 8/2014 | Schmitt | G06K 9/0002 382/124 |
| 2014/0232241 A1 * | 8/2014 | Hajati | B81B 7/008 310/317 |
| 2014/0265721 A1 | 9/2014 | Robinson et al. | |
| 2014/0355387 A1 | 12/2014 | Kitchens et al. | |
| 2015/0036065 A1 | 2/2015 | Yousefpor et al. | |
| 2015/0049590 A1 | 2/2015 | Rowe et al. | |

(56) References Cited

U.S. PATENT DOCUMENTS

| | | | |
|---|---|---|---|
| 2015/0087991 A1* | 3/2015 | Chen | G01S 7/5202 600/459 |
| 2015/0097468 A1 | 4/2015 | Hajati et al. | |
| 2015/0145374 A1 | 5/2015 | Xu et al. | |
| 2015/0164473 A1* | 6/2015 | Kim | A61B 8/4483 600/443 |
| 2015/0165479 A1 | 6/2015 | Lasiter et al. | |
| 2015/0169136 A1 | 6/2015 | Ganti et al. | |
| 2015/0189136 A1 | 7/2015 | Chung et al. | |
| 2015/0198699 A1 | 7/2015 | Kuo et al. | |
| 2015/0206738 A1 | 7/2015 | Rastegar | |
| 2015/0213180 A1 | 7/2015 | Herberholz | |
| 2015/0220767 A1 | 8/2015 | Yoon et al. | |
| 2015/0261261 A1 | 9/2015 | Bhagavatula et al. | |
| 2015/0286312 A1 | 10/2015 | Kang et al. | |
| 2015/0345987 A1* | 12/2015 | Hajati | B06B 1/06 73/661 |
| 2016/0051225 A1 | 2/2016 | Kim et al. | |
| 2016/0063294 A1 | 3/2016 | Du et al. | |
| 2016/0086010 A1 | 3/2016 | Merrell et al. | |
| 2016/0092716 A1 | 3/2016 | Yazdandoost et al. | |
| 2016/0100822 A1* | 4/2016 | Kim | A61B 8/4483 600/472 |
| 2016/0107194 A1* | 4/2016 | Panchawagh | G06F 3/043 367/140 |
| 2016/0326477 A1 | 11/2016 | Fernandez-Alcon et al. | |
| 2016/0358003 A1 | 12/2016 | Shen et al. | |
| 2017/0075700 A1 | 3/2017 | Abudi et al. | |
| 2017/0100091 A1 | 4/2017 | Eigil et al. | |
| 2017/0110504 A1 | 4/2017 | Panchawagh et al. | |
| 2017/0119343 A1 | 5/2017 | Pintoffl | |
| 2017/0168543 A1 | 6/2017 | Dai et al. | |
| 2017/0219536 A1 | 8/2017 | Koch et al. | |
| 2017/0231534 A1 | 8/2017 | Agassy et al. | |
| 2017/0255338 A1 | 9/2017 | Medina et al. | |
| 2017/0293791 A1 | 10/2017 | Mainguet et al. | |
| 2017/0322290 A1 | 11/2017 | Ng | |
| 2017/0322291 A1 | 11/2017 | Salvia et al. | |
| 2017/0322292 A1 | 11/2017 | Salvia et al. | |
| 2017/0322305 A1* | 11/2017 | Apte | G01S 15/06 |
| 2017/0323133 A1 | 11/2017 | Tsai | |
| 2017/0326590 A1 | 11/2017 | Daneman | |
| 2017/0326591 A1 | 11/2017 | Apte et al. | |
| 2017/0326593 A1* | 11/2017 | Garlepp | B06B 1/0629 |
| 2017/0326594 A1 | 11/2017 | Berger et al. | |
| 2017/0328866 A1 | 11/2017 | Apte et al. | |
| 2017/0328870 A1 | 11/2017 | Garlepp et al. | |
| 2017/0330012 A1 | 11/2017 | Salvia et al. | |
| 2017/0330552 A1* | 11/2017 | Garlepp | B06B 1/0629 |
| 2017/0330553 A1 | 11/2017 | Garlepp et al. | |
| 2017/0357839 A1 | 12/2017 | Yazdandoost et al. | |
| 2018/0206820 A1 | 7/2018 | Anand et al. | |
| 2018/0349663 A1 | 12/2018 | Garlepp et al. | |
| 2018/0357457 A1 | 12/2018 | Rasmussen et al. | |
| 2018/0369866 A1 | 12/2018 | Sammoura et al. | |
| 2019/0005300 A1 | 1/2019 | Garlepp et al. | |
| 2019/0102046 A1 | 4/2019 | Miranto et al. | |

FOREIGN PATENT DOCUMENTS

| | | |
|---|---|---|
| JP | 2011040467 A | 2/2011 |
| WO | 2009096576 A2 | 8/2009 |
| WO | 2009137106 A2 | 11/2009 |
| WO | 2014035564 A1 | 3/2014 |
| WO | 2015009635 A1 | 1/2015 |
| WO | 2015112453 A1 | 7/2015 |
| WO | 2015120132 A1 | 8/2015 |
| WO | 2015131083 A1 | 9/2015 |
| WO | 2015183945 A1 | 12/2015 |
| WO | 2016007250 A1 | 1/2016 |
| WO | 2016011172 A1 | 1/2016 |
| WO | 2016040333 A2 | 3/2016 |
| WO | 2017003848 A1 | 1/2017 |
| WO | 2017192895 A1 | 11/2017 |
| WO | 2017196678 A1 | 11/2017 |
| WO | 2017196682 A1 | 11/2017 |
| WO | 2017192903 A3 | 12/2017 |

OTHER PUBLICATIONS

ISA/EP, International Search Report and Written Opinion for International Application No. PCT/US2017/031120, 13 pages, dated Sep. 1, 2017 (dated Sep. 1, 2017).

ISA/EP, International Search Report and Written Opinion for International Application No. PCT/US2017/031134, 12 pages, dated Aug. 30, 2017 (dated Aug. 30, 2017).

ISA/EP, International Search Report and Written Opinion for International Application No. PCT/US2017/031421 13 pages, dated Jun. 21, 2017 (dated Jun. 21, 2017).

ISA/EP, International Search Report and Written Opinion for International Application No. PCT/US2017/031426 13 pages, dated Jun. 22, 2017 (dated Jun. 22, 2017).

ISA/EP, International Search Report and Written Opinion for International Application No. PCT/US2017/031431, 14 pages, dated Aug. 1, 2017 (dated Aug. 1, 2017).

ISA/EP, International Search Report and Written Opinion for International Application No. PCT/US2017/031434, 13 pages, dated Jun. 26, 2017 (dated Jun. 26, 2017).

ISA/EP, International Search Report and Written Opinion for International Application No. PCT/US2017/031439, 10 pages, dated Jun. 20, 2017 (dated Jun. 20, 2017).

ISA/EP, International Search Report and Written Opinion for International Application No. PCT/US2017/031824, 18 pages, dated Sep. 22, 2017 (dated Sep. 22, 2017).

ISA/EP, International Search Report and Written Opinion for International Application No. PCT/US2017/031827, 16 pages, dated Aug. 1, 2017 (dated Aug. 1, 2017).

ISA/EP, International Search Report and Written Opinion for International Application No. PCT/US2017/031831, 12 pages, dated Jul. 21, 2017 (dated Jul. 21, 2017).

ISA/EP, Partial International Search Report for International Application No. PCT/US2017/031140, 13 pages, dated Aug. 29, 2017 (dated Aug. 29, 2017).

Rozen, et al., "Air-Coupled Aluminum Nitride Piezoelectric Micromachined Ultrasonic Transducers at 0.3 Mhz to 0.9 Mhz", 2015 28th IEEE International Conference on Micro Electro Mechanical Systems (MEMS), IEEE, Jan. 18, 2015, 921-924.

Tang, et al., "Pulse-Echo Ultrasonic Fingerprint Sensor on a Chip", IEEE Transducers, Anchorage, Alaska, USA, Jun. 21-25, 2015, pp. 674-677.

Dausch, et al., "Theory and Operation of 2-D Array Piezoelectric Micromachined Ultrasound Transducers", IEEE Transactions on Ultrasonics, and Frequency Control, vol. 55, No. 11;, Nov. 2008, 2484-2492.

Hopcroft, et al., "Temperature Compensation of a MEMS Resonator Using Quality Factor as a Thermometer", Retrieved from Internet: http://micromachine.stanford.edu/~amanu/linked/MAH_MEMS2006.pdf, 2006, 222-225.

Hopcroft, et al., "Using the temperature dependence of resonator quality factor as a thermometer", Applied Physics Letters 91. Retrieved from Internet: http://micromachine.stanford.edu/~hopcroft/Publications/Hopcroft_QT_ApplPhysLett_91_013505.pdf, 2007, 013505-1-031505-3.

Lee, et al., "Low jitter and temperature stable MEMS oscillators", Frequency Control Symposium (FCS), 2012 IEEE International, May 2012, 1-5.

Li, et al., "Capacitive micromachined ultrasonic transducer for ultra-low pressure measurement: Theoretical study", AIP Advances 5.12. Retrieved from Internet: http://scitation.aip.org/content/aip/journal/adva/5/12/10.1063/1.4939217, 2015, 127231.

Qiu, et al., "Piezoelectric Micromachined Ultrasound Transducer (PMUT) Arrays for Integrated Sensing, Actuation and Imaging", Sensors 15, doi:10.3390/s150408020, Apr. 3, 2015, 8020-8041.

Savoia, et al., "Design and Fabrication of a cMUT Probe for Ultrasound Imaging of Fingerprints", 2010 IEEE International Ultrasonics Symposium Proceedings, Oct. 2010, 1877-1880.

(56) References Cited

OTHER PUBLICATIONS

Shen, et al., "Anisotropic Complementary Acoustic Metamaterial for Canceling out Aberrating Layers", American Physical Society, Physical Review X 4.4: 041033., Nov. 19, 2014, 041033-1-041033-7.

Thakar, et al., "Multi-resonator approach to eliminating the temperature dependence of silicon-based timing references", Hilton Head'14. Retrieved from the Internet: http://blog.narotama.ac.id/wp-content/uploads/2014/12/Multi-resonator-approach-to-eliminating-the-temperature-dependance-of-silicon-based-timing-references.pdf, 2014, 415-418.

ISA/EP, International Search Report and Written Opinion for International Application No. PCT/US2017/031140, 18 pages, dated Nov. 2, 2017 (dated Nov. 2, 2017).

ISA/EP, International Search Report for International Application No. PCT/US2017/031826, 16 pages, dated Feb. 27, 2018 (dated Feb. 27, 2018).

ISA/EP, Partial International Search Report for International Application No. PCT/US2017/031823, 12 pages, dated Nov. 30, 2017 (dated Nov. 30, 2017).

ISA/EP, International Search Report and Written Opinion for International Application # PCT/US2018/063431, pp. 1-15, dated Feb. 5, 2019 (dated Feb. 5, 2019).

"Moving Average Filters", Waybackmachine XP05547422, Retrieved from the Internet: URL:https://web.archive.org/web/20170809081353/https//www.analog.com/media/en/technical-documentation/dsp-book/dsp_book_Ch15.pdf [retrieved on Jan. 24, 2019], Aug. 9, 2017, 1-8.

"Receiver Thermal Noise Threshold", Fisher Telecommunication Services, Satellite Communications. Retrieved from the Internet: URL:https://web.archive.org/web/20171027075705/http//www.fishercom.xyz:80/satellite-communications/receiver-thermal-noise-threshold.html, Oct. 27, 2017, 3.

"Sleep Mode", Wikipedia, Retrieved from the Internet: URL:https://web.archive.org/web/20170908153323/https://en.wikipedia.org/wiki/Sleep_mode [retrieved on Jan. 25, 2019], Sep. 8, 2017, 1-3.

"TMS320C5515 Fingerprint Development Kit (FDK) Hardware Guide", Texas Instruments, Literature No. SPRUFX3, XP055547651, Apr. 2010, 1-26.

"Zte V7 MAX. 5,5" smartphone on MediaTeck Helio P10 cpu; Published on Apr. 20, 2016; https://www.youtube.com/watch?v=ncNCbpkGQzU (Year 2016)".

"ISA/EP, International Search Report and Written Opinion for International Application # PCT/US2019/015020, pp. 1-23, dated Jul. 1, 2019 (dated Jul. 1, 2019)".

"ISA/EP, International Search Report and Written Opinion for International Application # PCT/US2019/023440, pp. 1-10, dated Jun. 4, 2019 (dated Jun. 4, 2019)".

Cappelli, et al., "Fingerprint Inage Reconstruction from Standard Templates", IEEE Transactions on Pattern Analysis and Machine Intelligence, IEEE Computer Society, vol. 29, No. 9, Sep. 2007, 1489-1503.

Feng, et al., "Fingerprint Reconstruction: From Minutiae to Phase", IEEE Transactions on Pattern Analysis and Machine Intelligence, IEEE Computer Society, vol. 33, No. 2, Feb. 2011, 209-223.

Kumar, et al., "Towards Contactless, Low-Cost and Accurate 3D Fingerprint Identification", IEEE Transactions on Pattern Analysis and Machine Intelligence, IEEE Computer Society, vol. 37, No. 3, Mar. 2015, 681-696.

Pang, et al., "Extracting Valley-Ridge Lines from Point-Cloud-Based 3D Fingerprint Models", IEEE Computer Graphics and Applications, IEEE Service Center, New York, vol. 33, No. 4, Jul./Aug. 2013, 73-81.

Ross, et al., "From Template to Image: Reconstructing Fingerprints from Minutiae Points", IEEE Transactions on Pattern Analysis and Machine Intelligence, IEEE Computer Society, vol. 29, No. 4, Apr. 2007, 544-560.

Zhou, et al., "Partial Fingerprint Reconstruction with Improved Smooth Extension", Network and System Security, Berlin Heidelberg, Jun. 3, 2013, 756-762.

ISA/EP, Partial International Search Report for International Application No. PCT/US2019/034032, 8 pages, Sep. 12, 2019, 8.

Papageorgiou, et al., "Self-Calibration of Ultrasonic Transducers in an Intelligent Data Acquisition System", International Scientific Journal of Computing, 2003, vol. 2, Issue 2 Retrieved Online: URL: https://scholar.google.com/scholar?q=self-calibration+of+ultrasonic+transducers+in+an+intelligent+data+acquisition+system&hl=en&as_sdt=0&as_vis=1&oi=scholart, 2003, 9-15.

* cited by examiner

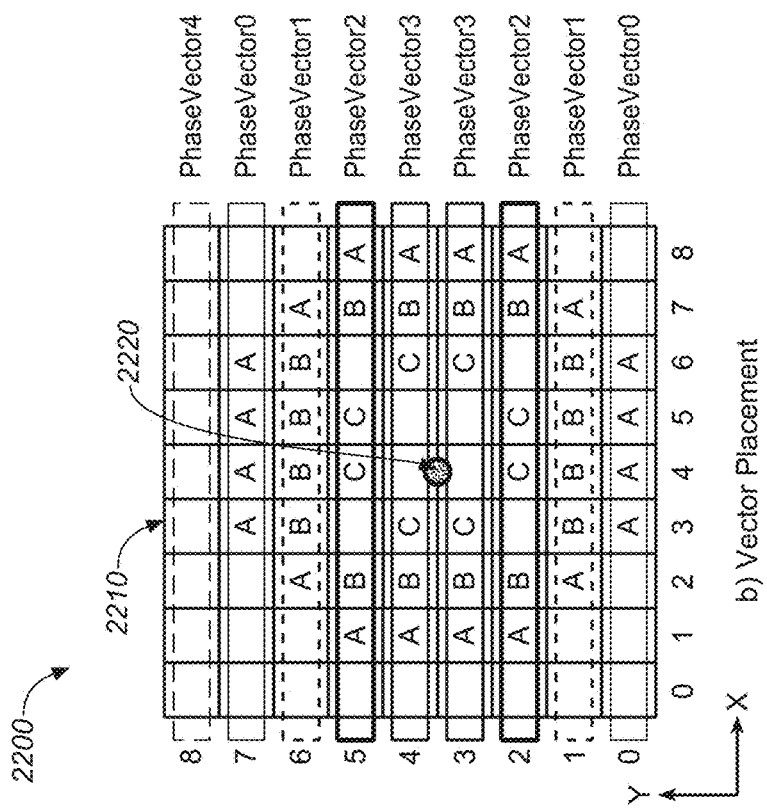
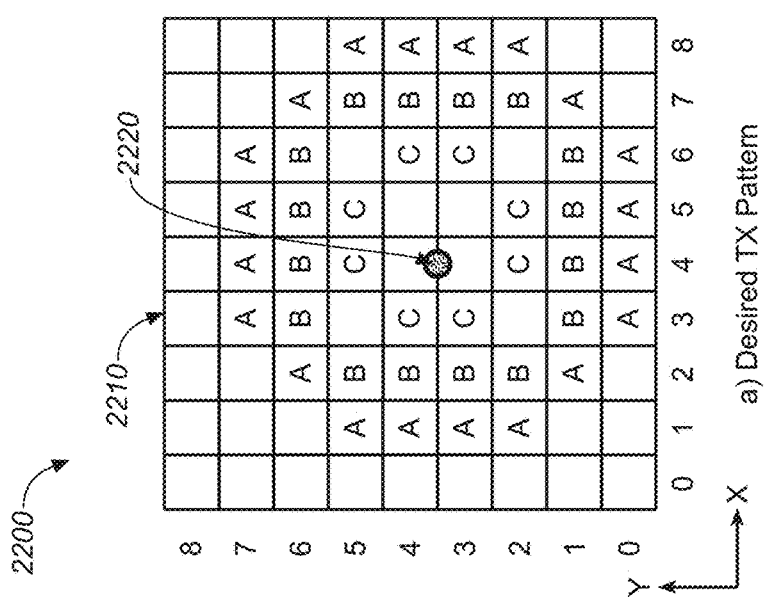
FIG. 22A
FIG. 22B

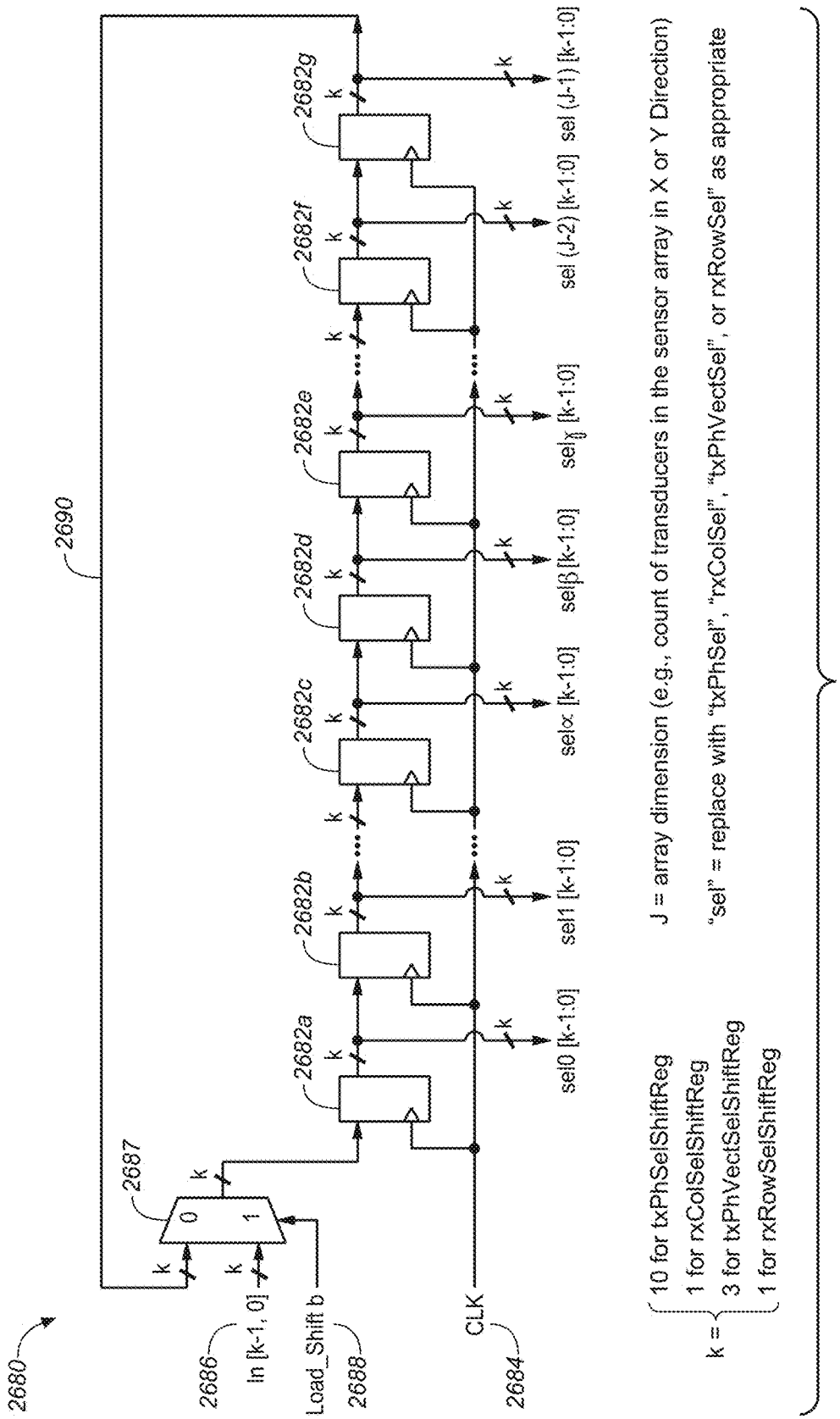

OPERATION OF AN ULTRASONIC SENSOR

RELATED APPLICATIONS

This application claims also priority to and the benefit of U.S. Provisional Patent Application 62/334,399, filed on May 10, 2016, entitled "ULTRASONIC SENSOR ELECTRONICS," by Salvia, et al., and assigned to the assignee of the present application, which is incorporated herein by reference in its entirety.

BACKGROUND

Piezoelectric materials facilitate conversion between mechanical energy and electrical energy. Moreover, a piezoelectric material can generate an electrical signal when subjected to mechanical stress, and can vibrate when subjected to an electrical voltage. Piezoelectric materials are widely utilized in piezoelectric ultrasonic transducers to generate acoustic waves based on an actuation voltage applied to electrodes of the piezoelectric ultrasonic transducer.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

FIG. 13 illustrates an example phase delay pattern for a 9×9 ultrasonic transducer block, according to some embodiments.

FIG. 14 illustrates another example phase delay pattern for a 9×9 ultrasonic transducer block, according to some embodiments.

FIG. 22A illustrates another example beamforming pattern within a beamforming space.

FIG. 22B illustrates another example phase vector placement within beamforming space to provide a beamforming pattern, according to an embodiment.

FIG. 26B illustrates an example shift register, according to an embodiment.

DESCRIPTION OF EMBODIMENTS

Figure 1A:
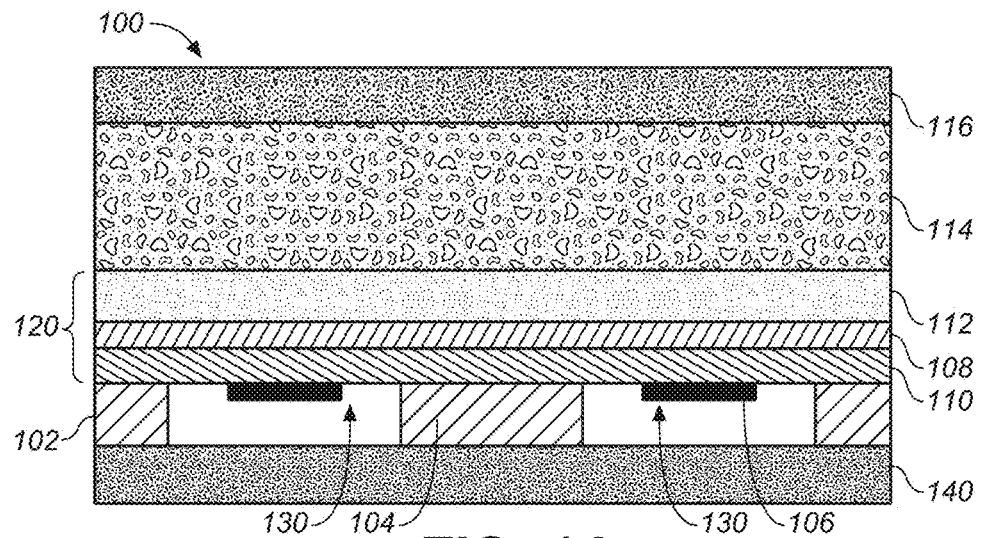
FIG. 1A is a diagram illustrating a piezoelectric micromachined ultrasonic transducer (PMUT) device having a center pinned membrane, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "defining," "applying," "performing," "populating," "generating," "repeating," "sensing," "imaging," "storing," "controlling," "shifting," "selecting," "controlling," "applying," or the like, refer to the actions and processes of an electronic device such as an electrical device or an ultrasonic sensor.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example systems described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As is employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

Overview of Discussion

Discussion begins with a description of an example Piezoelectric Micromachined Ultrasonic Transducer (PMUT), in accordance with various embodiments. Example arrays including PMUT devices are then described. Example operations of the example arrays of PMUT devices are then further described. Example sensor array configurations are then described. Example beamforming patterns within a beamforming space are then described. Example transmit operations and receive operations of an ultrasonic sensor are then described.

A conventional piezoelectric ultrasonic transducer able to generate and detect pressure waves can include a membrane with the piezoelectric material, a supporting layer, and electrodes combined with a cavity beneath the electrodes. Miniaturized versions are referred to as PMUTs. Typical PMUTs use an edge anchored membrane or diaphragm that maximally oscillates at or near the center of the membrane at a resonant frequency (f) proportional to $h/a^2$, where h is the thickness, and a is the radius of the membrane. Higher frequency membrane oscillations can be created by increasing the membrane thickness, decreasing the membrane radius, or both. Increasing the membrane thickness has its limits, as the increased thickness limits the displacement of the membrane. Reducing the PMUT membrane radius also has limits, because a larger percentage of PMUT membrane area is used for edge anchoring.

Embodiments described herein relate to a PMUT device for ultrasonic wave generation and sensing. In accordance with various embodiments, an array of such PMUT devices is described. The PMUT includes a substrate and an edge support structure connected to the substrate. A membrane is connected to the edge support structure such that a cavity is defined between the membrane and the substrate, where the membrane is configured to allow movement at ultrasonic frequencies. The membrane includes a piezoelectric layer and first and second electrodes coupled to opposing sides of the piezoelectric layer. An interior support structure is disposed within the cavity and connected to the substrate and the membrane. In some embodiments, the interior support structure may be omitted.

The described PMUT device and array of PMUT devices can be used for generation of acoustic signals or measurement of acoustically sensed data in various applications, such as, but not limited to, medical applications, security systems, biometric systems (e.g., fingerprint sensors and/or motion/gesture recognition sensors), mobile communication systems, industrial automation systems, consumer electronic devices, robotics, etc. In one embodiment, the PMUT device can facilitate ultrasonic signal generation and sensing (transducer). Moreover, embodiments describe herein provide a sensing component including a silicon wafer having a two-dimensional (or one-dimensional) array of ultrasonic transducers.

Embodiments described herein provide a PMUT that operates at a high frequency for reduced acoustic diffraction through high acoustic velocity materials (e.g., glass, metal), and for shorter pulses so that spurious reflections can be time-gated out. Embodiments described herein also provide a PMUT that has a low quality factor providing a shorter ring-up and ring-down time to allow better rejection of spurious reflections by time-gating. Embodiments described herein also provide a PMUT that has a high fill-factor providing for large transmit and receive signals.

Embodiments described herein provide for transmit beamforming of a two-dimensional array of ultrasonic transducers. A beamforming pattern to apply to a beamforming space of the two-dimensional array of ultrasonic transducers is defined. The beamforming space includes a plurality of elements, where each element of the beamforming space corresponds to an ultrasonic transducer of the two-dimensional array of ultrasonic transducers, where the beamforming pattern identifies which ultrasonic transducers within the beamforming space are activated during a transmit operation of the two-dimensional array of ultrasonic transducers, and wherein at least some of the ultrasonic transducers that are activated are phase delayed with respect to other ultrasonic transducers that are activated. The beamforming pattern is applied to the two-dimensional array of ultrasonic transducers. A transmit operation is performed by activating the ultrasonic transducers of the beamforming space according to the beamforming pattern.

In one embodiment, a plurality of transmit signals is defined, where each transmit signal of the plurality of transmit signals has a different phase delay relative to other transmit signals of the plurality of transmit signals, and where elements corresponding to ultrasonic transducers that are activated during the transmit operation include an associated transmit signal of the plurality of transmit signals. In one embodiment, a plurality of phase vectors including a one-dimensional subset of elements of the plurality of elements is defined, where elements of a phase vector of the plurality of phase vectors include one of a null signal and the plurality of transmit signals, and where elements corresponding to ultrasonic transducers that are not activated during the transmit operation include the null signal.

Piezoelectric Micromachined Ultrasonic Transducer (PMUT)

Systems and methods disclosed herein, in one or more aspects provide efficient structures for an acoustic transducer (e.g., a piezoelectric actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

FIG. 1A is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections the sides or in vias through edge support 102 or interior support 104, electrically coupling lower electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes lower electrode 106, piezoelectric layer 110, and upper electrode 108, where lower electrode 106 and upper electrode 108 are coupled to opposing sides of piezoelectric layer 110. As shown, lower electrode 106 is coupled to a lower surface of piezoelectric layer 110 and upper electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 112 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 1B:
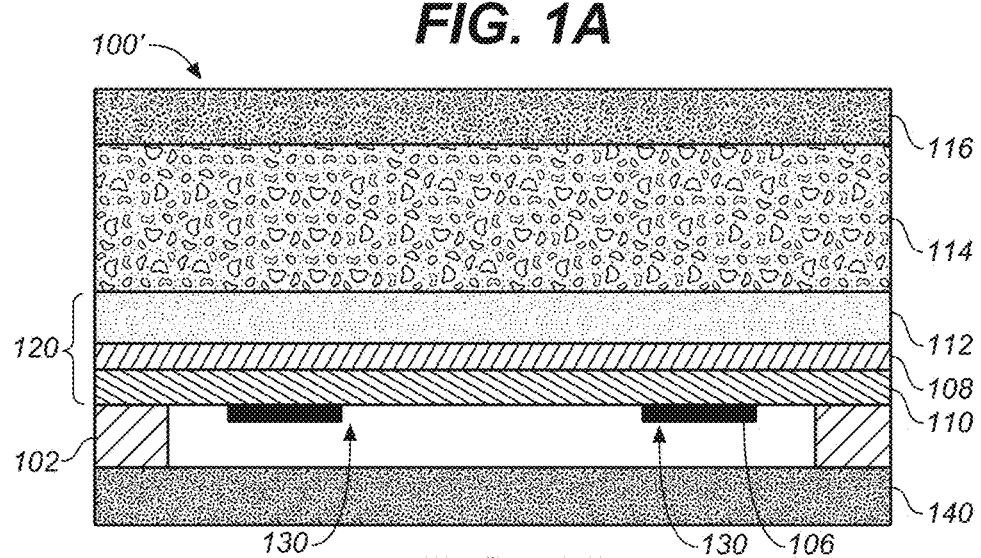
FIG. 1B is a diagram illustrating a PMUT device having an unpinned membrane, according to some embodiments.

FIG. 1B is identical to FIG. 1A in every way, except that the PMUT device 100' of FIG. 1B omits the interior support 104 and thus membrane 120 is not pinned (e.g., is "unpinned"). There may be instances in which an unpinned membrane 120 is desired. However, in other instances, a pinned membrane 120 may be employed.

Figure 2:
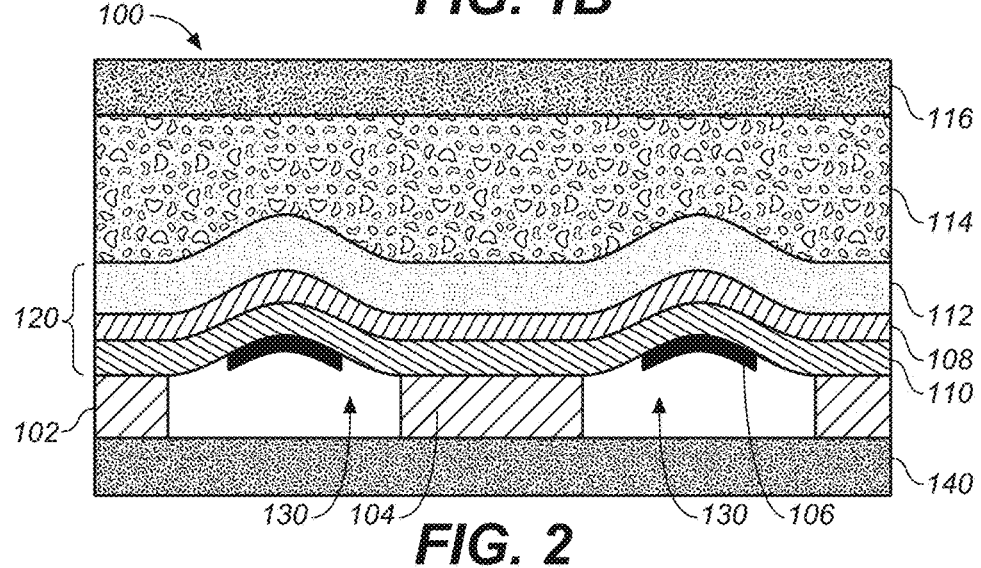
FIG. 2 is a diagram illustrating an example of membrane movement during activation of a PMUT device having a center pinned membrane, according to some embodiments.

FIG. 2 is a diagram illustrating an example of membrane movement during activation of pinned PMUT device 100, according to some embodiments. As illustrated with respect to FIG. 2, in operation, responsive to an object proximate platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to) distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, aluminum nitride (AlN), lead zirconate titanate (PZT), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Figure 7:
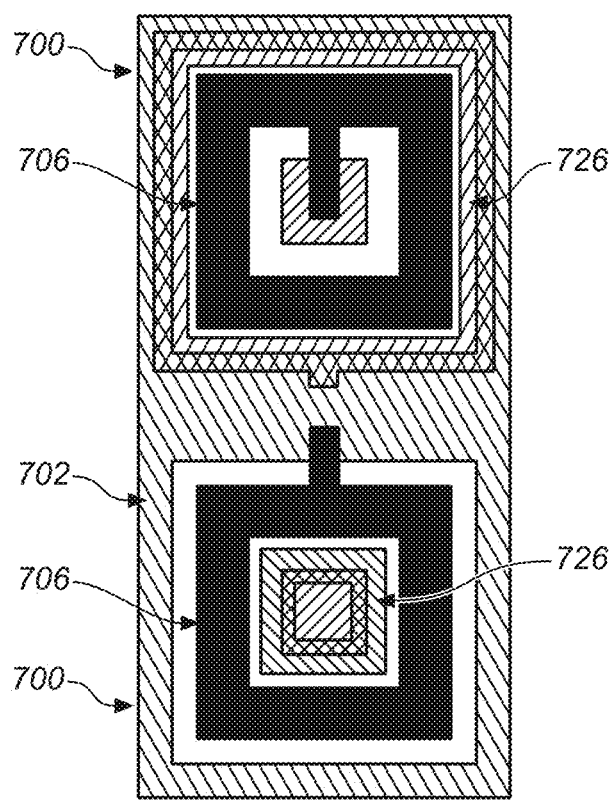
FIG. 7 illustrates an example pair of PMUT devices in a PMUT array, with each PMUT having differing electrode patterning, according to some embodiments.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, electrode 106 is a patterned electrode and electrode 108 is a continuous electrode. As an example, electrodes 106 and 108 can be comprised of almost any metal layers, such as, but not limited to, aluminum (Al)/titanium (Ti), molybdenum (Mo), etc., which are coupled with an on opposing sides of the piezoelectric layer 110. In one embodiment, PMUT device also includes a third electrode, as illustrated in FIG. 7 and described below.

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 Mega Rayleigh (MRayl), such as, but not limited to, plastic, resin, rubber, Teflon, epoxy, etc. In another example, the platen layer 116 can comprise various materials having a high acoustic impedance (e.g., an acoustic impendence greater than 10 MRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$ Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, titanium nitride (TiN), silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., aluminum (Al)/titanium (Ti), molybdenum (Mo), etc.) patterned to form electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, electrode 108 can be formed as a continuous layer providing a ground plane in contact with mechanical support layer 112, which can be formed from silicon or other suitable mechanical stiffening material. In still other embodiments, the electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

Figure 3:
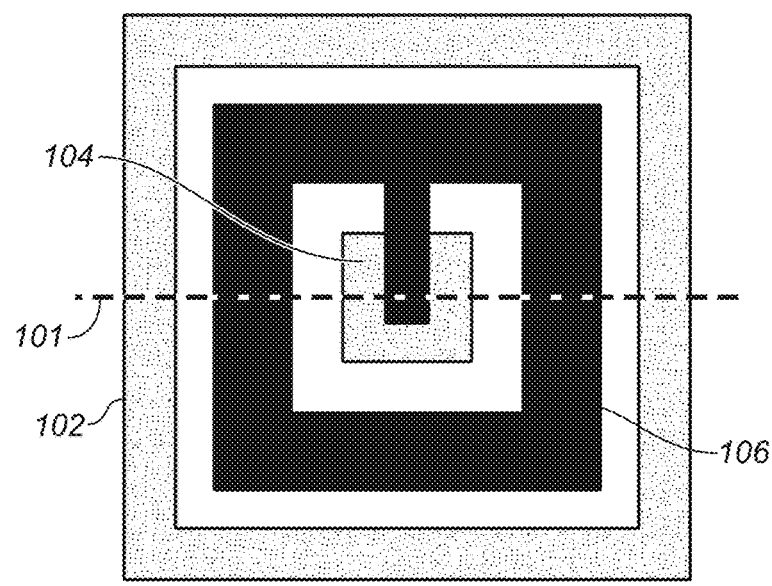
FIG. 3 is a top view of the PMUT device of FIG. 1A, according to some embodiments.

FIG. 3 is a top view of the PMUT device 100 of FIG. 1A having a substantially square shape, which corresponds in part to a cross section along dotted line 101 in FIG. 3. Layout of surrounding edge support 102, interior support 104, and lower electrode 106 are illustrated, with other continuous layers not shown. It should be appreciated that the term "substantially" in "substantially square shape" is intended to convey that a PMUT device 100 is generally square-shaped, with allowances for variations due to manufacturing processes and tolerances, and that slight deviation from a square shape (e.g., rounded corners, slightly wavering lines, deviations from perfectly orthogonal corners or intersections, etc.) may be present in a manufactured device. While a generally square arrangement PMUT device is shown, alternative embodiments including rectangular, hexagon, octagonal, circular, or elliptical are contemplated. In other embodiments, more complex electrode or PMUT device shapes can be used, including irregular and non-symmetric layouts such as chevrons or pentagons for edge support and electrodes.

Figure 4:
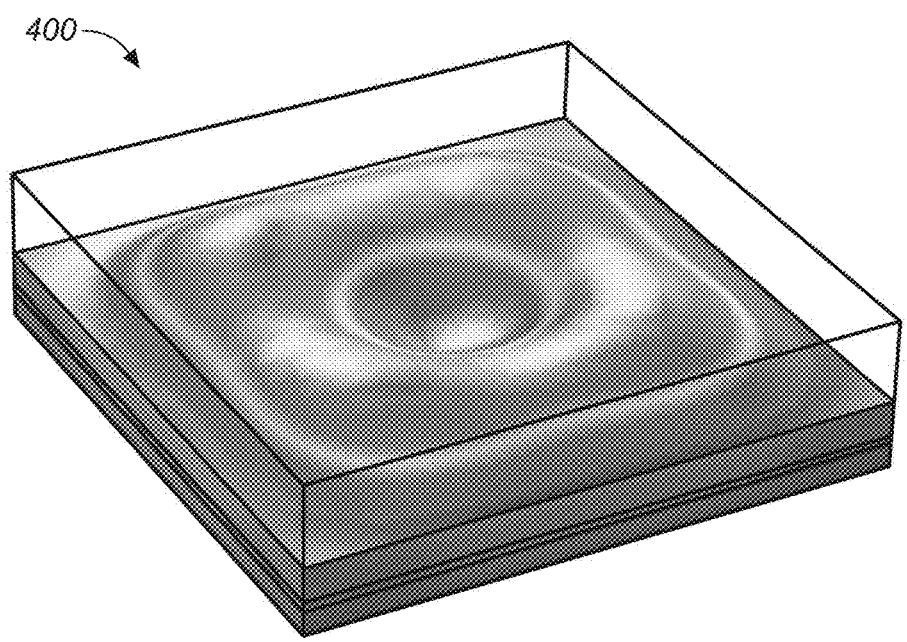
FIG. 4 is a simulated map illustrating maximum vertical displacement of the membrane of the PMUT device shown in FIGS. 1-3, according to some embodiments.

FIG. 4 is a simulated topographic map 400 illustrating maximum vertical displacement of the membrane 120 of the PMUT device 100 shown in FIGS. 1A-3. As indicated, maximum displacement generally occurs along a center axis of the lower electrode, with corner regions having the greatest displacement. As with the other figures, FIG. 4 is not drawn to scale with the vertical displacement exaggerated for illustrative purposes, and the maximum vertical displacement is a fraction of the horizontal surface area comprising the PMUT device 100. In an example PMUT device 100, maximum vertical displacement may be measured in nanometers, while surface area of an individual PMUT device 100 may be measured in square microns.

Figure 5:
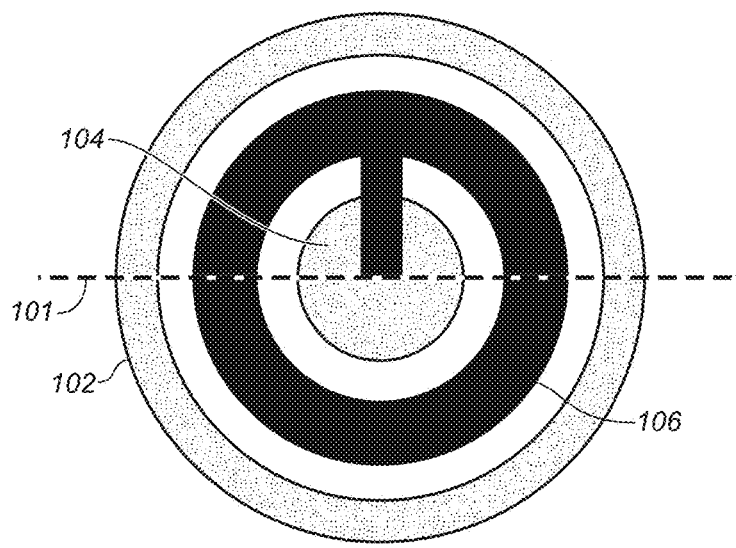
FIG. 5 is a top view of an example PMUT device having a circular shape, according to some embodiments.

FIG. 5 is a top view of another example of the PMUT device 100 of FIG. 1A having a substantially circular shape, which corresponds in part to a cross section along dotted line 101 in FIG. 5. Layout of surrounding edge support 102, interior support 104, and lower electrode 106 are illustrated, with other continuous layers not shown. It should be appreciated that the term "substantially" in "substantially circular shape" is intended to convey that a PMUT device 100 is generally circle-shaped, with allowances for variations due to manufacturing processes and tolerances, and that slight deviation from a circle shape (e.g., slight deviations on radial distance from center, etc.) may be present in a manufactured device.

Figure 6:
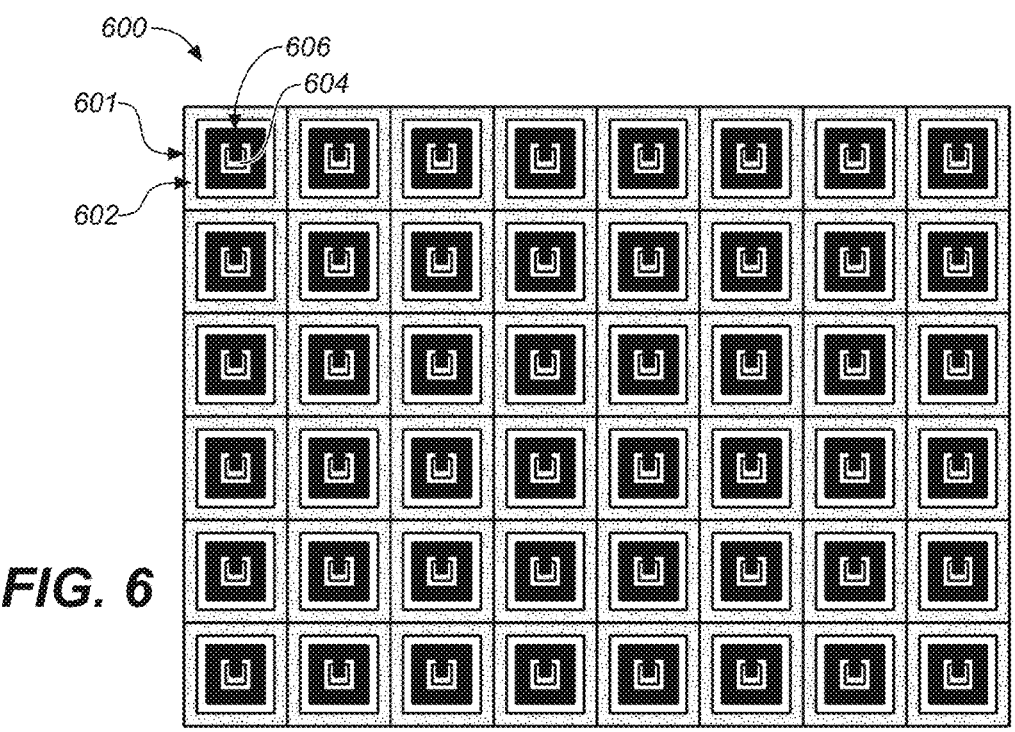
FIG. 6 illustrates an example array of square-shaped PMUT devices, according to some embodiments.

FIG. 6 illustrates an example two-dimensional array 600 of square-shaped PMUT devices 601 formed from PMUT devices having a substantially square shape similar to that discussed in conjunction with FIGS. 1A, 1B, 2, and 3. Layout of square surrounding edge support 602, interior support 604, and square-shaped lower electrode 606 surrounding the interior support 604 are illustrated, while other continuous layers are not shown for clarity. As illustrated, array 600 includes columns of square-shaped PMUT devices 601 that are in rows and columns. It should be appreciated that rows or columns of the square-shaped PMUT devices 601 may be offset. Moreover, it should be appreciated that square-shaped PMUT devices 601 may contact each other or be spaced apart. In various embodiments, adjacent square-shaped PMUT devices 601 are electrically isolated. In other embodiments, groups of adjacent square-shaped PMUT devices 601 are electrically connected, where the groups of adjacent square-shaped PMUT devices 601 are electrically isolated.

In operation, during transmission, selected sets of PMUT devices in the two-dimensional array can transmit an acoustic signal (e.g., a short ultrasonic pulse) and during sensing, the set of active PMUT devices in the two-dimensional array can detect an interference of the acoustic signal with an object (in the path of the acoustic wave). The received interference signal (e.g., generated based on reflections, echoes, etc. Of the acoustic signal from the object) can then be analyzed. As an example, an image of the object, a distance of the object from the sensing component, a density of the object, a motion of the object, etc., can all be determined based on comparing a frequency and/or phase of the interference signal with a frequency and/or phase of the acoustic signal. Moreover, results generated can be further analyzed or presented to a user via a display device (not shown).

FIG. 7 illustrates a pair of example PMUT devices 700 in a PMUT array, with each PMUT sharing at least one common edge support 702. As illustrated, the PMUT devices have two sets of independent lower electrode labeled as 706 and 726. These differing electrode patterns enable antiphase operation of the PMUT devices 700, and increase flexibility of device operation. In one embodiment, the pair of PMUTs may be identical, but the two electrodes could drive different parts of the same PMUT antiphase (one contracting, and one extending), such that the PMUT displacement becomes larger. While other continuous layers are not shown for clarity, each PMUT also includes an upper electrode (e.g., upper electrode 108 of FIG. 1A). Accordingly, in various embodiments, a PMUT device may include at least three electrodes.

FIGS. 8A, 8B, 8C, and 8D illustrate alternative examples of interior support structures, in accordance with various embodiments. Interior supports structures may also be referred to as "pinning structures," as they operate to pin the membrane to the substrate. It should be appreciated that interior support structures may be positioned anywhere within a cavity of a PMUT device, and may have any type of shape (or variety of shapes), and that there may be more than one interior support structure within a PMUT device. While FIGS. 8A, 8B, 8C, and 8D illustrate alternative examples of interior support structures, it should be appreciated that these examples or for illustrative purposes, and are not intended to limit the number, position, or type of interior support structures of PMUT devices.

Figure 8A:
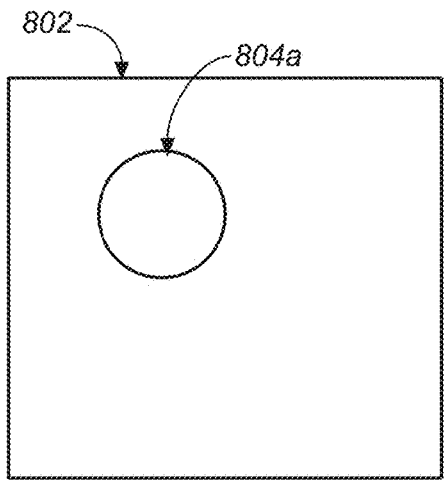
FIGS. 8A, 8B, 8C, and 8D illustrate alternative examples of interior support structures, according to various embodiments.
Figure 8B:
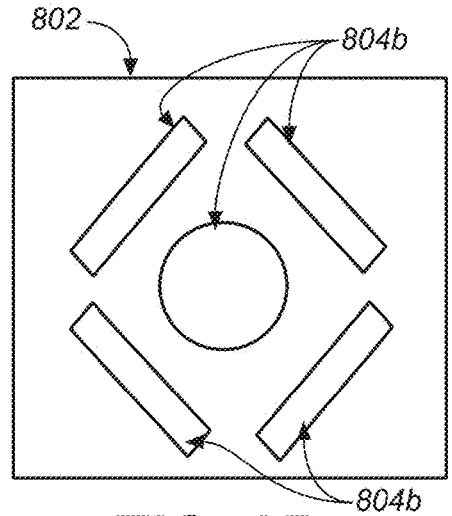
Figure 8C:
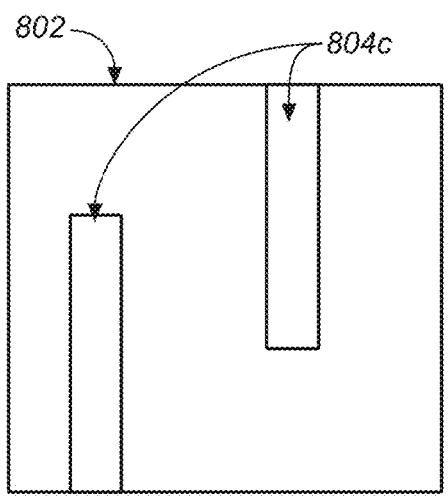
Figure 8D:
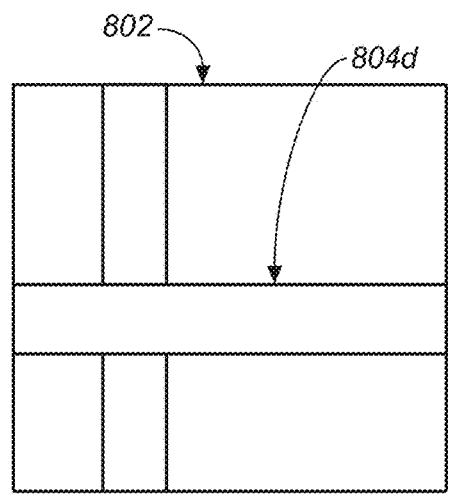

For example, interior supports structures do not have to be centrally located with a PMUT device area, but can be non-centrally positioned within the cavity. As illustrated in FIG. 8A, interior support 804a is positioned in a non-central, off-axis position with respect to edge support 802. In other embodiments such as seen in FIG. 8B, multiple interior supports 804b can be used. In this embodiment, one interior support is centrally located with respect to edge support 802, while the multiple, differently shaped and sized interior supports surround the centrally located support. In still other embodiments, such as seen with respect to FIGS. 8C and 8D, the interior supports (respectively 804c and 804d) can contact a common edge support 802. In the embodiment illustrated in FIG. 8D, the interior supports 804d can effectively divide the PMUT device into subpixels. This would allow, for example, activation of smaller areas to generate high frequency ultrasonic waves, and sensing a returning ultrasonic echo with larger areas of the PMUT device. It will be appreciated that the individual pinning structures can be combined into arrays.

Figure 9:
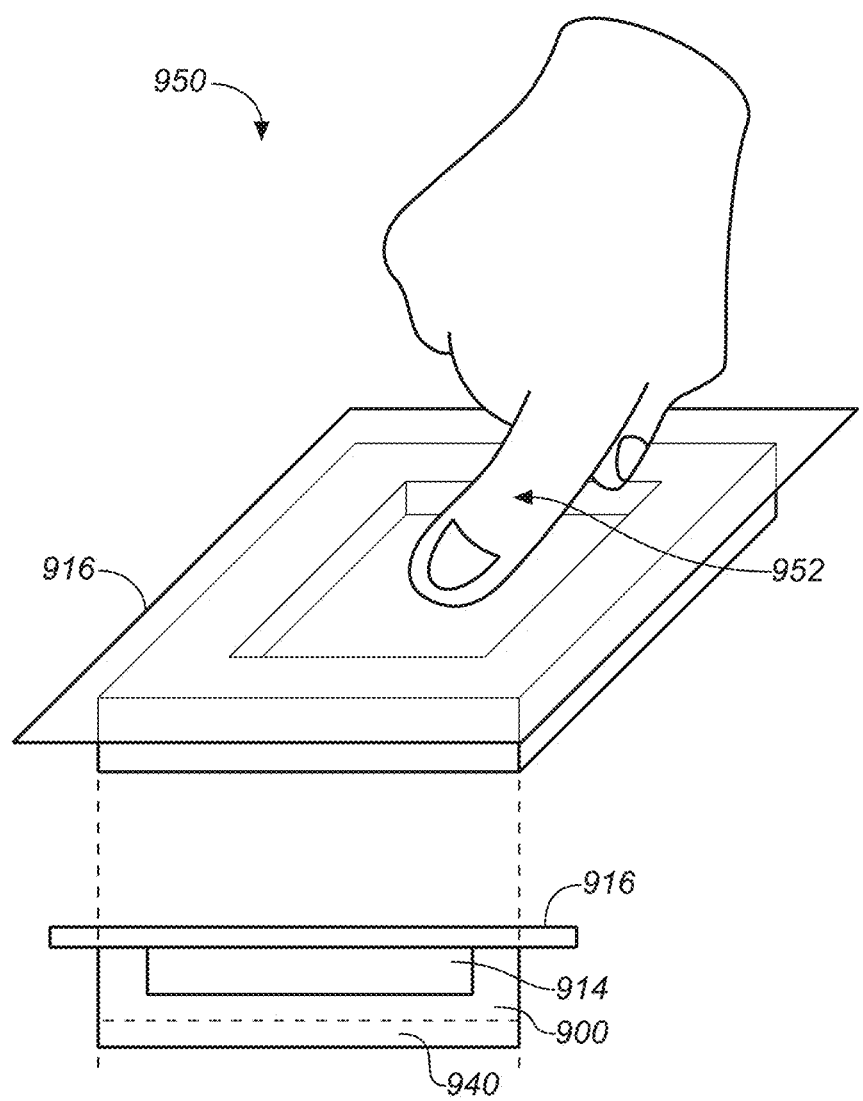
FIG. 9 illustrates a PMUT array used in an ultrasonic fingerprint sensing system, according to some embodiments.

FIG. 9 illustrates an embodiment of a PMUT array used in an ultrasonic fingerprint sensing system 950. The fingerprint sensing system 950 can include a platen 916 onto which a human finger 952 may make contact. Ultrasonic signals are generated and received by a PMUT device array 900, and travel back and forth through acoustic coupling layer 914 and platen 916. Signal analysis is conducted using processing logic module 940 (e.g., control logic) directly attached (via wafer bonding or other suitable techniques) to the PMUT device array 900. It will be appreciated that the size of platen 916 and the other elements illustrated in FIG. 9 may be much larger (e.g., the size of a handprint) or much smaller (e.g., just a fingertip) than as shown in the illustration, depending on the particular application.

In this example for fingerprinting applications, the human finger 952 and the processing logic module 940 can determine, based on a difference in interference of the acoustic signal with valleys and/or ridges of the skin on the finger, an image depicting epi-dermis and/or dermis layers of the finger. Further, the processing logic module 940 can compare the image with a set of known fingerprint images to facilitate identification and/or authentication. Moreover, in one example, if a match (or substantial match) is found, the identity of user can be verified. In another example, if a match (or substantial match) is found, a command/operation can be performed based on an authorization rights assigned to the identified user. In yet another example, the identified user can be granted access to a physical location and/or network/computer resources (e.g., documents, files, applications, etc.)

In another example, for finger-based applications, the movement of the finger can be used for cursor tracking/movement applications. In such embodiments, a pointer or cursor on a display screen can be moved in response to finger movement. It is noted that processing logic module 940 can include or be connected to one or more processors configured to confer at least in part the functionality of system 950. To that end, the one or more processors can execute code instructions stored in memory, for example, volatile memory and/or nonvolatile memory.

Figure 10:
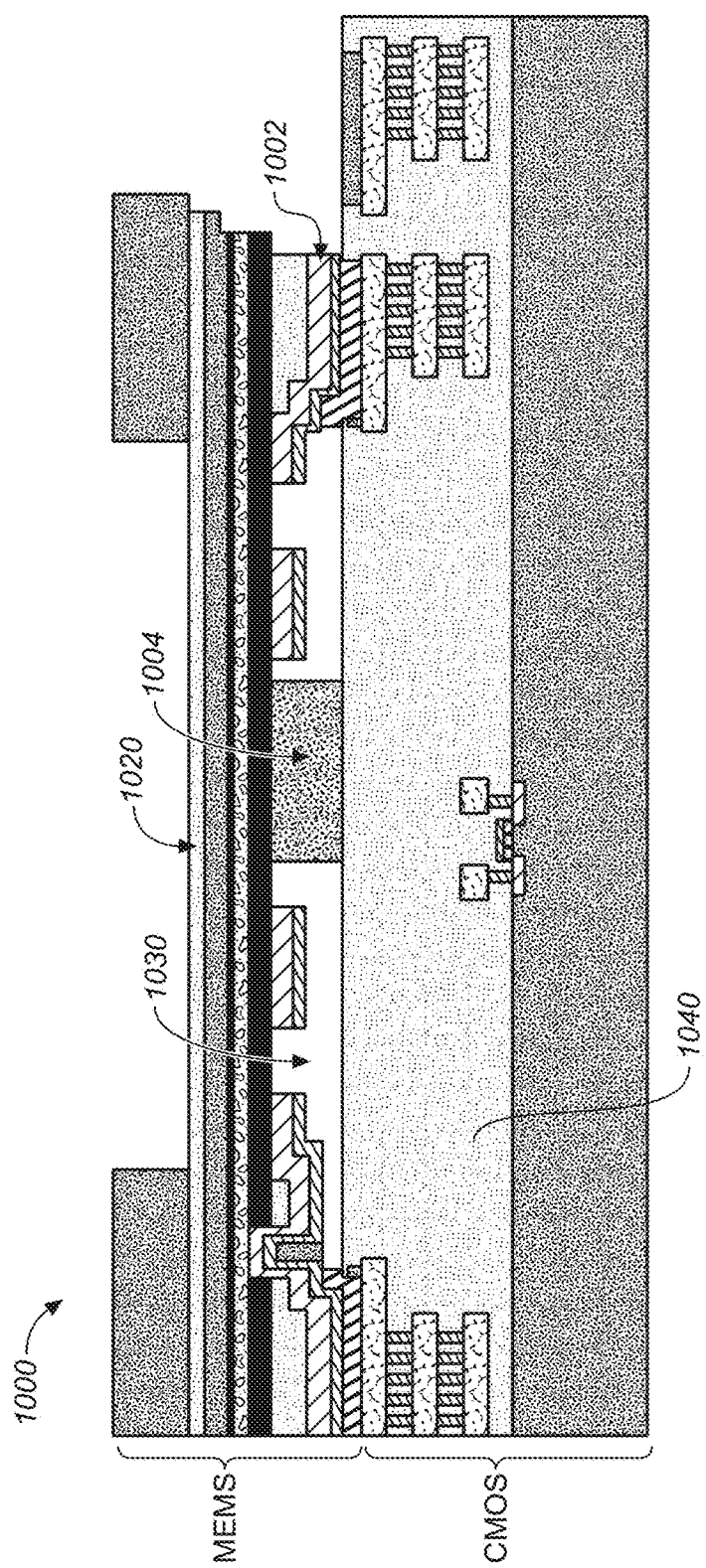
FIG. 10 illustrates an integrated fingerprint sensor formed by wafer bonding a CMOS logic wafer and a microelectromechanical (MEMS) wafer defining PMUT devices, according to some embodiments.

FIG. 10 illustrates an integrated fingerprint sensor 1000 formed by wafer bonding a CMOS logic wafer and a MEMS wafer defining PMUT devices, according to some embodiments. FIG. 10 illustrates in partial cross section one embodiment of an integrated fingerprint sensor formed by wafer bonding a substrate 1040 CMOS logic wafer and a MEMS wafer defining PMUT devices having a common edge support 1002 and separate interior support 1004. For example, the MEMS wafer may be bonded to the CMOS logic wafer using aluminum and germanium eutectic alloys, as described in U.S. Pat. No. 7,442,570. PMUT device 1000 has an interior pinned membrane 1020 formed over a cavity 1030. The membrane 1020 is attached both to a surrounding edge support 1002 and interior support 1004. The membrane 1020 is formed from multiple layers.

Example Operation of a Two-Dimensional Array of Ultrasonic Transducers

Systems and methods disclosed herein, in one or more aspects provide for the operation of a two-dimensional array of ultrasonic transducers (e.g., an array of piezoelectric actuated transducers or PMUTs). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

Figure 11:
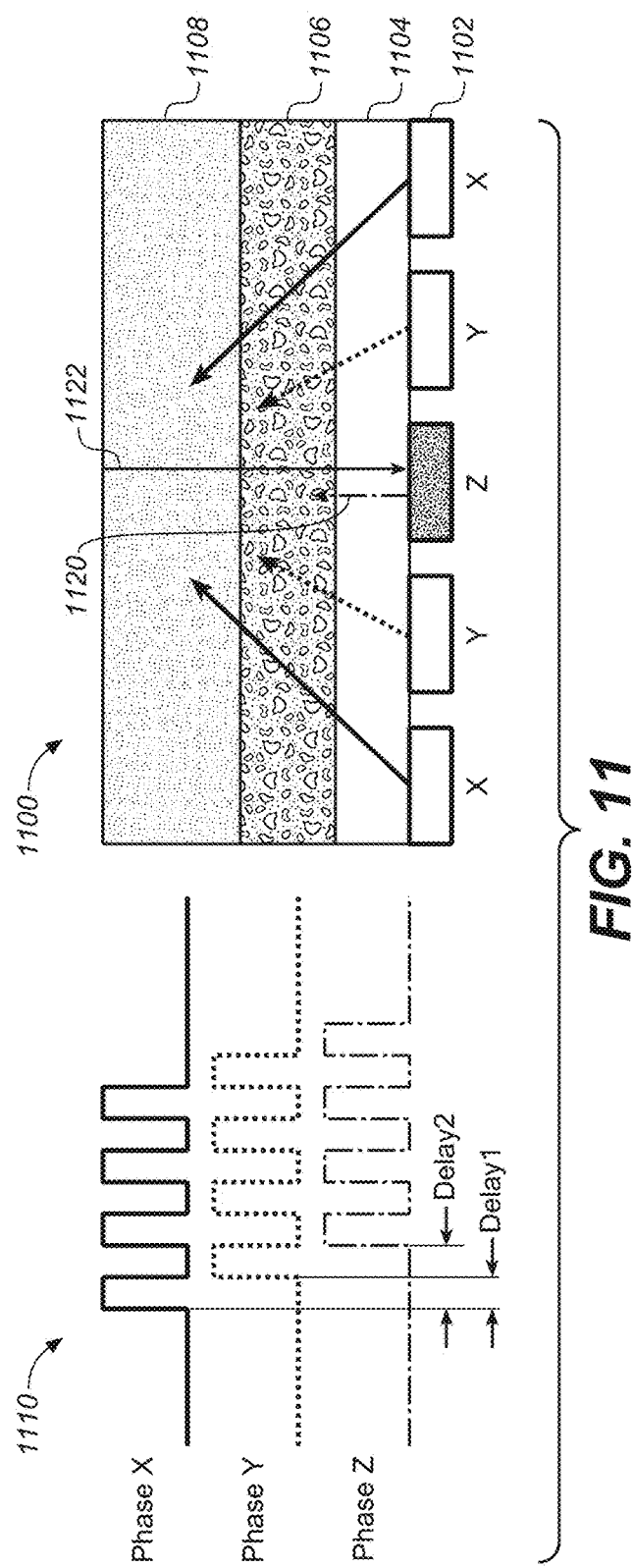
FIG. 11 illustrates an example ultrasonic transducer system with phase delayed transmission, according to some embodiments.

FIG. 11 illustrates an example ultrasonic transducer system 1100 with phase delayed transmission, according to some embodiments. As illustrated, FIG. 11 shows ultrasonic beam transmission and reception using a one-dimensional, five-element, ultrasonic transducer system 1100 having phase delayed inputs 1110. In various embodiments, ultrasonic transducer system 1100 is comprised of PMUT devices having a center pinned membrane (e.g., PMUT device 100 of FIG. 1A).

As illustrated, ultrasonic transducer system 1100 includes five ultrasonic transducers 1102 including a piezoelectric material and activating electrodes that are covered with a continuous stiffening layer 1104 (e.g., a mechanical support layer). Stiffening layer 1104 contacts acoustic coupling layer 1106, and in turn is covered by a platen layer 1108. In various embodiments, the stiffening layer 1104 can be silicon, and the platen layer 1108 formed from glass, sapphire, or polycarbonate or similar durable plastic. The intermediately positioned acoustic coupling layer 1106 can be formed from a plastic, epoxy, or gel such as polydimethylsiloxane (PDMS) or other material. In one embodiment, the material of acoustic coupling layer 1106 has an acoustic impedance selected to be between the acoustic impedance of layers 1104 and 1108. In one embodiment, the material of acoustic coupling layer 1106 has an acoustic impedance selected to be close the acoustic impedance of platen layer 1108, to reduce unwanted acoustic reflections and improve ultrasonic beam transmission and sensing. However, alternative material stacks to the one shown in FIG. 11 may be used and certain layers may be omitted, provided the medium through which transmission occurs passes signals in a predictable way.

In operation, and as illustrated in FIG. 11, the ultrasonic transducers 1102 labelled with an "x" are triggered to emit ultrasonic waves at an initial time. At a second time, (e.g., 1-100 nanoseconds later), the ultrasonic transducers 1102 labelled with a "y" are triggered. At a third time (e.g., 1-100 nanoseconds after the second time) the ultrasonic transducer 1102 labelled with a "z" is triggered. The ultrasonic waves interfere transmitted at different times cause interference with each other, effectively resulting in a single high intensity beam 1120 that exits the platen layer 1108, contacts objects, such as a finger (not shown), that contact the platen layer 1108, and is in part reflected back to the ultrasonic transducers. In one embodiment, the ultrasonic transducers 1102 are switched from a transmission mode to a reception mode, allowing the "z" ultrasonic transducer to detect any reflected signals 1122. In other words, the phase delay pattern of the ultrasonic transducers 1102 is symmetric about the focal point where high intensity beam 1120 exits platen layer 1108.

It should be appreciated that an ultrasonic transducer 1102 of ultrasonic transducer system 1100 may be used to transmit and/or receive an ultrasonic signal, and that the illustrated embodiment is a non-limiting example. The received signal (e.g., generated based on reflections, echoes, etc. of the acoustic signal from an object contacting or near the platen layer 1108) can then be analyzed. As an example, an image of the object, a distance of the object from the sensing component, acoustic impedance of the object, a motion of the object, etc., can all be determined based on comparing a frequency, amplitude, phase and/or arrival time of the received signal with a frequency, amplitude, phase and/or transmission time of the transmitted acoustic signal. Moreover, results generated can be further analyzed or presented to a user via a display device (not shown).

Figure 12:
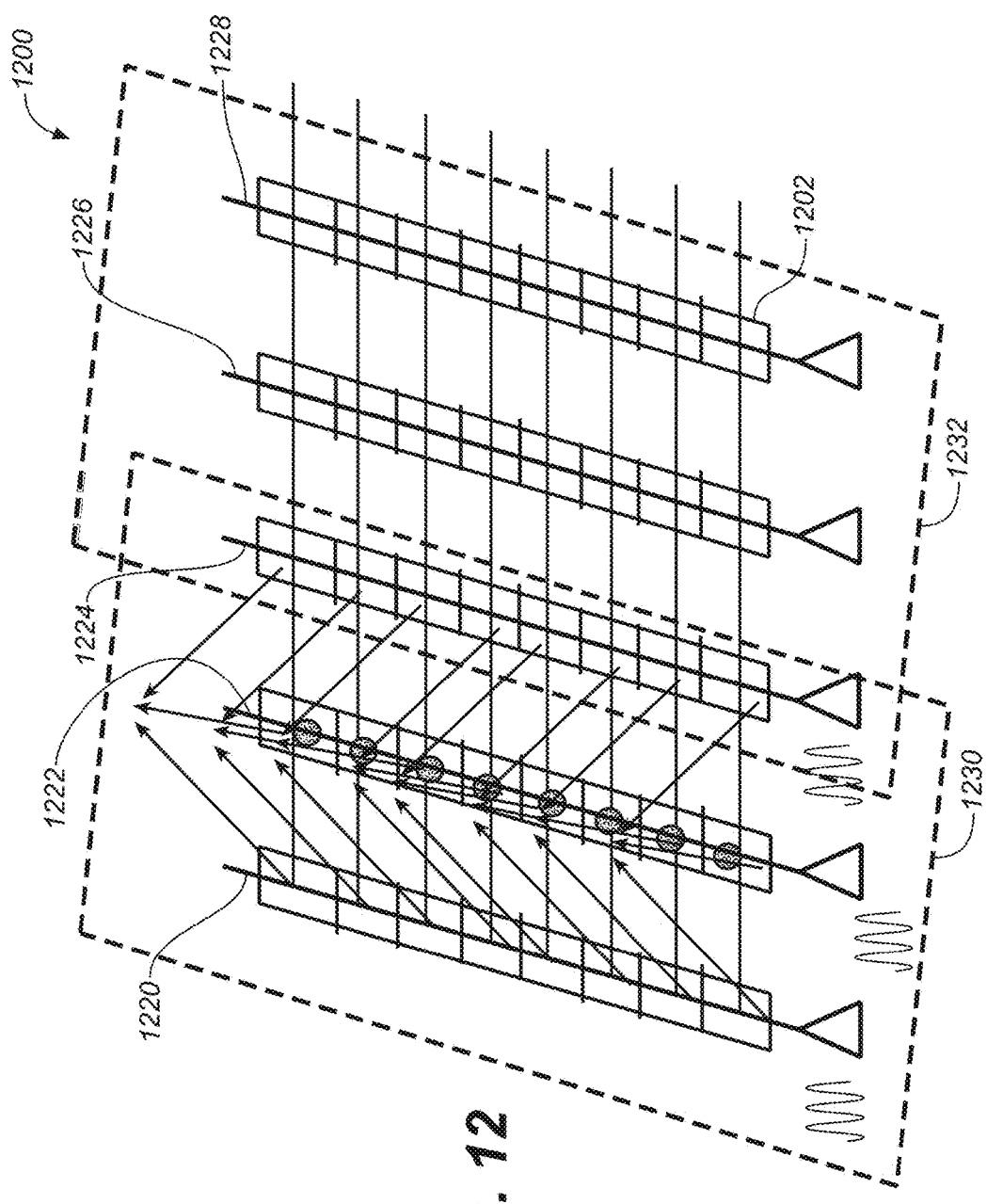
FIG. 12 illustrates another example ultrasonic transducer system with phase delayed transmission, according to some embodiments.

FIG. 12 illustrates another example ultrasonic transducer system 1200 with phase delayed transmission, according to some embodiments. As illustrated, FIG. 12 shows ultrasonic beam transmission and reception using a virtual block of two-dimensional, 24-element, ultrasonic transducers that form a subset of a 40-element ultrasonic transducer system 1200 having phase delayed inputs. In operation, an array position 1230 (represented by the dotted line), also referred to herein as a virtual block, includes columns 1220, 1222 and 1224 of ultrasonic transducers 1202. At an initial time, columns 1220 and 1224 of array position 1230 are triggered to emit ultrasonic waves at an initial time. At a second time (e.g., several nanoseconds later), column 1222 of array position 1230 is triggered. The ultrasonic waves interfere with each other, substantially resulting in emission of a high intensity ultrasonic wave centered on column 1222. In one embodiment, the ultrasonic transducers 1202 in columns 1220 and 1224 are switched off, while column 1222 is switched from a transmission mode to a reception mode, allowing detection of any reflected signals.

In one embodiment, after the activation of ultrasonic transducers 1202 of array position 1230, ultrasonic transducers 1202 of another array position 1232, comprised of columns 1224, 1226, and 1228 of ultrasonic transducers 1202 are triggered in a manner similar to that described in the foregoing description of array position 1230. In one embodiment, ultrasonic transducers 1202 of another array position 1232 are activated after a detection of a reflected ultrasonic signal at column 1222 of array position 1230. It should be appreciated that while movement of the array position by two columns of ultrasonic transducers is illustrated, movement by one, three, or more columns rightward or leftward is contemplated, as is movement by one or more rows, or by movement by both some determined number of rows and columns. In various embodiments, successive array positions can be either overlapping in part, or can be distinct. In some embodiments the size of array positions can be varied. In various embodiments, the number of ultrasonic transducers 1202 of an array position for emitting ultrasonic waves can be larger than the number of ultrasonic transducers 1202 of an array position for ultrasonic reception. In still other embodiments, array positions can be square, rectangular, ellipsoidal, circular, or more complex shapes such as crosses.

Example ultrasonic transducer system 1200 is operable to beamform a line of a high intensity ultrasonic wave centered over column 1222. It should be appreciated that the principles illustrated in FIG. 12 for beamforming a line using columns of ultrasonic transducers is applicable to embodiments for beamforming a point using ultrasonic transducers, as will be explained below. For instance, example ultrasonic transducer system 1200 includes columns of ultrasonic transducers in which the ultrasonic transducers of each column are jointly operated to activate at the same time, operating to beamform along a line. It should be appreciated that the ultrasonic transducers of a two-dimensional array may be independently operable, and used for beamform points as well, as will be described below.

Figures 13, 14:
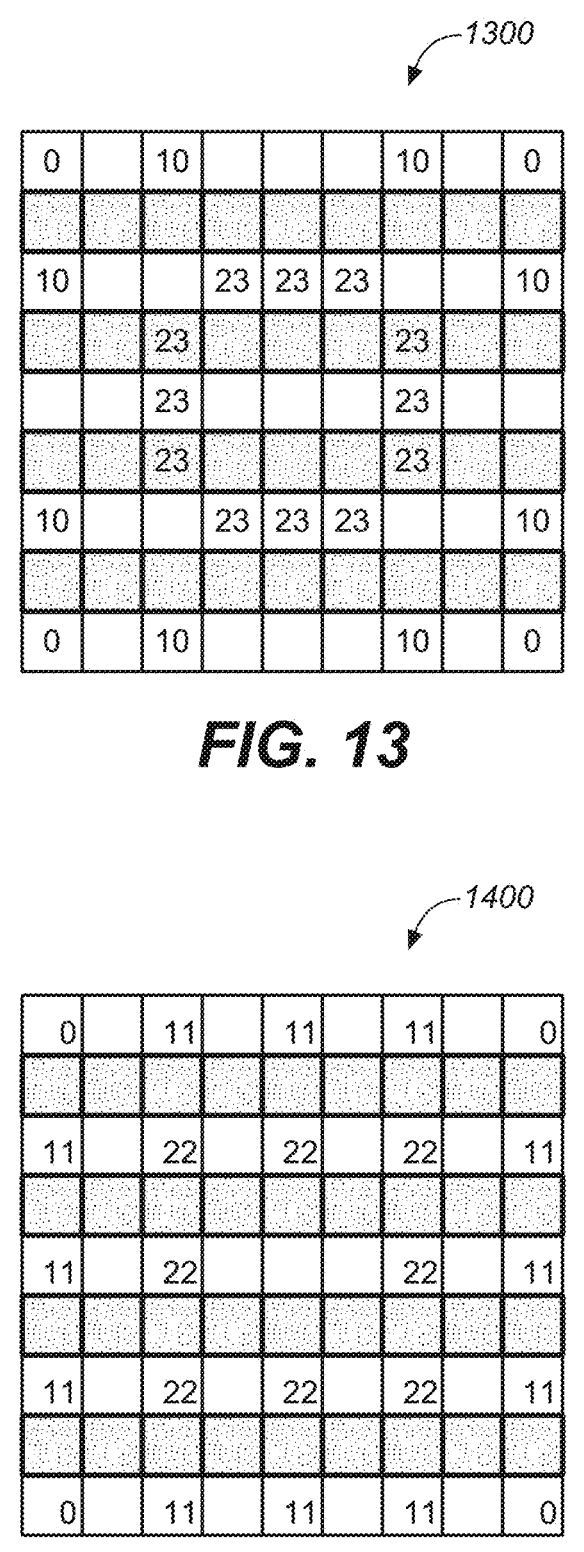

FIG. 13 illustrates an example phase delay pattern for ultrasonic signal transmission of a 9×9 ultrasonic transducer block 1300 of a two-dimensional array of ultrasonic transducers, according to some embodiments. As illustrated in FIG. 13, each number in the ultrasonic transducer array is equivalent to the nanosecond delay used during operation, and an empty element (e.g., no number) in the ultrasonic transducer block 1300 means that an ultrasonic transducer is not activated for signal transmission during operation. In various embodiments, ultrasonic wave amplitude can be the same or similar for each activated ultrasonic transducer, or can be selectively increased or decreased relative to other ultrasonic transducers. In the illustrated pattern, initial ultrasonic transducer activation is limited to corners of ultrasonic transducer block 1300, followed 10 nanoseconds later by a rough ring around the edges of ultrasonic transducer block 1300. After 23 nanoseconds, an interior ring of ultrasonic transducers is activated. Together, the twenty-four activated ultrasonic transducers generate an ultrasonic beam centered on the ultrasonic transducer block 1300. In other words, the phase delay pattern of ultrasonic transducer block 1300 is symmetric about the focal point where a high intensity beam contacts an object.

It should be appreciated that different ultrasonic transducers of ultrasonic transducer block 1300 may be activated for receipt of reflected ultrasonic signals. For example, the center 3×3 ultrasonic transducers of ultrasonic transducer block 1300 may be activated to receive the reflected ultrasonic signals. In another example, the ultrasonic transducers used to transmit the ultrasonic signal are also used to receive the reflected ultrasonic signal. In another example, the ultrasonic transducers used to receive the reflected ultrasonic signals include at least one of the ultrasonic transducers also used to transmit the ultrasonic signals.

FIG. 14 illustrates another example phase delay pattern for a 9×9 ultrasonic transducer block 1400, according to some embodiments. As illustrated in FIG. 14, the example phase delay pattern utilizes equidistant spacing of transmitting ultrasonic transducers. As illustrated in FIG. 13, each number in the ultrasonic transducer array is equivalent to the nanosecond delay used during operation, and an empty element (e.g., no number) in the ultrasonic transducer block 1400 means that an ultrasonic transducer is not activated for signal transmission during operation. In the illustrated embodiment, the initial ultrasonic transducer activation is limited to corners of ultrasonic transducer block 1400, followed 11 nanoseconds later by a rough ring around the edges of ultrasonic transducer block 1400. After 22 nanoseconds, an interior ring of ultrasonic transducers is activated. The illustrated embodiment utilizes equidistant spacing of the transmitting ultrasonic transducers to reduce issues with crosstalk and heating, wherein each activated ultrasonic transducers is surrounded by un-activated ultrasonic transducers. Together, the twenty-four activated ultrasonic transducers generate an ultrasonic beam centered on the ultrasonic transducer block 1400.

Figure 15:
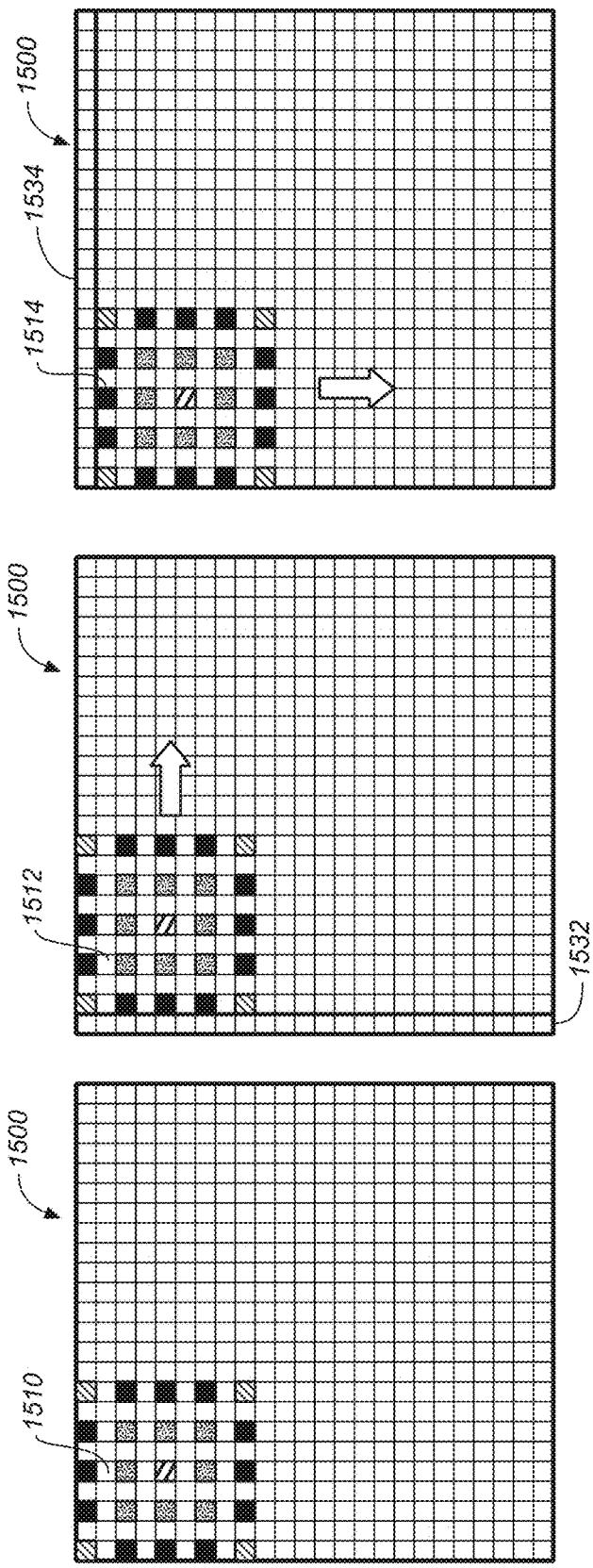
FIGS. 15A-C illustrate example transmitter blocks and receiver blocks for an array position in a two-dimensional array of ultrasonic transducers, according to some embodiments.

FIGS. 15A-C illustrate example transmitter blocks and receiver blocks for an array position in a two-dimensional array 1500 of ultrasonic transducers, according to some embodiments. In FIG. 15A, a four phase (indicated using different hatch patterns) activated phase delay pattern of ultrasonic transducers in a 9×9 array position 1510 is used to generate an ultrasonic beam.

In FIG. 15B, the 9×9 array position 1512 is moved rightward by a single column 1532 relative to array position 1510 of FIG. 15A, as indicated by the arrow. In other words, after activation at array position 1510 of two-dimensional array 1500, array position 1512 of two-dimensional array 1500 is activated, effectively sensing a pixel to the right of two-dimensional array 1500. In such a manner, multiple pixels associated with multiple array positions of the two-dimensional array 1500 can be sensed. Similarly, in FIG. 15C the 9×9 array position 1514 is moved downward by a single row 1534 relative to array position 1510 of FIG. 15A after activation of array position 1510 of two-dimensional array 1500, as indicated by the arrow. It should be appreciated that the 9×9 array position can move to different positions of two-dimensional array 1500 in any sequence. For example, an activation sequence may be defined as left to right for a row of ultrasonic transducers, then moving down one row when the end of a row is reached, and continuing to proceed in this manner until a desired number of pixels are sensed. In another example, the activation sequence may be defined as top to bottom for a column, and moving to another column once enough pixels have been sensed for a column. It should be appreciated that any activation sequence may be defined without limitation, including a random activation sequence. Moreover, it should be appreciated that any number of columns and/or rows can be skipped depending on a desired resolution.

In various embodiments, as an array position approaches an edge of two-dimensional array 1500, only those ultrasonic transducers that are available in two-dimensional array 1500 are activated. In other words, where a beam is being formed at a center of an array position, but the center is near or adjacent an edge of two-dimensional array 1500 such that at least one ultrasonic transducer of a phase delay pattern is not available (as the array position extends over an edge), then only those ultrasonic transducers that are available in two-dimensional array 1500 are activated. In various embodiments, the ultrasonic transducers that are not available (e.g., outside the edge of two-dimensional array 1500) are truncated from the activation pattern. For example, for a 9×9 ultrasonic transducer block, as the center ultrasonic transducer moves towards the edge such that the 9×9 ultrasonic transducer block extends over the edge of the two-dimensional array, rows, columns, or rows and columns (in the instance of corners) of ultrasonic transducers are truncated from the 9×9 ultrasonic transducer block. For instance, a 9×9 ultrasonic transducer block effectively becomes a 5×9 ultrasonic transducer block when the center ultrasonic transducer is along an edge of the two-dimensional array. Similarly, a 9×9 ultrasonic transducer block effectively becomes a 6×9 ultrasonic transducer block when the center ultrasonic transducer is one row or column from an edge of the two-dimensional array. In other embodiments, as an array position approaches an edge of two-dimensional array 1500, the beam is steered by using phase delay patterns that are asymmetric about the focal point, as described below in accordance with FIGS. 17A through 18B.

Figure 16:
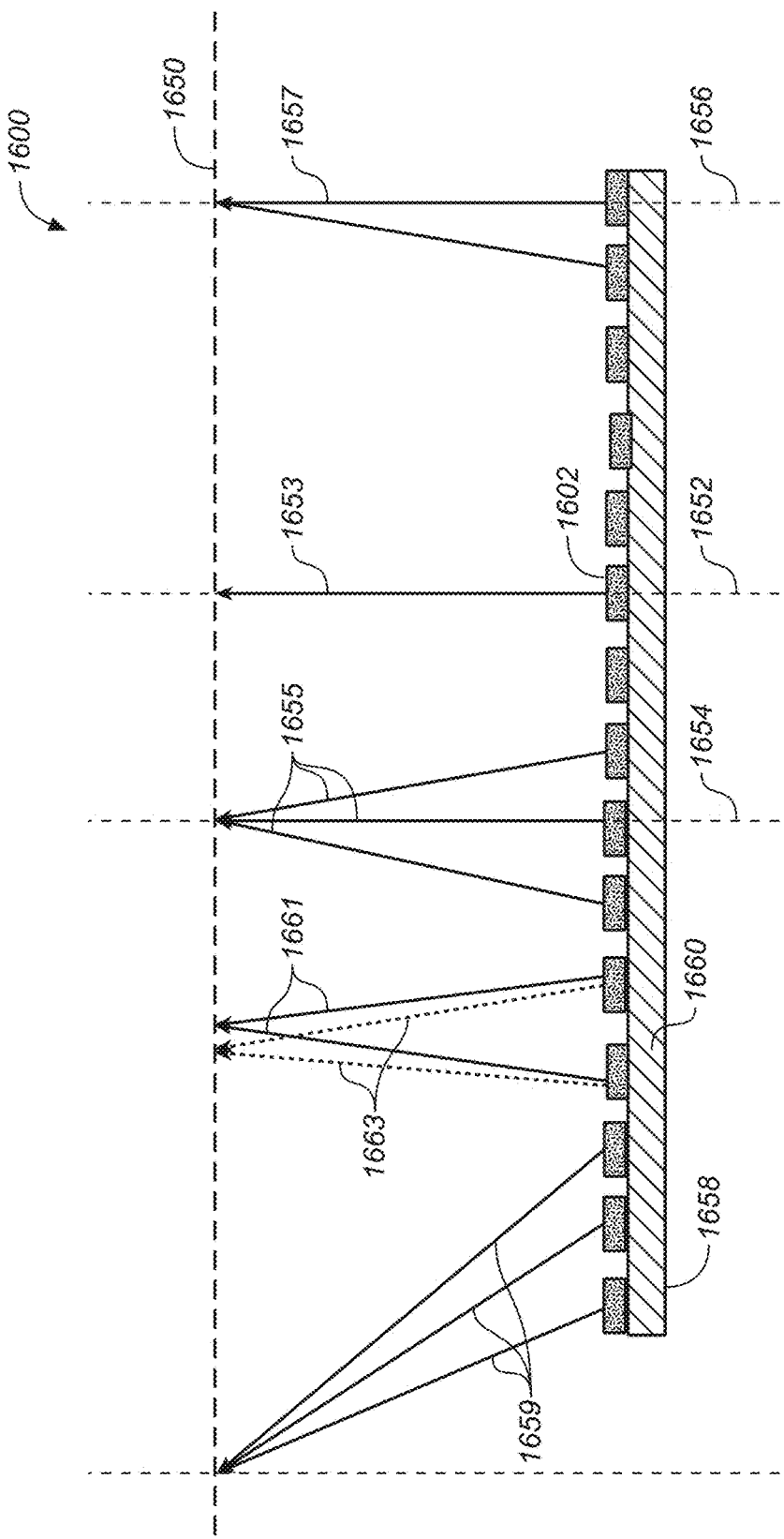
FIG. 16 illustrates an example ultrasonic transducer system with phase delayed transmission, according to some embodiments.

FIG. 16 illustrates an example ultrasonic transducer system 1600 with phase delayed transmission, according to some embodiments. FIG. 16 shows five different modes of ultrasonic beam transmission using an example one-dimensional, fifteen-element, ultrasonic transducer system 1600 having phase delayed inputs. As illustrated, ultrasonic transducers 1602 can be operated in various modes to provide ultrasonic beam spots focused along line 1650 (e.g., a top of a platen layer). In a first mode, a single ultrasonic transducer 1652 is operated to provide a single broad ultrasonic beam having a peak amplitude centered on arrow 1653. In a second mode, multiple ultrasonic transducers in a symmetrical pattern 1654 about the center ultrasonic transducer are sequentially triggered to emit ultrasonic waves at differing initial times. As illustrated, a center located transducer is triggered at a delayed time with respect to surrounding transducers (which are triggered simultaneously). The ultrasonic waves interfere with each other, resulting in a single high intensity beam 1655. In a third mode, for ultrasonic transducers 1656 located adjacent to or near an edge of the ultrasonic transducer system 1600, an asymmetrical triggering pattern can be used to produce beam 1657. In a fourth mode, asymmetrical triggering patterns for transducers 1658 can be used to steer an ultrasound beam to an off-center location 1659. A shown, the focused beam 1659 can be directed to a point above and outside boundaries of the ultrasonic transducer system 1600. In a fifth mode, the beam can be steered to focus at a series of discrete positions, with the beam spacing having a pitch less than, equal to, or greater than a pitch of the ultrasonic transducers. In FIG. 16, transducers 1660 are triggered at separate times to produce beam spots separated by a pitch less than that of the ultrasonic transducers (indicated respectively by solid lines directed to form beam spot 1661 and dotted lines to form beam spot 1663).

FIGS. 17A, 17B, 18A and 18B illustrate example phase delay patterns for a 5×5 ultrasonic transducer blocks, according to some embodiments. As illustrated in 17A, 17B, 18A and 18B, each number in the ultrasonic transducer array is equivalent to the nanosecond delay used during operation, and an empty element (e.g., no number) in the ultrasonic transducer blocks 1700, 1710, 1800 and 1810 means that an ultrasonic transducer is not activated for signal transmission during operation. In various embodiments, ultrasonic wave amplitude can be the same or similar for each activated ultrasonic transducer, or can be selectively increased or decreased relative to other ultrasonic transducers. It should be appreciated that the phase delay patterns described in accordance with FIGS. 17A, 17B, 18A and 18B are asymmetric about the focal point where a beam contacts an object.

Figure 17A:
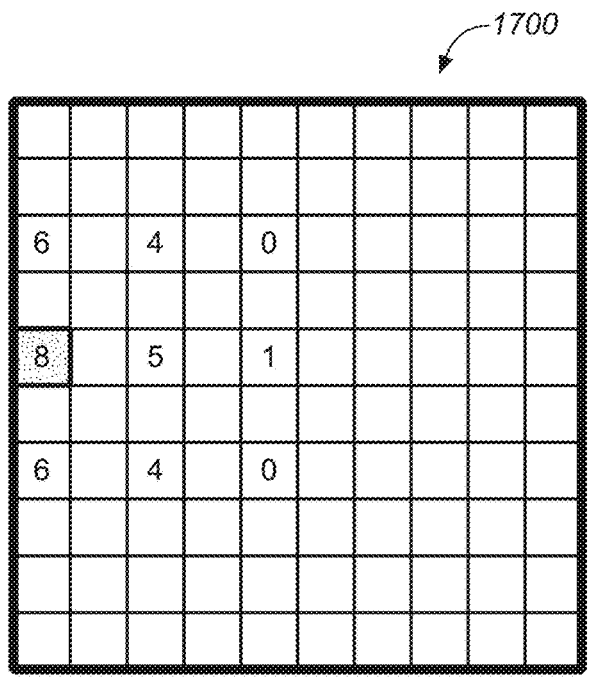
FIGS. 17A and 17B illustrate example phase delay patterns for a 5×5 ultrasonic transducer block, according to some embodiments.

FIG. 17A illustrates an example phase delay pattern for an array position of ultrasonic transducers at an edge of a two-dimensional array of ultrasonic transducers. Because ultrasonic transducer block 1700 is located at an edge, a symmetrical phase delay pattern about a center of ultrasonic transducer block 1700 is not available. In the illustrated pattern, initial ultrasonic transducer activation is limited to rightmost corners of the array, followed by selected action of ultrasonic transducers at 1, 4, 5, 6, and 8 nanosecond intervals. Together, the activated ultrasonic transducers generate an ultrasonic beam centered on the 8 nanosecond delayed ultrasonic transducer indicated in gray. In one embodiment, so as to reduce issues with crosstalk and heating, each activated ultrasonic transducer is equidistant from each other, being surrounded by un-activated ultrasonic transducer.

Figure 17B:
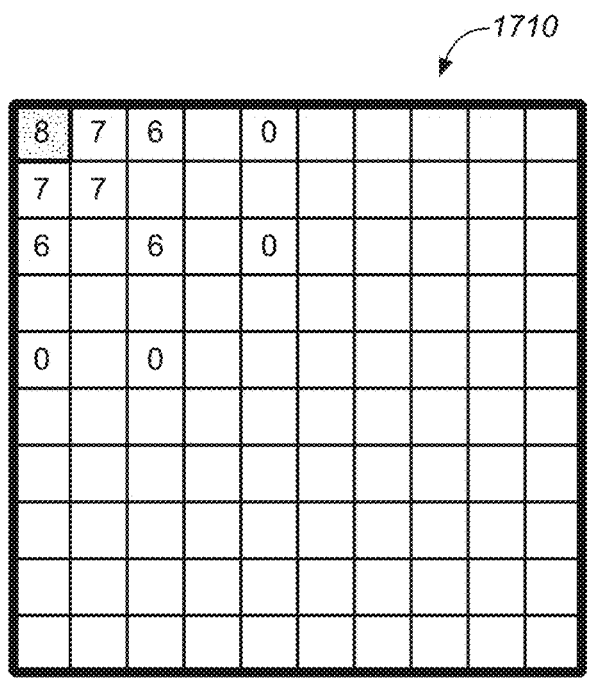

FIG. 17B illustrates an example phase delay pattern for a 5×5 ultrasonic transducer block 1710 in a corner of a two-dimensional array of ultrasonic transducers, with equidistant spacing of transmitting ultrasonic transducers. Like the phase delay timing pattern of FIG. 17A, the initial ultrasonic transducer activation is asymmetrical. Together, the activated ultrasonic transducers generate an ultrasonic beam centered on the 8 nanosecond delayed ultrasonic transducer indicated in gray. Adjacent ultrasonic transducers are activated in this embodiment to increase beam intensity.

Figure 18A:
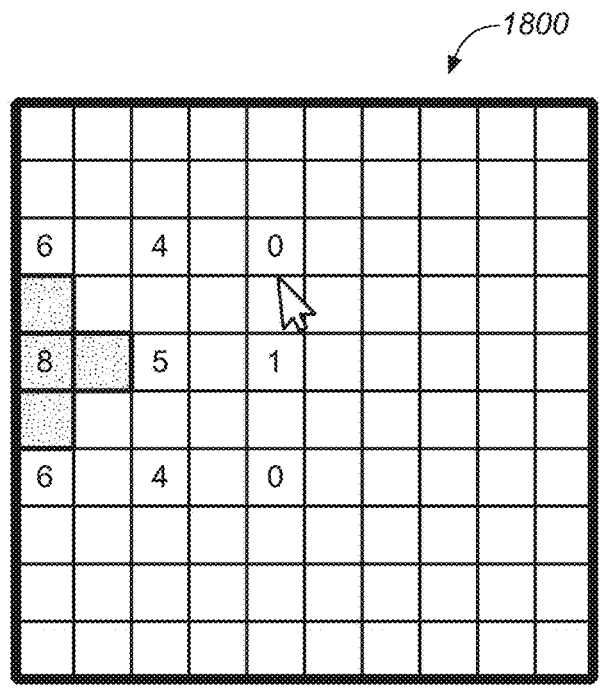
FIGS. 18A and 18B illustrate another example phase delay pattern for a 5×5 ultrasonic transducer block, according to some embodiments.

FIG. 18A illustrates an example phase delay pattern for an array position of ultrasonic transducers at an edge of a two-dimensional array of ultrasonic transducers. Because ultrasonic transducer block 1800 is located at an edge, a symmetrical phase delay pattern about a center of ultrasonic transducer block 1800 is not available. In the illustrated pattern, initial ultrasonic transducer activation is limited to rightmost corners of the array, followed by selected action of ultrasonic transducers at 1, 4, 5, 6, and 8 nanosecond intervals. Together, the activated ultrasonic transducers generate an ultrasonic beam centered on the 8 nanosecond delayed ultrasonic transducer indicated in gray. After beam transmit concludes, the gray (8 nanosecond) ultrasonic transducer is switched into a receive mode, along with those surrounding ultrasonic transducers indicated by spotted gray.

Figure 18B:
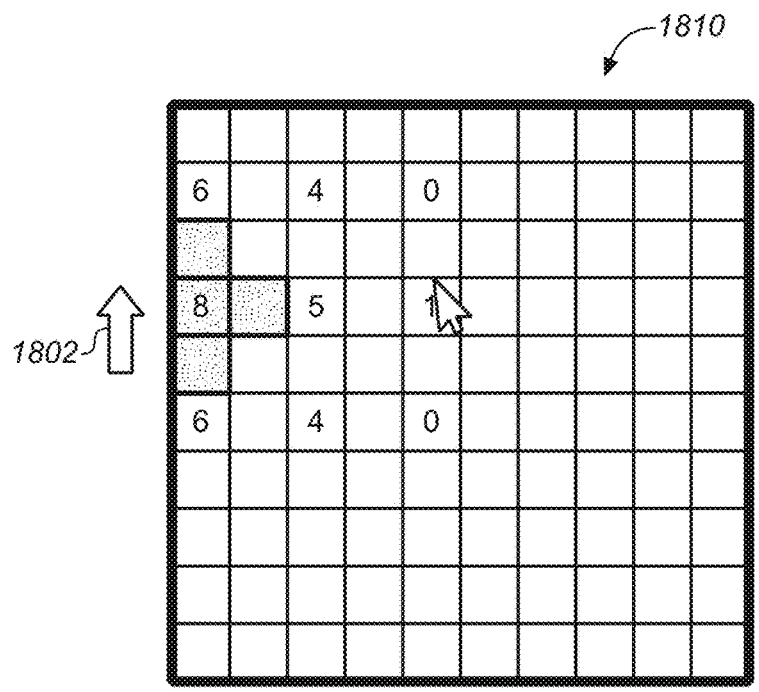

FIG. 18B illustrates ultrasonic transducer block 1810 is located at an edge of a two-dimensional array of ultrasonic transducers. This pattern is formed as ultrasonic transducer block 1800 is moved up a single row of ultrasonic transducers (indicated by arrow 1802) with respect to the phase delay pattern illustrated in FIG. 18A. As in FIG. 18A, the activated ultrasonic transducers together generate an ultrasonic beam centered on the 8 nanosecond delayed ultrasonic transducer indicated in gray. After beam transmit concludes, the gray (8 nanosecond) ultrasonic transducer is switched into a receive mode, along with those surrounding ultrasonic transducer indicated by spotted gray.

Sensor Array Configurations

In some embodiments, a two-dimensional array of individual ultrasonic transducers (e.g., PMUT device 100 of FIG. 1A or 100' of FIG. 1B) corresponds with a two-dimensional array of control electronics. This embodiment also applies to other types of MEMS arrays with integrated control electronics. This includes, but is not limited to, applications for inertial sensors, optical devices, display devices, pressure sensors, microphones, inkjet printers, and other applications of MEMS technology with integrated mixed-signal electronics for control. It should be appreciated that while the described embodiments may refer CMOS control elements for controlling MEMS devices and/or PMUT devices, that the described embodiments are not intended to be limited to such implementations.

Figure 19:
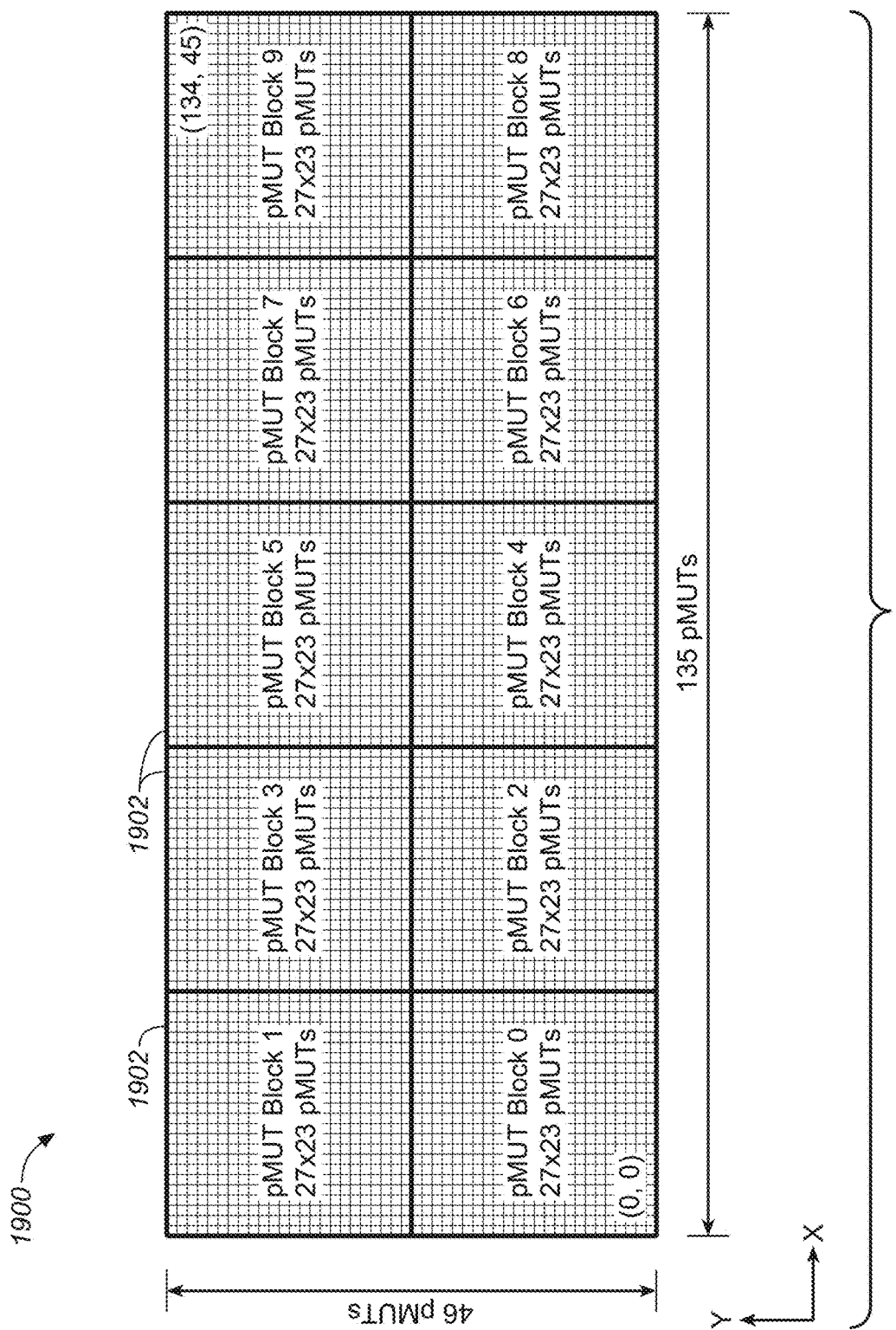
FIG. 19 illustrates an example ultrasonic sensor array, according to an embodiment.

FIG. 19 illustrates an example ultrasonic sensor array 1900, in accordance with an embodiment. The ultrasonic sensor array 1900 can be comprised of 135×46 ultrasonic transducers arranged into a rectangular grid as shown in FIG. 19. However, this is but one example of how the PMUT transducers may be arranged. To allow for consistent referencing of locations within the array 1900, the long dimension is defined herein as the X-axis, the short dimension as the Y-axis, and bottom left corner as the origin. As such (using units of ultrasonic transducers as the coordinate system), the ultrasonic transducer at the bottom left corner is at position (0, 0) whereas the ultrasonic transducer at the top right corner is at position (134, 45).

In order to capture fingerprint images as quickly as possible, it is desired to simultaneously image as many pixels as possible. This is limited in practice by power consumption, number of independent receiver (Rx) channels (slices) and analog-to-digital converters (ADCs), and spacing requirements between active ultrasonic transducers so as to avoid interference. Accordingly, the capability to simultaneously capture several image pixels, e.g., ten image pixels, may be implemented. It will be appreciated that fewer than ten or more than ten image pixels may be captured simultaneously. In an embodiment, this involves ten independent, parallel receiver channels and ADCs. Each of these receiver channels and ADCs is associated with a subset of the overall sensor array as shown in FIG. 19. In this example, the ten "PMUT Blocks" 1902 (also referred to as "ADC areas" or "array sub-blocks") are 27×23 PMUTs in size. Thus, the ultrasonic sensor may comprise a number, here, ten, of blocks of ultrasonic transducers.

The ten receive channels and ADCs are placed directly above or below each associated array sub-block. During a typical imaging operation, each array sub-block 1902 is configured and operated identically such that ten image pixels are captured simultaneously, one each from identical locations within each array sub-block. Beamforming patterns (e.g., the phase delay patterns illustrated in FIGS. 13, 14, 17A, 17B, 18A, and 18B) representing transmit (Tx) phases are applied to selected PMUTs within each of the array sub-blocks 1902. The transmit phases are arranged to focus ultrasonic energy (e.g., onto the area just above the center of each of the patterns)—a process called transmit beamforming. The ultrasonic signal that is reflected back to the ultrasonic transducers at an imaging point of each beamforming pattern is converted to an electrical signal and routed to the associated receive channel and ADC for sensing and storage. The overall process of transmitting an ultrasonic signal, waiting for it to propagate to the target and back, and capturing the reflected ultrasonic signal is referred to herein as a "TxRx Period".

Imaging over the entire sensor area is accomplished by stepping the transmit beamforming patterns over the entire ultrasonic transducer array, transmitting and receiving at each location corresponding to an image pixel. Because ten image pixels are captured simultaneously during each TxRx Period (one image pixel from identical locations within each array sub-block 1902), it takes just as much time to capture the image pixels for the entire array as it would to capture the image pixels for only a single array sub-block.

There may be times when scanning is required over only a sub-set of the array sub-blocks. In such cases, it is possible to disable transmitting or receiving signals within designated array sub-blocks to save the power that would otherwise be used in transmitting or receiving within those sub-blocks. In one embodiment, the array is configured (e.g., via a register) to enable transmitting in all ten array sub-blocks. In other embodiments, the array is configured to disable transmit within selected vertical pairs of array sub-blocks. For example, setting bits of a transmit register to 1_0111 keeps array sub-blocks 0-5, 8, and 9 active for transmit but shuts off transmit in array sub-blocks 6 and 7. Similarly, the array is configured (e.g., via a register) to enable receiving in all ten array sub-blocks. However, selected bits of this register can be set to "0" to disable receive within selected array sub-blocks. For example, setting bits of a receive register to 01_1011_1111 enables all the array sub-blocks to receive normally except for array sub-blocks 6 and 9 (e.g., all receive and ADC circuitry associated with array blocks 6 and 9 are powered down).

As described above with reference to FIGS. 11 through 18B, embodiments described herein provide for the use of transmit (TX) beamforming to focus ultrasonic energy onto a desired location above a two-dimensional array of ultrasonic transducer. Transmit beamforming acts to counteract diffraction and attenuation of the ultrasound signals as they propagate up from the transmitting ultrasonic transducers (e.g., PMUTs) through the material stack to the finger and then back down through the material stack to the receiving ultrasonic transducer(s). Transmit beamforming allows for ultrasonic fingerprint sensors that provide significantly better image resolution and signal-to-noise ratio than other ultrasonic fingerprint sensors that do not use this technique.

In accordance with various embodiments, the performance of transmit beamforming described herein is reliant on generation, distribution, and selective transmission of multiple transmit signals with controllable relative phase (delay) and precisely timed reception of reflected ultrasonic signals from selected receive ultrasonic transducers. Embodiments described herein provide for configuration of transmit beamforming patterns for use in imaging on a two-dimensional array of ultrasonic transducers.

Figure 20:
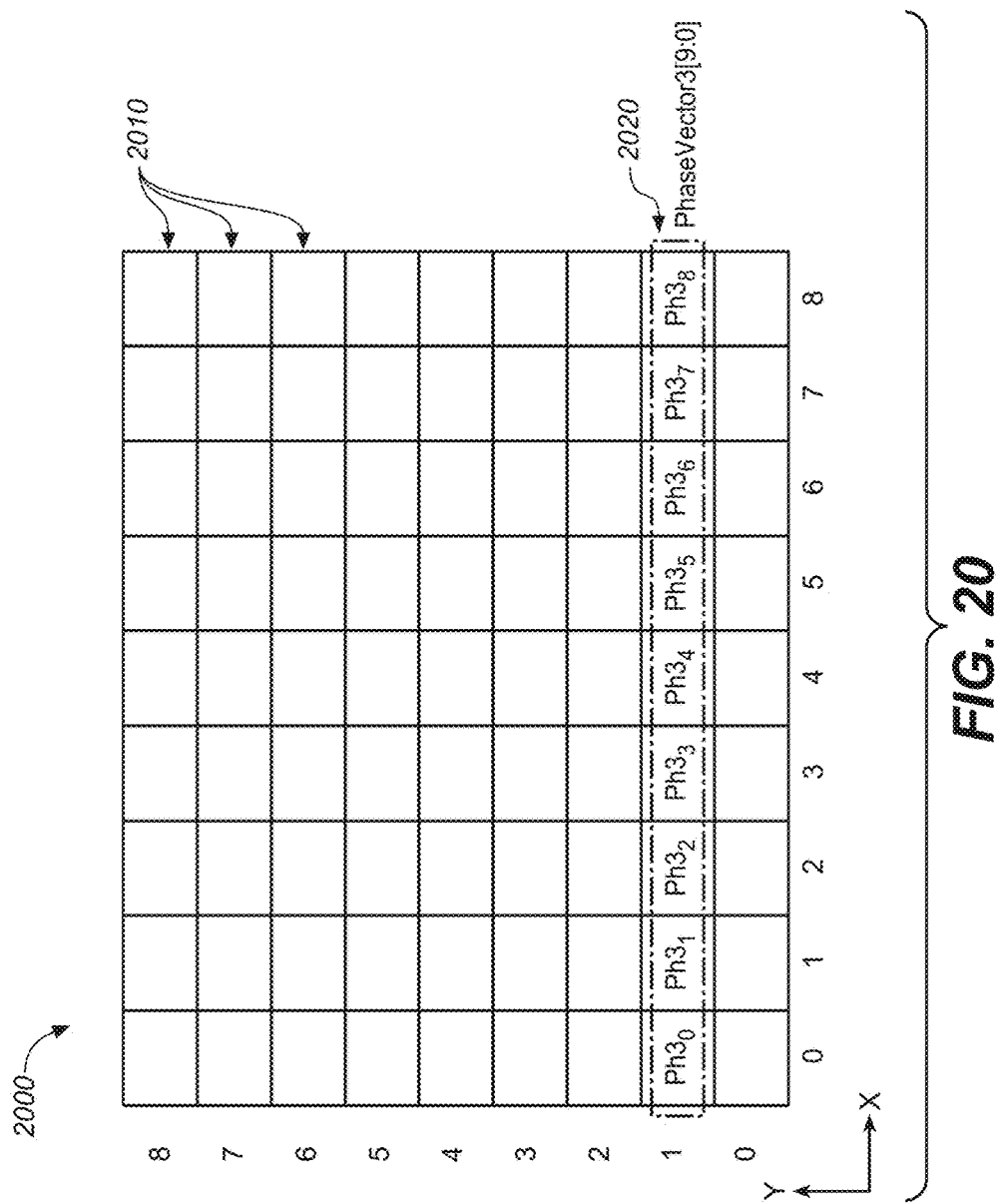
FIG. 20 illustrates an example beamforming space, according to an embodiment.

FIG. 20 illustrates an example beamforming space 2000, in accordance with various embodiments. A beamforming space is used to define registers for configuring an arbitrary sub-set of ultrasonic transducers of the array of ultrasonic transducers for transmitting and/or receiving ultrasonic signals. As illustrated, beamforming space 2000 corresponds to a 9×9 subset of ultrasonic transducers of the array of ultrasonic transducers. However, it should be appreciated that any subset of ultrasonic transducers may be used, and that the described embodiments are not limited to the illustrated example. For example, a beamforming space may correspond to a 5×5 subset of ultrasonic transducers, an 8×8 subset of ultrasonic transducers, a 5×9 subset of ultrasonic transducers, a 5×12 subset of ultrasonic transducers, or any other subset of ultrasonic transducers. In various embodiments, digital and analog hardware (e.g., an array engine) of the ultrasonic sensor that includes the array of ultrasonic transducers uses the register settings associated with the beamforming space to apply the designated beamforming space configuration to the actual array of ultrasonic transducer.

In various embodiments, a beamforming pattern is defined in beamforming space 2000 that is applied to the two-dimensional array of ultrasonic transducers. Beamforming space 2000 includes elements 2010, where each element 2010 corresponds to an ultrasonic transducer of the two-dimensional array of ultrasonic transducers. An element defines a transmit signal that is applied to the corresponding ultrasonic transducer during a transmit operation. The beamforming pattern identifies which ultrasonic transducers within beamforming space 2000 are activated during a transmit operation of the two-dimensional array of ultrasonic transducers. At least some of the ultrasonic transducers that are activated are phase delayed with respect to other ultrasonic transducers that are activated. It should be appreciated that not all ultrasonic transducers need to be activated during a transmit operation.

In accordance with various embodiments, rows or columns of beamforming space are configured to receive phase vectors, where a phase vector specifies the desired transmit signal to be transmitted by each ultrasonic transducer within row or column of the beamforming space. For ease of description, this specification refers to rows of the beamforming space. However, it should be appreciated that in various embodiments columns may be interchangeable with rows, and that the described embodiments are not limited to rows of a beamforming space. As illustrated, phase vector 2020 is a 9×1 row of beamforming space 2000.

In accordance with various embodiments, an ultrasonic sensor is configured to support a set number of transmit signals and a set number of phase vectors. In one embodiment, the ultrasonic sensor is configured to accommodate up to four transmit signals and up to five independent phase vectors to be arbitrarily applied to the nine rows within beamforming space 2000. The elements that make up the phase vectors are chosen from a list of four possible transmit signals designated by 'A', 'B', 'C', and 'D'. The first three transmit signals ('A', 'B', and 'C') represent actual transmit signals which are identical except for their phase (delay) relative to one another. The fourth signal 'D' is a null phase (e.g., no signal/null signal/ground (GND)).

In one embodiment, the notation for the five phase vectors is:

PhaseVector0[8:0]=[Ph0$_8$,Ph0$_7$,Ph0$_6$,Ph0$_5$,Ph0$_4$,Ph0$_3$, Ph0$_2$,Ph0$_1$,Ph0$_0$]

PhaseVector1[8:0]=[Ph1$_8$,Ph1$_7$,Ph1$_6$,Ph1$_5$,Ph1$_4$,Ph1$_3$, Ph1$_1$,Ph1$_1$,Ph1$_0$]

PhaseVector2[8:0]=[Ph2$_8$,Ph2$_7$,Ph2$_6$,Ph2$_5$,Ph2$_4$,Ph2$_3$, Ph2$_2$,Ph2$_1$,Ph2$_0$]

PhaseVector3[8:0]=[Ph3$_8$,Ph3$_7$,Ph3$_6$,Ph3$_5$,Ph3$_4$,Ph3$_3$, Ph3$_2$,Ph3$_1$,Ph3$_0$]

PhaseVector4[8:0]=[Ph4$_8$,Ph4$_7$,Ph4$_6$,Ph4$_5$,Ph4$_4$,Ph4$_3$, Ph4$_2$,Ph4$_1$,Ph4$_0$]

The subscripts in the vector notations above refer to the x-axis position (column index) of beamforming space 2000. For example, FIG. 20 illustrates how PhaseVector3 is applied to the second row (Row1) of beamforming space 2000.

Figure 21A:
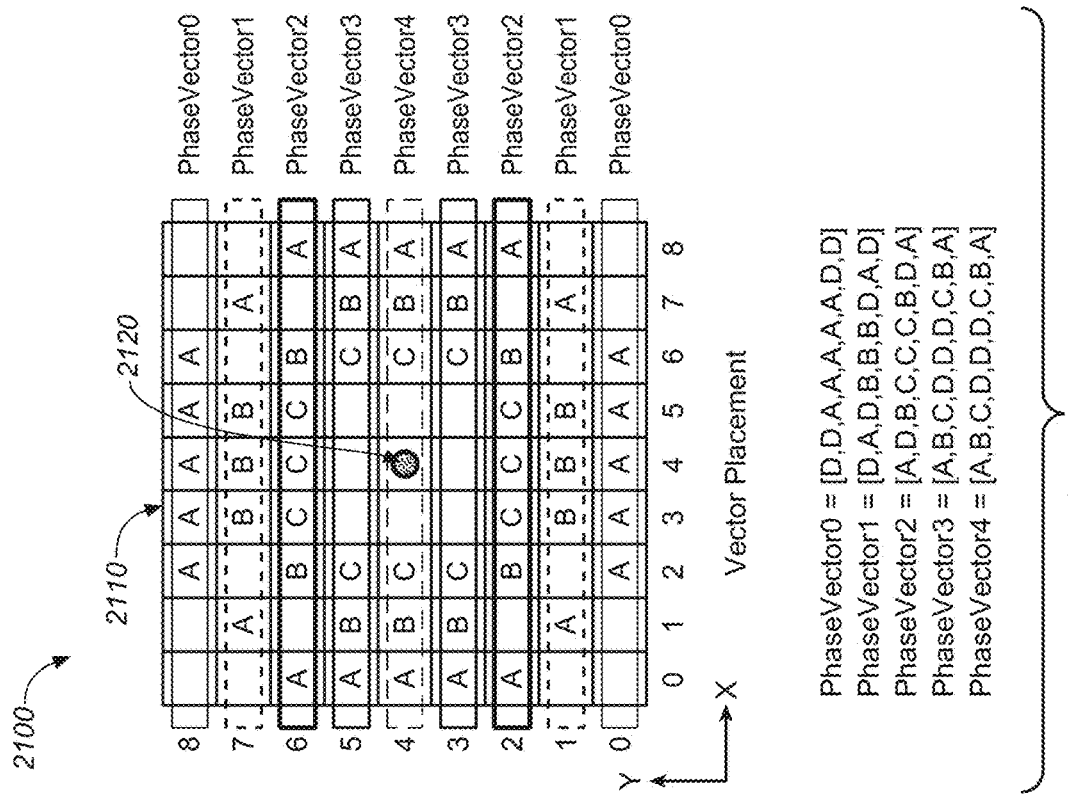
FIG. 21A illustrates an example beamforming pattern within a beamforming space, according to an embodiment.
Figure 21B:
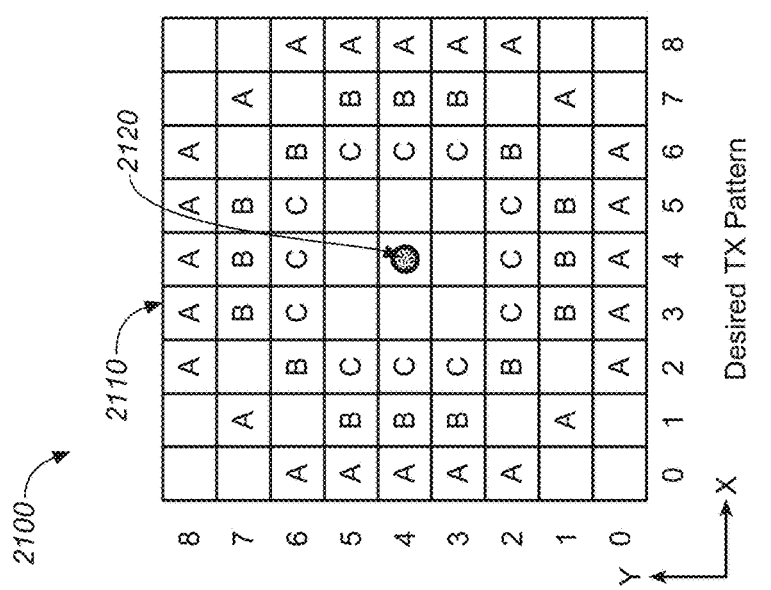
FIG. 21B illustrates an example phase vector placement within beamforming space to provide a beamforming pattern, according to an embodiment.

FIG. 21A illustrates an example beamforming pattern 2110 within a beamforming space 2100 and FIG. 21B illustrates an example phase vector placement within beamforming space 2100 to provide the beamforming pattern 2110, in accordance with an embodiment.

FIG. 21A illustrates a 9×9 beamforming space 2100, where elements that make up the phase vectors are chosen from a list of four possible transmit signals designated by 'A', 'B', 'C', and 'D'. The first three transmit signals ('A', 'B', and 'C') represent actual transmit signals which are identical except for their phase (delay) relative to one another. The fourth signal 'D' is a null phase (e.g., no signal/null signal/ground (GND)). An empty element of beamforming space 2100 includes no signal (e.g., signal 'D'). As illustrated, the transmit signals of beamforming pattern 2110 are symmetric about the center element (element 4, 4 of beamforming space 2100). Beamforming pattern 2110 operates to form a beam at imaging point 2120 located over the center element of beamforming space 2100.

FIG. 21B illustrates phase vector placement within beamforming space 2100 to generate beamforming pattern 2110. The ultrasonic sensor is configured to accommodate up to five distinct phase vectors for placement within beamforming space 2100. FIG. 21B illustrates how the phase vectors are selectively applied to various rows in the beamforming space to achieve the desired transmit beamforming pattern 2110. As illustrated, the notation for the five phase vectors is:

PhaseVector0=[D,D,A,A,A,A,A,D,D]

PhaseVector1=[D,A,D,B,B,B,D,A,D]

PhaseVector2=[A,D,B,C,C,C,B,D,A]

PhaseVector3=[A,B,C,D,D,D,C,B,A]

PhaseVector4=[A,B,C,D,D,D,C,B,A]

Note that an empty element of FIG. 21B includes signal 'D', which is a null phase signal (e.g., no signal). Moreover, note that in the illustrated embodiment, PhaseVector3 and PhaseVector4 are identical. It should be appreciated that PhaseVector3 and PhaseVector4 are interchangeable as they include the same element signals. As such, beamforming pattern 2110 may be generated using only four phase vectors.

The phase vectors are arranged within beamforming space 2100 such that each row (rows 0 through 8 as illustrated) is populated with one 9×1 phase vector. As illustrated, rows 0 and 8 are populated with PhaseVector0, rows 1 and 7 are populated with PhaseVector1, rows 2 and 6 are populated with PhaseVector2, rows 3 and 5 are populated with PhaseVector3, and row 4 is populated with PhaseVector4. Accordingly, embodiments described herein provide for creation and implementation of beamforming patterns within a beamforming space using a limited number of transmission signals and a limited number of phase vectors.

As illustrated, transmit beamforming pattern 2110 is XY-symmetrical around the center of the central element corresponding to a center ultrasonic transducer of beamforming space 2100 at (4, 4). As such, transmit beamforming pattern 2110 will focus ultrasonic energy directly above the center ultrasonic transducer (illustrated as an imaging point 2120) in beamforming space 2100.

The resulting ultrasound reflection can then be received by either the central ultrasonic transducer at (4, 4) or by the parallel combination of the nine central ultrasonic transducers at (3, 3), (4, 3), (5, 3), (3, 4), (4, 4), (5, 4), (3, 5), (4, 5), and (5, 5). In one embodiment, an ultrasonic transducer is not able to be used for both transmit and receive operations within the same pixel capture. In such an embodiment, transmit beamforming pattern 2110 is configured to select the null phase 'D' for transmit by the ultrasonic transducers that will be used for receive operation. In other embodiments (not illustrated), an ultrasonic transducer is able to be used for both transmit and receive operations within the same pixel capture FIG. 22A illustrates an example beamforming pattern 2210 within a beamforming space 2200 and FIG. 22B illustrates an example phase vector placement within beamforming space 2200 to provide the beamforming pattern 2210, in accordance with another embodiment.

FIG. 22A illustrates a 9×9 beamforming space 2200, where elements that make up the phase vectors are chosen from a list of four possible transmit signals designated by 'A', 'B', C', and 'D'. The first three transmit signals ('A', 'B', and 'C') represent actual transmit signals which are identical except for their phase (delay) relative to one another. The fourth signal 'D' is a null phase (e.g., no signal/null signal/ground (GND)). An empty element of beamforming space 2200 includes no signal (e.g., signal 'D').

FIG. 22B illustrates phase vector placement within beamforming space 2200 to generate beamforming pattern 2210. The ultrasonic sensor is configured to accommodate up to five distinct phase vectors for placement within beamforming space 2200. FIG. 22B illustrates how the phase vectors are selectively applied to various rows in the beamforming space 2200 to achieve the desired transmit beamforming pattern 2210. As illustrated, the notation for the five phase vectors is:

PhaseVector0=[D,D,A,A,A,A,D,D,D]

PhaseVector1=[D,A,B,B,B,B,A,D,D]

PhaseVector2=[A,B,D,C,C,D,B,A,D]

PhaseVector3=[A,B,C,D,D,C,B,A,D]

PhaseVector4=[D,D,D,D,D,D,D,D,D]

Note that an empty element of FIG. 22B includes signal 'D', which is a null phase signal (e.g., no signal).

The phase vectors are arranged within beamforming space 2200 such that each row (rows 0 through 8 as illustrated) is populated with one 9×1 phase vector. As illustrated, rows 0 and 7 are populated with PhaseVector0, rows 1 and 6 are populated with PhaseVector1, rows 2 and 5 are populated with PhaseVector2, rows 3 and 4 are populated with PhaseVector3, and row 8 is populated with PhaseVector4. Accordingly, embodiments described herein provide for creation and implementation of beamforming patterns within a beamforming space using a limited number of transmission signals and a limited number of phase vectors.

As illustrated, beamforming pattern 2210 focuses ultrasonic energy onto the bottom right corner of the ultrasonic transducer at (4, 4), illustrated as imaging point 2220. The resulting ultrasound reflection can then be received by the parallel combination of the four ultrasonic transducers at (4, 3), (5, 3), (4, 4), and (5, 4), illustrated as emitting no signal during a transmit operation. Note also that the entire first column (column 0) and the entire top row (row 8) of the beamforming space 2200 are designated to receive the null phase 'D'. In other words, only the bottom right 8×8 sub-area of the 9×9 beamforming space 2200 is used for beamforming pattern 2210. The illustrated embodiment shows the configuration of transmit beamforming pattern 2210 that is XY-symmetrical about imaging point 2220 at the lower right corner of the ultrasonic transducer at (4, 4). In one embodiment, the 8×8 sub-set at the lower right of beamforming space 2200 is used when creating a transmit beamforming pattern to image at the corners between four adjacent ultrasonic transducers.

The various embodiments described above provide for defining a beamforming pattern of a beamforming space. In some embodiments, phase vectors are used to populate rows of the beamforming space. It should be appreciated that these concepts can be adapted to any type and size of beamforming space, in which ultrasonic transducers are activated to emit ultrasonic signals for imaging a pixel.

In some embodiments, a beamforming space is applicable for specifying which ultrasonic transducers will be activated to receive the ultrasonic signal that reflects back onto the ultrasonic transducer array after the ultrasonic transducers selected for transmit beamforming have transmitted their outgoing ultrasonic pulses. In one embodiment, this is accomplished by driving a receive select signal through at least one row of ultrasonic transducers and a receive select signal through at least one column of ultrasonic transducers in the beamforming space. An ultrasonic transducer is activated to receive whenever both its receive select signals are activated (e.g., set to a logic level '1'). In this way, for example, with reference to FIGS. 22A and 22B, the four ultrasonic transducers at (4, 3), (5, 3), (4, 4), and (5, 4) are activated to receive by setting Row 3, Row 4, Column 4, and Column 5 to receive (e.g., rxRowSel3, rxRowSel4, rxColSel4, and rxColSel5 are set to logic level '1' and the remaining row rxRowSelY lines and column rxColSelX lines are set to logic level '0').

Figure 23:
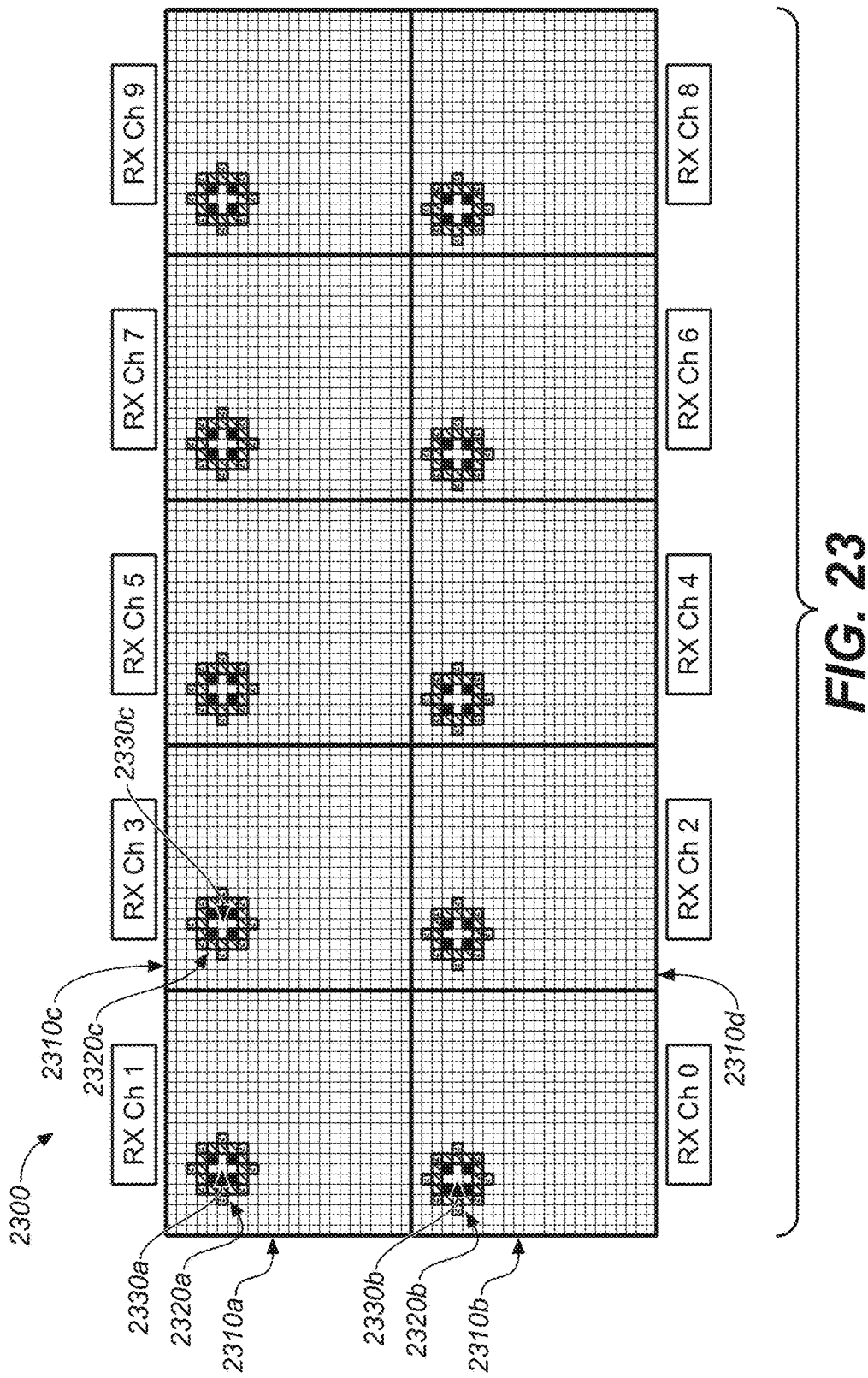
FIG. 23 illustrates example simultaneous operation of transmitter blocks for a multiple array positions in a two-dimensional array of ultrasonic transducers, according to an embodiment.

FIG. 23 illustrates example simultaneous operation of transmitter blocks for a multiple array positions in a two-dimensional array 2300 of ultrasonic transducers, according to some embodiments. As described above, a 9×9 beamforming space can be used to define a beamforming pattern for an ultrasonic sensor array. In the illustrated example, two-dimensional array 2300 is 48×144 ultrasonic transducers, separated into twelve identical 24×24 blocks 2310 (four of which are illustrated as 2310a-d). In one embodiment, a mux-based transmission/receive (Tx/Rx) timing control method can be used to activate the appropriate ultrasonic transducers in each block, based on the beamforming pattern. When a sequence of activation to generate an ultrasound beam and sensing reflected echoes is completed, the beamforming pattern (e.g., beamforming patterns 2320a, 2320b, and 2320c) is moved rightward or leftward, or upward and downward, with respect to the two-dimensional array 2300 of ultrasonic transducers, and the sequence is repeated until all (or a specified amount) of pixels have been imaged. As the beamforming pattern moves, so does the receive pattern of ultrasonic transducers activated during a receive operation (e.g., receive patterns 2330a, 2330b, and 2330c.

As previously described, it should be appreciated that any type of activation sequence may be used (e.g., side-to-side, top-to-bottom, random, another predetermined order, row and/or column skipping, etc.) Moreover, it should be appreciated that FIG. 23 illustrates a phase delay pattern that is symmetric about a focal point of the transmitting pixels. As previously described, it is understood that different phase delay patterns may be used as a focal point approaches or is adjacent to an edge and/or corner of the two-dimensional array. For example, a phase delay pattern similar to that illustrated in FIG. 17A may be used as a focal point approaches or is adjacent to an edge of the two-dimensional array and a phase delay pattern similar to that illustrated in FIG. 17B may be used as a focal point approaches or is adjacent to corner of the two-dimensional array. In various embodiments, the ultrasonic transducers that are not available (e.g., outside the edge of a two-dimensional array 2300) are truncated from the activation pattern. For example, for a 9×9 array position, as the center ultrasonic transducer moves towards an edge such that the 9×9 array position extends over the edge of the two-dimensional array, rows, columns, or rows and columns (in the instance of corners) of ultrasonic transducers are truncated from the 9×9 array position. For instance, a 9×9 array position effectively becomes a 5×9 array position when the center ultrasonic transducer is along an edge of the two-dimensional array. Similarly, a 9×9 ultrasonic transducer block effectively becomes a 6×9 array position when the center ultrasonic transducer is one row or column from an edge of the two-dimensional array.

Moreover, it should be appreciated that in accordance with various embodiments, multiple phase delay patterns for sensing multiple pixels within an array position can be used for an array position. In other words, multiple pixels can be sensed within a single array position, thereby improving the resolution of a sensed image.

Once a beamforming space has been defined to designate which ultrasonic transducers in the beamforming space will be used for transmission of ultrasonic signals (e.g., the beamforming pattern), for receipt of reflected ultrasonic signals (e.g., the receive pattern), or for nothing (remain inactive), the ultrasonic sensor programs the transmit beamforming pattern and receive beamforming pattern into at least one location within the ultrasonic transducer array.

In one embodiment, an array controller (e.g., an array engine, array control logic) and array control shift register logic of the ultrasonic sensor programs this transmit beamforming pattern and receive pattern onto a plurality of locations within the ultrasonic transducer array. For example, with reference to FIG. 23, the beamforming pattern is programmed at corresponding locations within each of the ten ultrasonic array sub-blocks so that up to ten image pixels can be captured in each transmit/received (TX/RX) operation, one pixel from each of the ten ultrasonic array sub-blocks. Imaging over the entire sensor area is then accomplished by stepping the beamforming patterns over the entire ultrasonic transducer array, transmitting and receiving at each step to capture a corresponding image pixel.

As the TX/RX beamforming patterns and receive patterns are stepped across the ultrasonic array, the patterns will sometimes overlap multiple array sub-blocks (e.g., two or four ultrasonic array sub-blocks). For example, a 9×9 beamforming pattern might have its upper left 6×6 ultrasonic transducers in ultrasonic array sub-block 2310a, its lower left 6×3 ultrasonic transducers in array sub-block 2310b, its upper right 3×6 ultrasonic transducers in array sub-block 2310c, and its lower right 3×3 ultrasonic transducers in array sub-block 2310d. In these instances, it is important to understand which receive slice (e.g., RX channel) will process the receive signals from each of the beamforming patterns.

In accordance with various embodiments, the array circuitry decides which receive slice processes the receive signals according to the following examples:

- When a receive pattern is programmed for 3×3 ultrasonic transducers within the 9×9 beamforming space, the location of the ultrasonic transducer at the center of the 3×3 receive pattern determines the receive slice that will be used to process the receive signals.
- When a receive pattern is programmed for 2×2 ultrasonic transducers within the 9×9 beamforming space, the location of the ultrasonic transducer at the upper left of the 2×2 receive pattern determines the receive slice that will be used to process the receive signals.
- When a receive pattern is programmed for a single ultrasonic transducer within the 9×9 beamforming space, the location of that ultrasonic transducer determines the receive slice that will be used to process the receive signals.

It should be appreciated that other designations for determining which receive slice processes a receive signal is possible, and that possible designations are not limited to the above examples.

Various embodiments provide digital hardware of an ultrasonic sensor that uses registers that specify the beamforming space configuration along with an array controller (e.g., a state machine), also referred to herein as an "array engine," in the digital route of the ultrasonic sensor digital to configure and control the physical ultrasonic transducer array.

Figure 24:
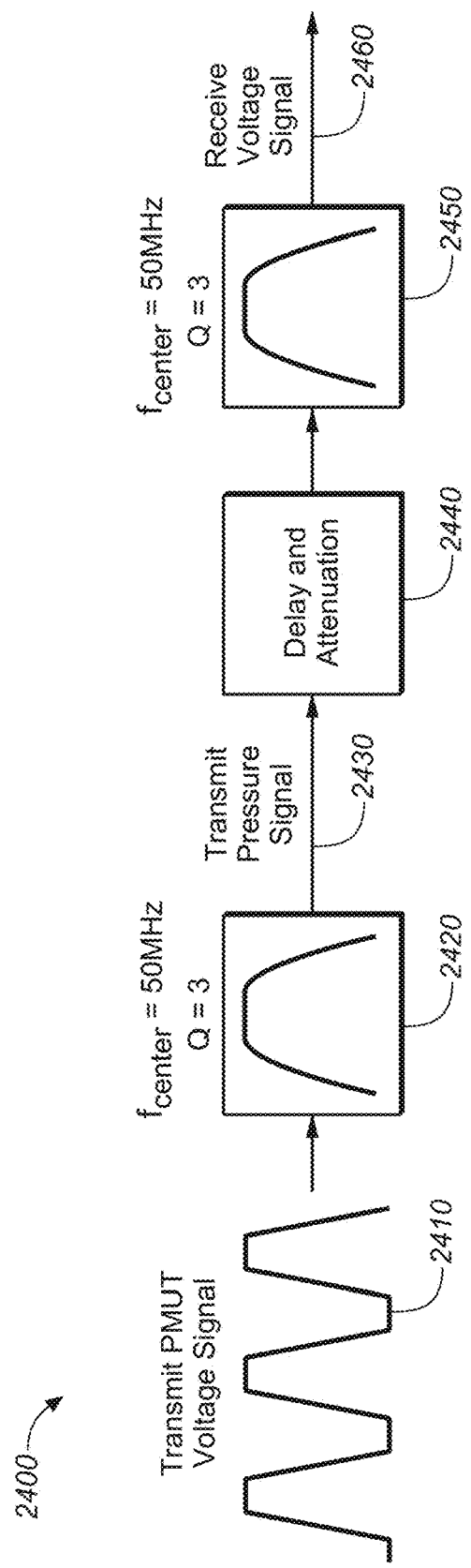
FIG. 24 illustrates an example operational model of a transmit signal to a receive signal of a two-dimensional array of ultrasonic transducers, according to some embodiments.

FIG. 24 illustrates an example operational model 2400 of a transmit signal to a receive signal of a two-dimensional array of ultrasonic transducers, according to some embodiments. FIG. 24 shows an operational model 2400 from voltage transmit signal into a PMUT array 2410 and ending with voltage receive signal from the PMUT array. Three cycles of the voltage waveform are bandpass filtered by the PMUT 2420, sent out as an ultrasonic pressure signal 2430 that is attenuated and delayed by interaction with objects and materials in an ultrasonic signal path 2440, and then bandpass filtered by the PMUT array 2450 to create the final receive signal 2460. In the illustrated example, the PMUT bandpass filter response 2420 and 2450 is assumed to be centered at 50 MHz with Q of approximately 3, although other values may be used.

Figure 25:
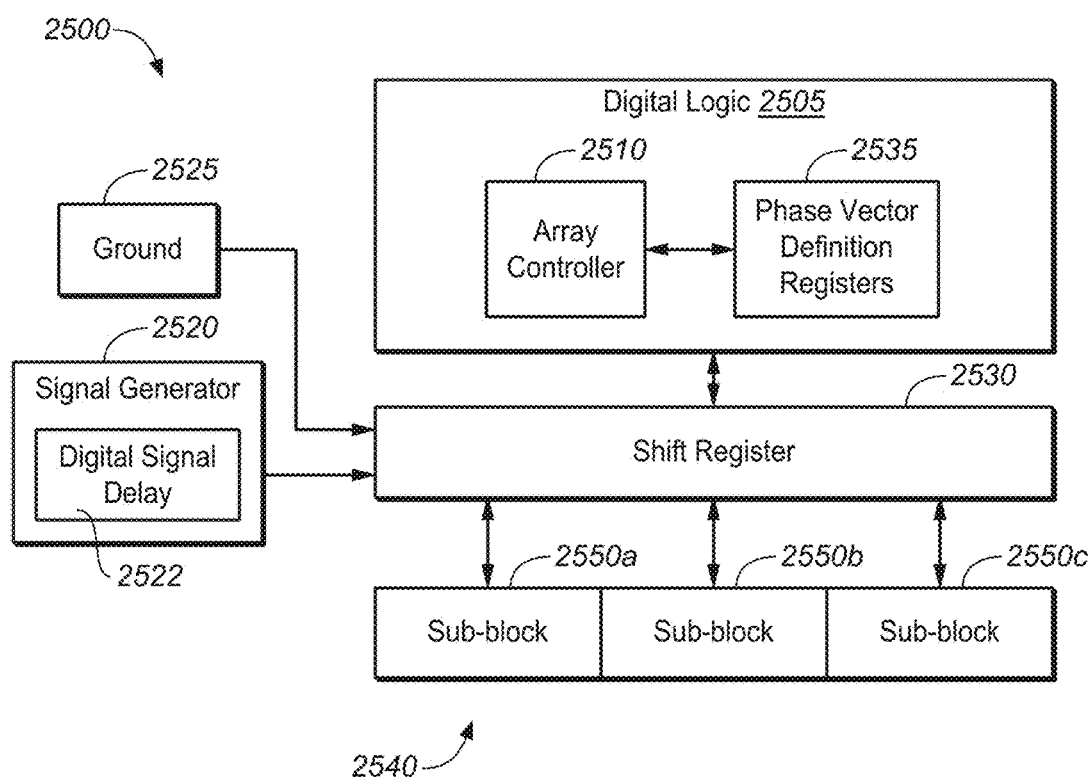
FIG. 25 illustrates an example ultrasonic sensor, according to an embodiment.

FIG. 25 illustrates an example ultrasonic sensor 2500, according to an embodiment. Ultrasonic sensor 2500 includes digital logic 2505, signal generator 2520, shift registers 2530, and two-dimensional array 2540 of ultrasonic transducers. Two-dimensional array 2540 includes three independently controllable sub-blocks 2550a-c (also referred to herein as "sub-arrays"). In one embodiment, digital logic 2505 includes array controller 2510 and phase vector definition registers 2535. It should be appreciated that two-dimensional array 2540 may include any number of sub-blocks of ultrasonic transducers, of which the illustrated embodiment is one example. In one embodiment, the ultrasonic transducers are Piezoelectric Micromachined Ultrasonic Transducer (PMUT) devices. In one embodiment, the PMUT devices include an interior support structure.

Signal generator 2520 generates a plurality of transmit signals, wherein each transmit signal of the plurality of transmit signals has a different phase delay relative to other transmit signals of the plurality of transmit signals. In one embodiment, signal generator 2520 includes a digital phase delay 2522 configured to apply at least one phase delay to a source signal from signal generator 2520 for generating the plurality of transmit signals. In one embodiment, ultrasonic sensor 2500 includes ground 2525 (e.g., an alternating current (AC) ground) providing a null signal, wherein the beamforming space identifies that the null signal is applied to ultrasonic sensors of the beamforming space that are not activated during the transmit operation. In another embodiment, the null signal is the lack of a signal waveform.

Shift registers 2530 store control bits for applying a beamforming space including a beamforming pattern to the two-dimensional array of ultrasonic transducers, where the beamforming pattern identifies a transmit signal of the plurality of transmit signals that is applied to each ultrasonic transducer of the beamforming space that is activated during a transmit operation. In one embodiment, shift registers 2530 store control bits for applying a plurality of instances of the beamforming space, wherein each instance of the beamforming space corresponds to a different sub-block 2550a-c of ultrasonic transducers, and wherein each instance of the beamforming space comprises the beamforming pattern. In one embodiment, the beamforming space includes a plurality of phase vectors corresponding to a one-dimensional subset of ultrasonic transducers, a phase vector identifying a signal to apply to a corresponding ultrasonic transducer during a transmit operation. In one embodiment, the signal is selected from a null signal and a transmit signal of the plurality of transmit signals. In one embodiment, the plurality of phase vectors are stored within phase vector definition registers 2535.

Array controller 2510 controls activation of ultrasonic transducers during a transmit operation according to the beamforming pattern and is configured to shift a position of the beamforming space within the shift register such that the beamforming space moves relative to the two-dimensional array of ultrasonic transducers. In one embodiment, array controller 2510 controls activation of ultrasonic transducers of more than one sub-block 2550a-c of ultrasonic transducers during a transmit operation according to the beamforming pattern of each instance of the beamforming space, where the beamforming pattern is applied to the more than one sub-block 2550a-c of ultrasonic transducers in parallel.

Figure 26A:
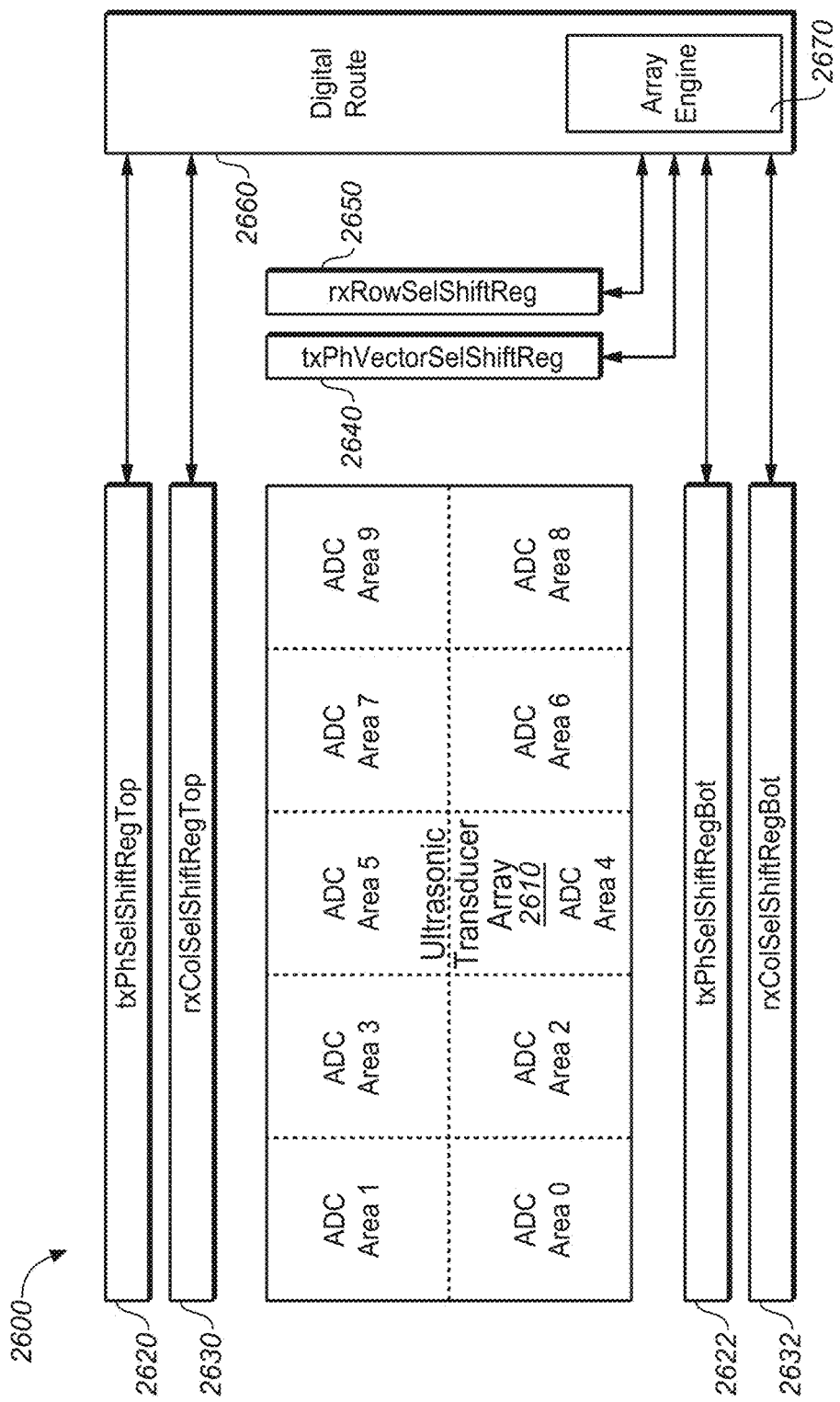
FIG. 26A illustrates example control circuitry of an array of ultrasonic transducers, according to an embodiment.

FIG. 26A illustrates example control circuitry 2600 of an array 2610 of ultrasonic transducers, according to an embodiment. Control circuitry 2600 includes phase select shift register (txPhSelShiftRegTop) 2620, phase select shift register (txPhSelShiftRegBot) 2622, column select shift register (rxColSelShiftRegTop) 2630, column select shift register (rxColSelShiftRegBot) 2632, phase vector select shift register (txPhVectSelShiftReg) 2640, row select shift register (rxRowVectSelShiftReg) 2650, digital route 2660, and array engine 2670. Array 2610 includes ten sub-blocks (e.g., ADC area) of ultrasonic transducers, each including a plurality of ultrasonic transducers (e.g., 24×24 or 23×27). Each sub-block of ultrasonic transducers is independently controllable by control circuitry 2600.

FIG. 26B illustrates an example shift register 2680, according to various embodiments. Shift register 2680 includes a plurality of shift elements 2682a-g (e.g., flip-flops) in series for shifting position of shift register data according to the shift clock (CLK) signal 2684. It should be appreciated that shift register 2680 may be implemented along a horizontal or vertical edge of an array of ultrasonic transducers, where each row or column has an associated flip flop. As illustrated, shift register 2680 includes J flip flops, where J is the number of ultrasonic transducers of in the horizontal or vertical direction.

In various embodiments, shift register 2680 is capable of handling different numbers of bits, as indicated by k, by using single or multi-bit flip-flops for the shift elements 2682a-g as needed. For example, for phase select shift registers 2620 and 2622, k=10 (five 2-bit settings), for phase vector select shift register 2640, k=3 (one 3-bit setting), for column select shift registers 2630 and 2632, k=1 (one 1-bit setting), and for row select shift register 2650, k=1 (one 1-bit setting). Shift clock signal 2684 is a gated clock that controls the shifting of shift register 2680, where shift register data is shifted by one shift element for every clock pulse, according to an embodiment. While shift register 2680 is illustrated as a one-directional shift register, it should be appreciated that shift register 2680 may also be implemented as a b-directional shift record.

Multiplexer 2687 allows for the recirculation of previously entered shift register data or for loading new shift register data. When load signal (Load_shiftb) 2688 is set low (e.g., zero), the currently loaded data is shifted through shift register 2680 (e.g., looped via loop 2690) such that data that exits the end of shift register 2680 (e.g., from the output of shift element 2682g) is recirculated back to the beginning of shift register 2680 (e.g. to the input of shift element 2682a). When load signal 2688 is set to high (e.g., 1), new data 2686 (e.g., phase select settings, phase vector select settings, etc.) is entered into shift register 2680 in response to pulses applied on shift clock signal 2684.

For configuring the ultrasonic transducers for a transmit operation, the two shift register blocks (phase select shift register 2620 and phase select shift register 2622) run along the top and bottom edges of array 2610, respectively, and control which transmit signals are selected for transmission through the ultrasonic transducer array 2610. It should be appreciated that the shift registers can be in any physical position relative to the array, and that the illustrated embodiment is one example of placement; the position and number of shift register blocks may be dependent on the number of sub-blocks of the array. In one embodiment, phase select shift register 2620 and phase select shift register 2622 control which transmit signals are sent through array 2610 according to phase vector definition registers stored in digital route 2660. These signals are then selectively applied to specific ultrasonic transducers of the sub-blocks by the outputs of phase vector select shift register 2640, which run through the rows of array 2610.

In one embodiment, ultrasonic transducers selected to receive are designated by driving an "rxRowSelY" logic signal through each row of ultrasonic transducers (where 'Y' specifies the Y-axis row number) and an "rxColSelX" signal through each column of ultrasonic transducers (where 'X' specifies the X-axis column number). An ultrasonic transducer is activated to receive whenever both its rxRowSelY and its rxColSelX signals are set to a logic level '1'. In this way, for example, we would activate the four ultrasonic transducers at (4, 3), (5, 3), (4, 4), and (5, 4) in FIG. 22A to receive by setting rxRowSel3, rxRowSel4, rxColSel4, and rxColSel5 to logic level '1' and setting the remaining 7 rxRowSelY lines and the remaining 7 rxColSelX lines to logic level '0'. With reference to FIG. 26, the receive (rx) select signals are determined by column select shift register 2632 and row select shift register.

Figure 27:
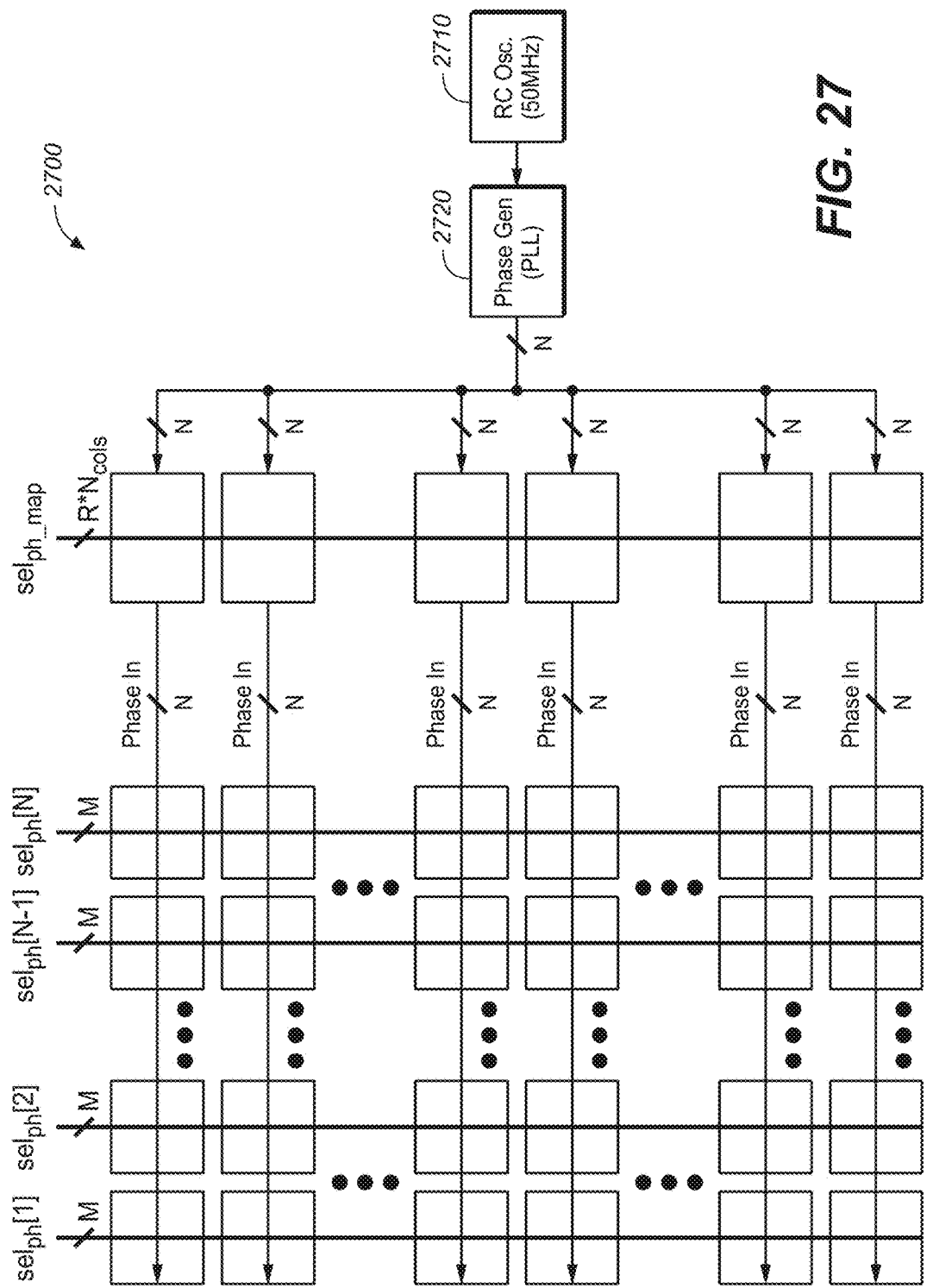
FIG. 27 illustrates an example transmit path architecture of a two-dimensional array of ultrasonic transducers, according to some embodiments.

FIG. 27 illustrates an example transmit path architecture 2700 of a two-dimensional array of ultrasonic transducers, according to some embodiments. Achieving two-dimensional beamforming with high image resolution under glass uses relatively high ultrasonic frequencies and precise timing. Electronics to support an ultrasonic transducer array with a resonant frequency of 50 MHz and a beamforming timing resolution of 1 nanosecond can be used. The 50 MHz frequency can be generated by an on-chip RC oscillator 2710 (e.g., timing block) that can be trimmed for sufficient accuracy by an off-chip clock source. The beamforming resolution can be set by an on-chip phase-locked loop (PLL) 2720 that outputs several timing phases that correspond to ~3 cycles of 50 MHz frequency and are appropriately delayed with respect to each other. These phases can be routed to each ultrasonic transducer according to the sel$_{ph\_map}$ signals shown in the FIG. 27.

Figures 28, 28A:
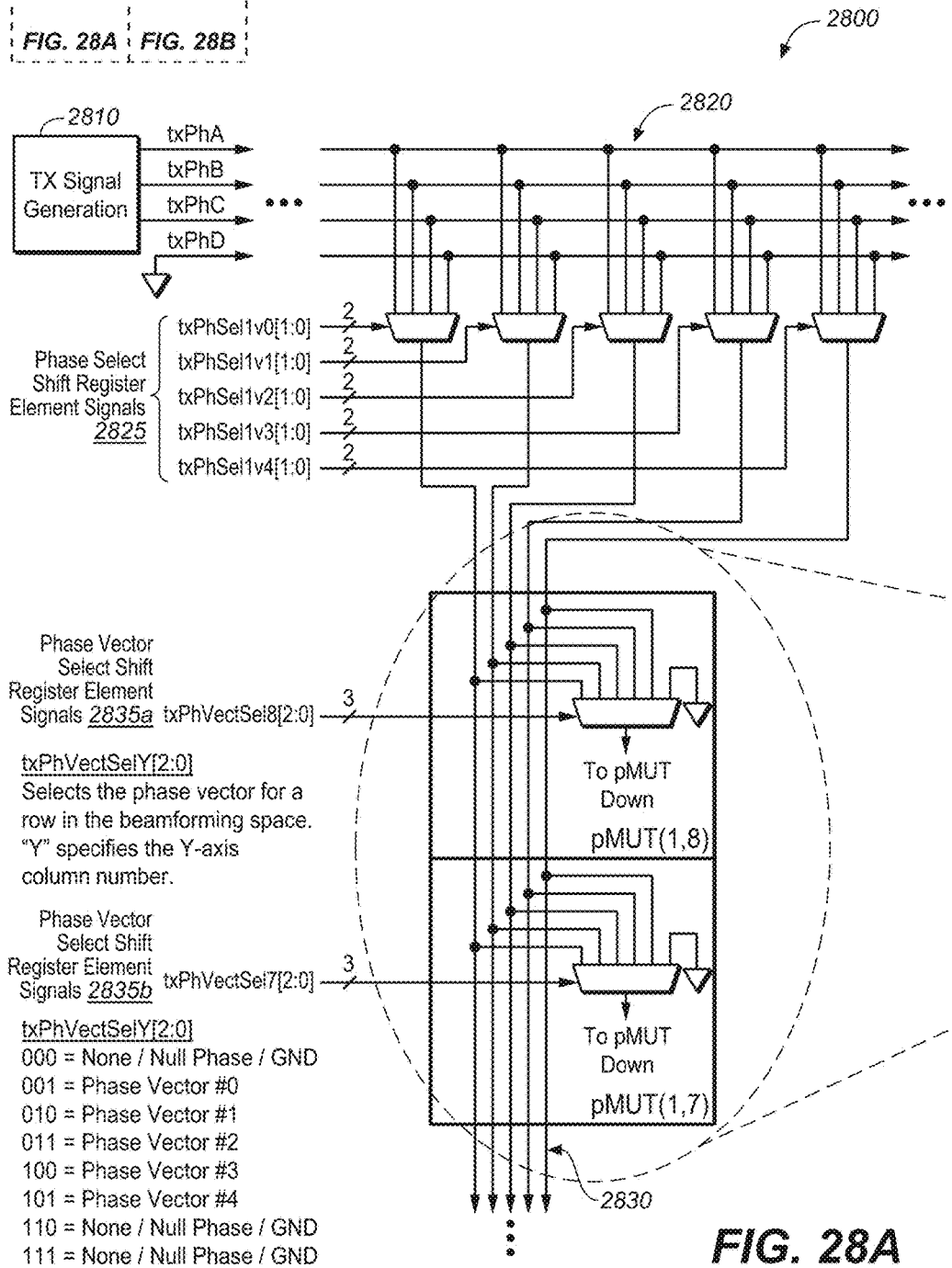
FIGS. 28, 28A, and 28B illustrate example circuitry for configuring an array of ultrasonic transducers for a transmit operation, according to an embodiment.
Figure 28B:
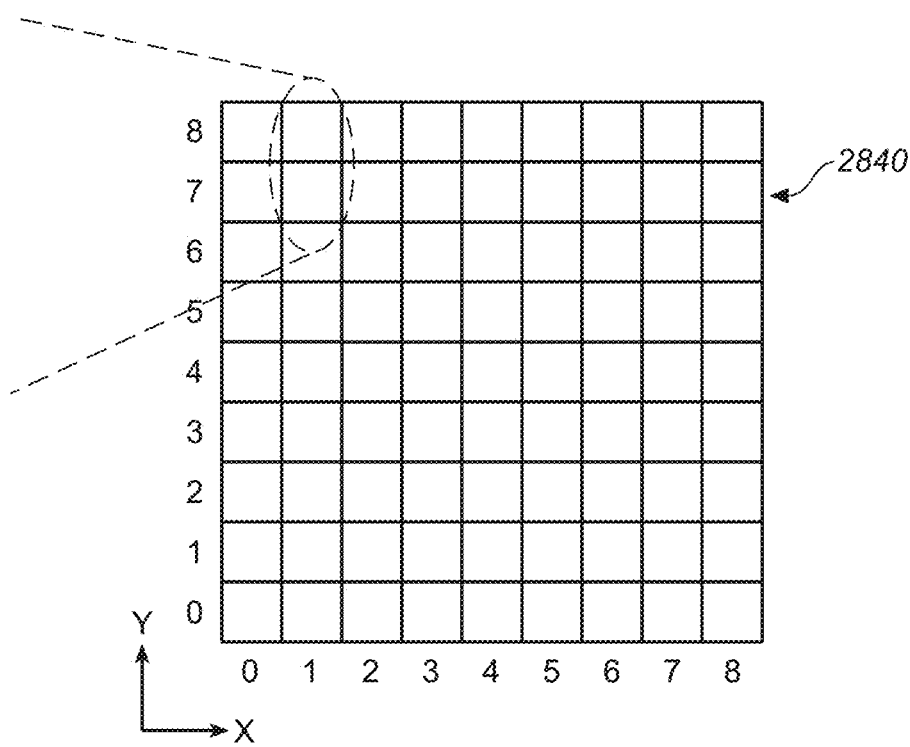

FIGS. 28, 28A, and 28B illustrate example circuitry 2800 for configuring a sensor array of ultrasonic transducers for a transmit operation, according to an embodiment. The ultrasonic sensor includes a transmit signal generator 2810 for generating transmit signals of independently configurable phase (delay) relative to one another. In one embodiment, these signals are generated at a timing block of the ultrasonic sensor. In one embodiment, transmit signal generator generates three signals:

txPhA (complementary signal, if needed, is txPhA_b)—corresponds to signal 'A' in the beamforming space;

txPhB (complementary signal, if needed, is txPhA_b)—corresponds to signal 'B' in the beamforming space; and txPhC (complementary signal, if needed, is txPhC_b)—corresponds to signal 'C' in the beamforming space.

These transmit signals are distributed on lines 2820 along the top and bottom of the ultrasonic transducer array to maintain their relative phase (delay) relationship to one another. In one embodiment, the signals are distributed at twice their desired frequency and divided down to the correct frequency just before being driven into each column of ultrasonic transducers in the array.

The ultrasonic sensor also includes a null signal, also referred to herein as "txPhD." It should be appreciated that the null signal is not actually distributed since it is a null phase (no signal/GND) which is readily available through the ultrasonic sensor.

Phase select shift register element signals 2825, received from a phase select shift register (e.g., phase select shift register 2620 or phase select shift register 2622), includes five 2-bit settings that are output from one element of the phase select shift register. Phase select shift register element signals 2825 drive signal multiplexers that select the transmit signals that are sent down lines 2830. Phase vector select shift register element signals 2835*a* and 2835*b*, received from a phase vector select shift register (e.g., phase vector select shift register 2640), are 3-bit settings output from two elements within the phase vector select shift register that select which one of the transmit signals on lines 2830 is driven to the corresponding ultrasonic transducer (e.g., PMUT as illustrated).

The following digital signals are used for configuring 9×9 regions within the actual ultrasonic transducer sensor array to behave according to the beamforming transmit configuration registers:

Transmit phase vector element selection signal (txPhSelXvV[1:0]) selects the transmit signal to be placed onto one of the five lines 2830 that run down through a column of ultrasonic transducers. This signal implements/selects the phase vector elements, where
'X' specifies to the X-axis column number within beamforming space 2840
'V' refers to the phase vector (0-4)
Examples: txPhSel1v4 for Ph4$_1$, txPhSel3v2 for Ph2$_3$
Values: 00=Select txPhA ('A')
01=Select txPhB ('B')
10=Select txPhC ('C')
11=Select txPhD ('D'/no signal/GND)
Transmit phase vector selection signal (txPhVectSelY[2:0]) selects the phase vector for a row in the beamforming space 2840. This signal implements/selects the phase vector to be applied to each Y-axis row, where
'Y' specifies to the Y-axis row number
Values: 000=None/Null Phase/GND
001=Phase Vector #0
010=Phase Vector #1
011=Phase Vector #2
100=Phase Vector #3
101=Phase Vector #4
110=None/Null Phase/GND
111=None/Null Phase/GND FIGS. 28, 28A, and 28B illustrate how these signals and associated hardware are used in the ultrasonic sensor to configure the actual ultrasonic transducer sensor array to behave according to the beamforming transmit configuration registers. As illustrated, a transmit signal is selected for placement onto one of the five lines that runs along a column of ultrasonic transducers according to the transmit phase vector element selection signal. The phase vector for a row in the beamforming space 2840 is then selected according to the transmit phase vector selection signal. The resulting signal for the ultrasonic transducer (e.g., PMUT) is then provided to the driver of the ultrasonic transducer for activation.

Figure 29A:
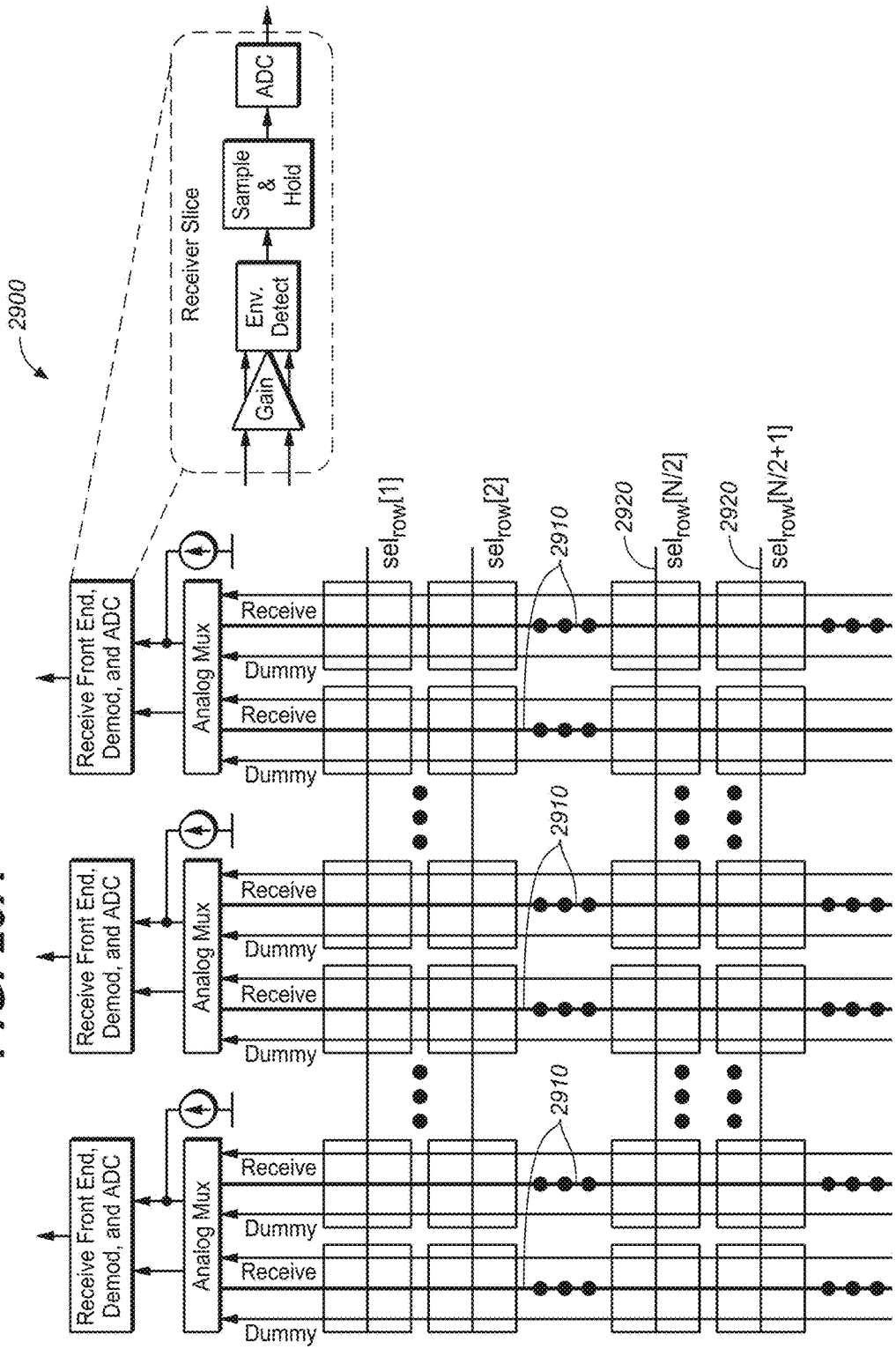
FIGS. 29, 29A, and 29B illustrate an example receive path architecture of a two-dimensional array of ultrasonic transducers, according to some embodiments.
Figures 29, 29B:
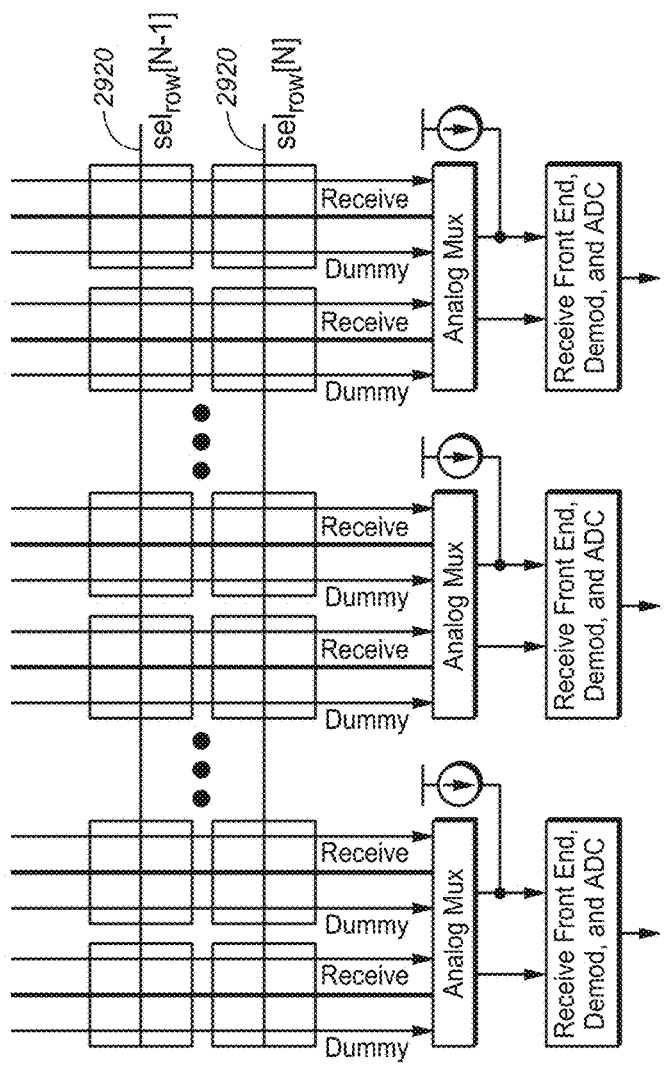

FIGS. 29, 29A, and 29B illustrate an example receive path architecture 2900 of a two-dimensional array of ultrasonic transducers, according to some embodiments. The select lines 2910 correspond to rxColsel[k] for receive, and the select lines 2920 correspond to rxRowsel[k] for receive. Multiple PMUTs can be selected together for receiving the signal. The signal from the PMUTs is fed into a front end receiver. The signal is then filtered to reduce noise outside of the signal bandwidth. The filtered signal is then integrated and digitized with an ADC. In some embodiments, the PMUT and receiver layout allow straightforward extension of the PMUT array size, since different applications can require different sensor array areas. The number of receiver slices will be determined by the desired PMUT array size and minimum ultrasonic transducer separation between transmit beams. For example, in one embodiment, a twenty ultrasonic transducer minimum separation between adjacent sets of active ultrasonic transducers reduces crosstalk.

In one embodiment, the receive slices interface with the timing block, with the two-dimensional array of ultrasonic transducers, and with the digital logic of the sensor device. For example, the receive slices receive the timing signals from the timing block. From the digital logic, the receive slices receive many static trims (e.g., coarse amplifier gain settings, ADC range settings, etc.) that are shared by all receive slices. In addition, in some embodiments, the receive slices receive some static trims that are unique to each receive slice (e.g., test mode enables, ADC offset settings). In some embodiments, the receive slices receive fine gain control for the third amplifier stage, which is adjusted dynamically before each pixel Tx/Rx operation. For example, each receive slice provides 8-bit ADC output data to the digital logic.

Between the receive slices and the two-dimensional array of ultrasonic transducers, a set of column select switches and decoder logic act on the column select signals to decide which columns get connected to the receive slices' analog inputs. If no columns are selected for a given receive slice, then the receive slice is not enabled by the column decoder logic. Embodiments of the details of the column and row selection logic are explained in FIGS. 30A-30D.

Figure 30A:
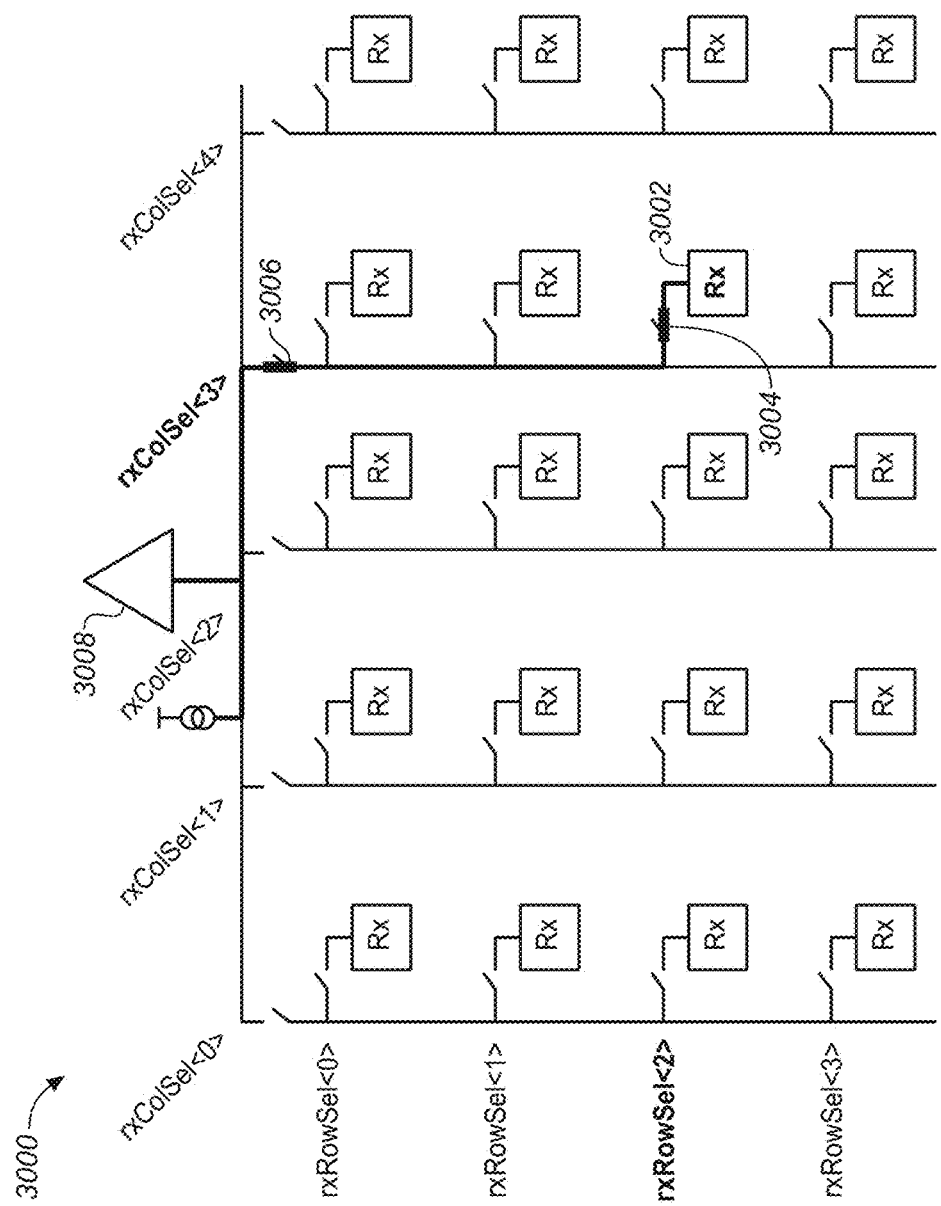
FIGS. 30A-30D illustrate example circuitry for selection and routing of received signals during a receive operation, according to some embodiments.

FIGS. 30A-30D illustrate example circuitry for selection and routing of received signals during a receive operation, according to some embodiments. With reference to FIG. 30A, example circuit 3000 illustrates an example of a 1-pixel receive selection, in accordance with an embodiment. Each in-pixel receiver (e.g., receiver of an ultrasonic transducer) connects to its shared column line through a switch. This switch is activated when the associated row select and column select line is asserted. Then, to route this receiver's output into the receive slice, an additional switch at the edge of the array connects the selected column to the receive chain input. For example, in-pixel receiver 3002 is activated responsive to activating switch 3004 by asserting rxRowSel<2> and rxColSel<3>. To route the output of in-pixel receiver 3002 into the receive slice, switch 3006 is activated by rxColSel<3> to connect the column to receive chain input 3008.

Figure 30B:
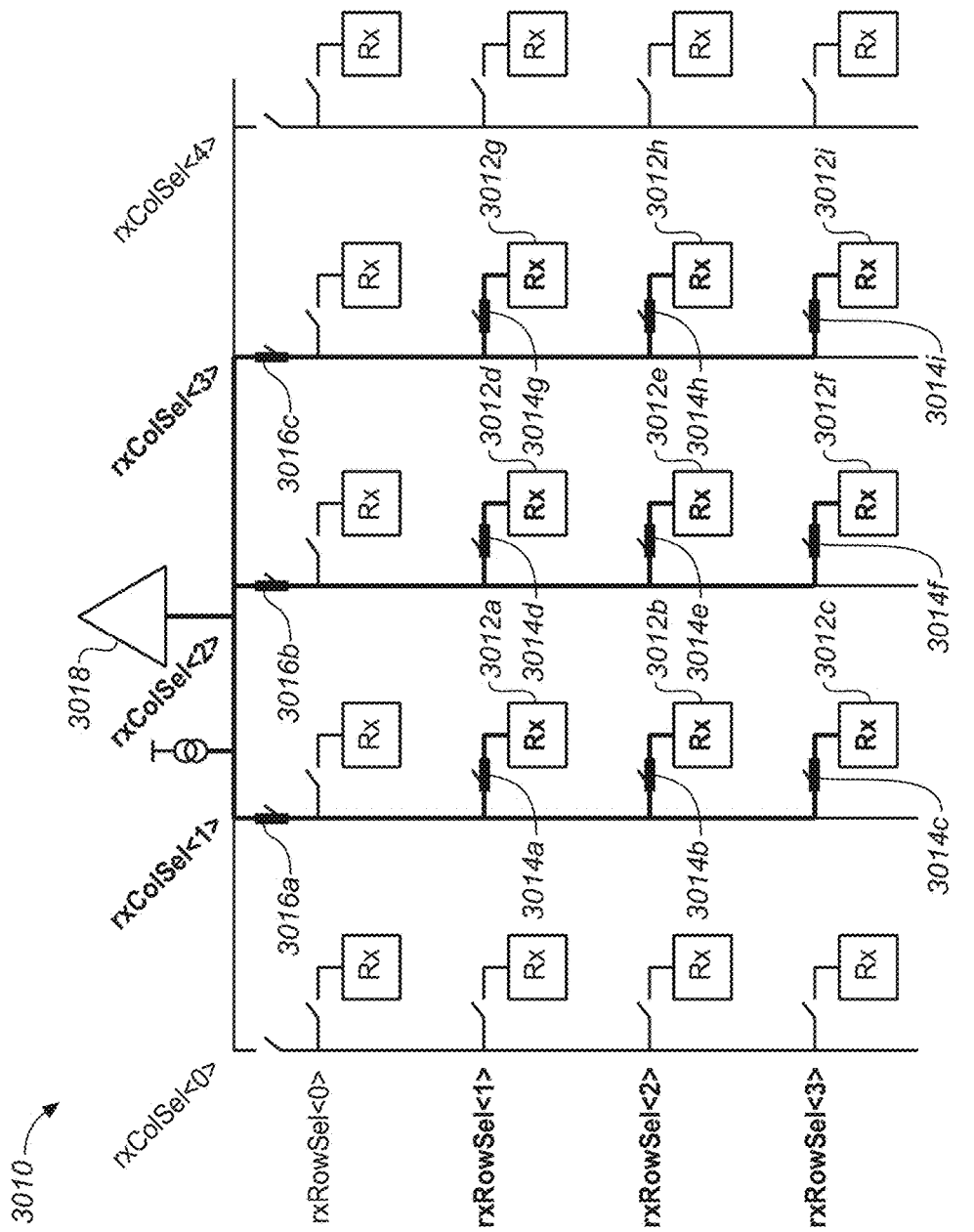

With reference to FIG. 30B, example circuit 3010 illustrates an example 3×3 pixel receive pattern, in accordance with an embodiment. As illustrated, multiple row and multiple column select lines are asserted simultaneously. For example, in-pixel receivers 3012*a-i* are activated responsive to activating switches 3014*a-i* by asserting rxRowSel<1>, rxRowSel<2>, and rxRowSel<3>, and rxColSel<1>, rxColSel<2>, and rxColSel<3>. To route the outputs of in-pixel receivers 3012a-i into the receive slice, switches 3016a-c are activated by rxColSel<1>, rxColSel<2>, and rxColSel<3> to connect the column to receive chain input 3018. It should be appreciated that any combination of row and column select lines may be asserted to provide different sizes of pixel receive patterns (e.g., asserting two adjacent row select lines and two adjacent column select lines will provide 2×2 pixel receive pattern).

Figure 30C:
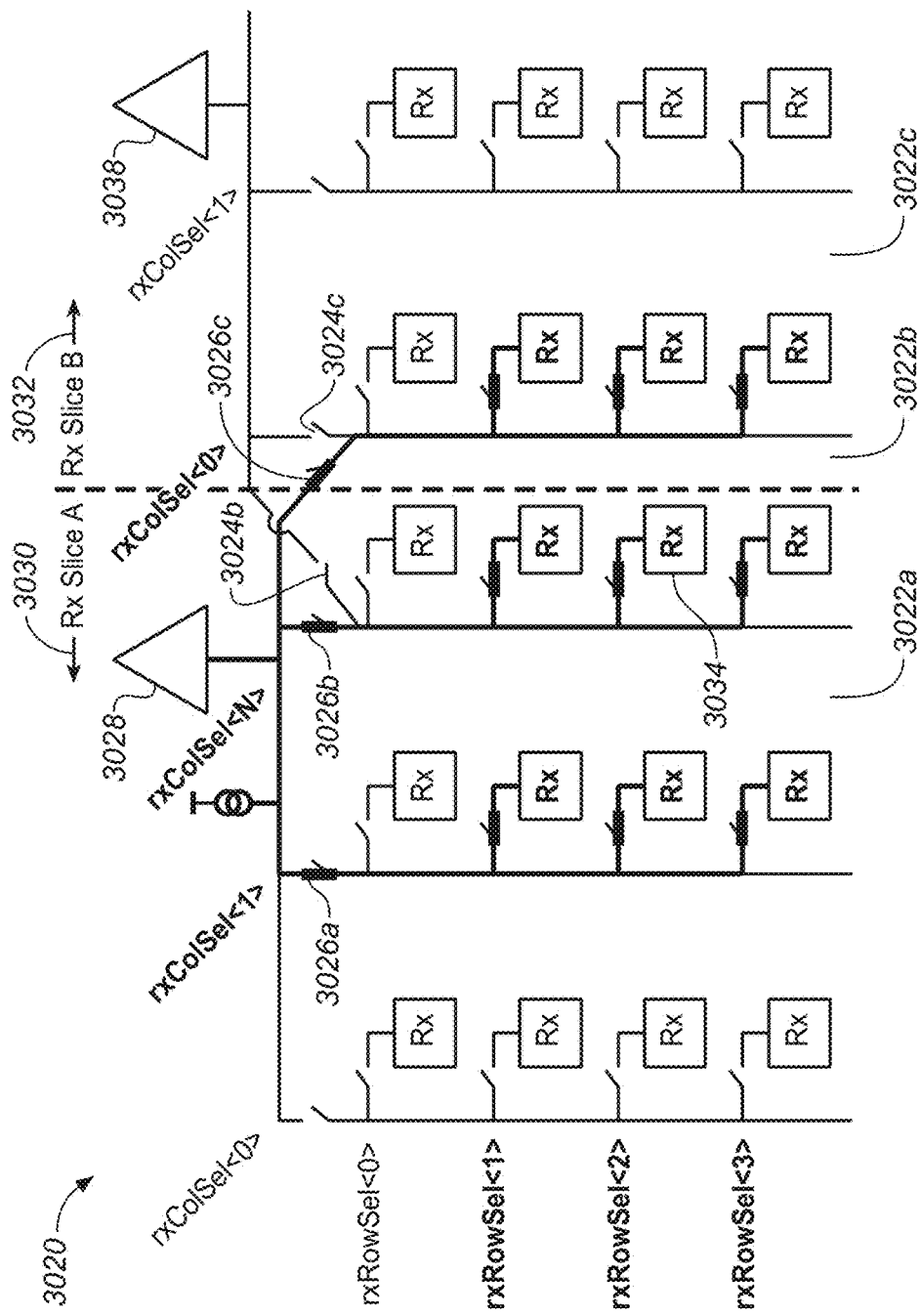

With reference to FIG. 30C, example circuit 3020 illustrates an example 3×3 pixel receive pattern, where the 3×3 pixel receive pattern overlaps two receive slices 3030 and 3032 (e.g., two sub-arrays) at a vertical sub-array boundary, in accordance with an embodiment. As illustrated, multiple row and multiple column select lines are asserted simultaneously, as described in FIG. 30B. However, in-pixel receivers of columns 3022a and 3022b are associated with receive slice 3030 and in-pixel receivers of column 3022c are associated with receive slice 3032. In order to ensure appropriate routing of receive signals, columns 3022b and 3022c, which border adjacent receive slices, include additional switches to support multi-pixel receive across sub-array boundaries. Column select logic determines which switches to enable to route the column output to the correct receive slice.

In one embodiment, the receive slice of the center in-pixel receiver of the receive pattern is used to determine which receive slice is selected for receiving the receive signals. As illustrated, in-pixel receiver 3034 is the center in-pixel receiver of the receive pattern and is located with receive slice 3030. As such, switch 3026a of column 3022a, switch 3026b of column 3022b, and switch 3026c of column 3022c are activated to ensure that the output of the activated in-pixel receivers is routed to the input 3028 of the receive slice 3030. Switch 3024b of column 3022b and switch 3024c of column 3022c are not activated, as they are associated with input 3038 of receive slice 3032. It should be appreciated that another in-pixel receiver may be selected as the representative in-pixel receiver. For example, for a 2×2 receive pattern, there is no center pixel. As such, any in-pixel receiver (e.g., the upper left in-pixel receiver) may be selected as the representative in-pixel receiver for directing the receive signals to the appropriate receive slice.

Figure 30D:
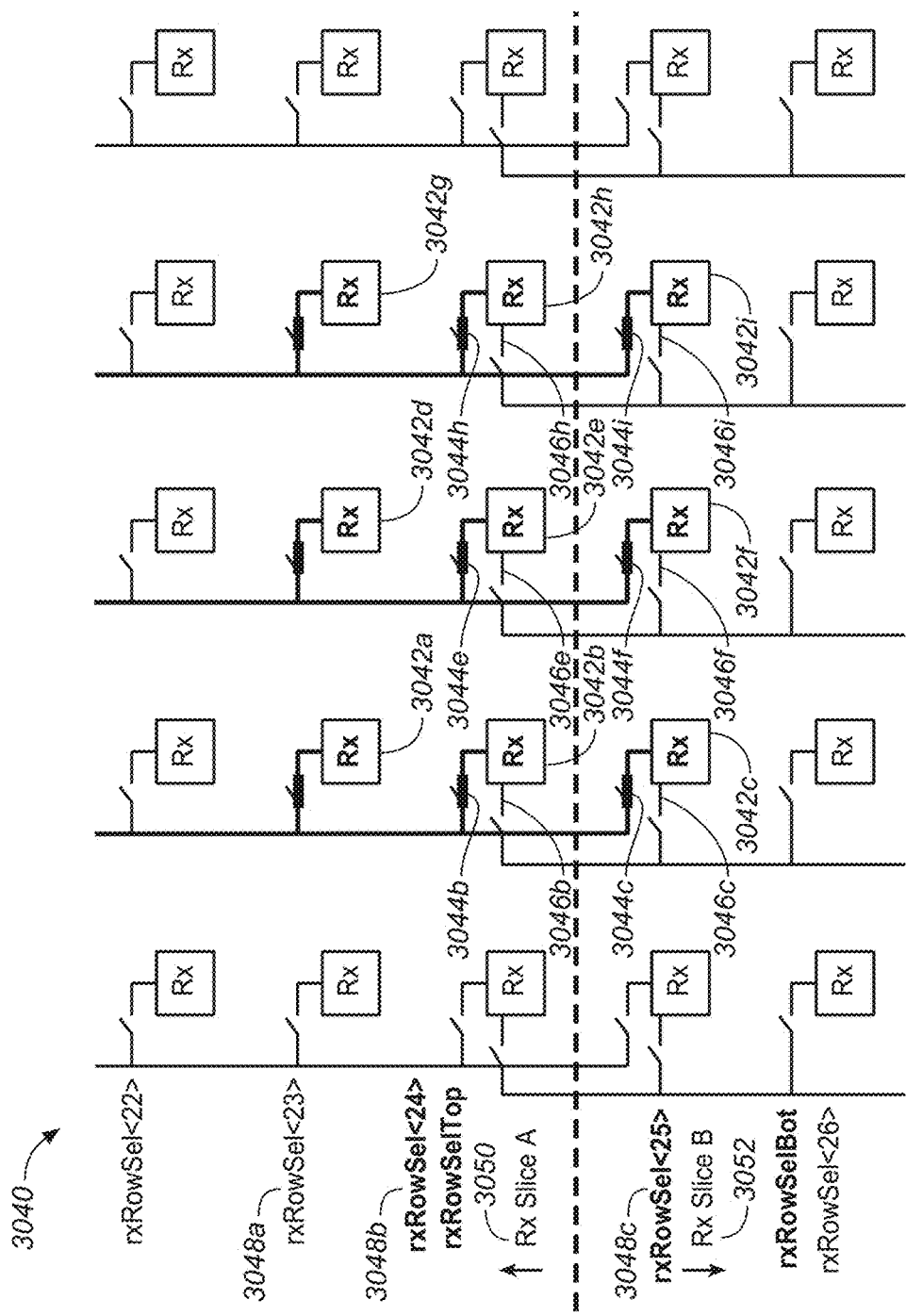

With reference to FIG. 30D, example circuit 3040 illustrates an example 3×3 pixel receive pattern, where the 3×3 pixel receive pattern overlaps two receive slices 3050 and 3052 (e.g., two sub-arrays) at a horizontal sub-array boundary, in accordance with an embodiment. As illustrated, multiple row and multiple column select lines are asserted simultaneously, as described in FIG. 30B. However, in-pixel receivers of rows 3048a and 3048b (in-pixel receivers 3042a, 3042b, 3042d, 3042e, 3042g, and 3042h) are associated with receive slice 3050 and in-pixel receivers of row 3048c (in-pixel receivers 3042c, 3042f, and 3042i) are associated with receive slice 3052. In order to ensure appropriate routing of receive signals, in-pixel receivers of rows 3048b and 3048c, which border adjacent receive slices, include additional switches to support multi-pixel receive across sub-array boundaries. At the horizontal boundary between the top half of the array and the bottom half of the array, additional switches and control logic are needed both at the edge of the array (e.g., to generate the receiveRowSelTop and receiveRowSelBot signals), and inside the ultrasonic transducers, in order to choose between connecting to the top column line or the bottom column line.

In one embodiment, the receive slice of the center in-pixel receiver of the receive pattern is used to determine which receive slice is selected for receiving the receive signals. As illustrated, in-pixel receiver 3042e is the center in-pixel receiver of the receive pattern and is located with receive slice 3050. As such, switches 3044b, 3044c, 3044e, 3044f, 3044h, and 3044i are activated to ensure that the output of the activated in-pixel receivers is routed to the receive chain input of receive slice 3050. Switches 3046b, 3046c, 3046e, 3046f, 3046h, and 3046i are not activated, as they are associated with receive slice 3052. It should be appreciated that another in-pixel receiver may be selected as the representative in-pixel receiver. For example, for a 2×2 receive pattern, there is no center pixel. As such, any in-pixel receiver (e.g., the upper left in-pixel receiver) may be selected as the representative in-pixel receiver for directing the receive signals to the appropriate receive slice.

FIGS. 31A through 34 illustrate flow diagrams of example methods for operating a fingerprint sensor comprised of ultrasonic transducers, according to various embodiments. Procedures of this method will be described with reference to elements and/or components of various figures described herein. It is appreciated that in some embodiments, the procedures may be performed in a different order than described, that some of the described procedures may not be performed, and/or that one or more additional procedures to those described may be performed. The flow diagrams include some procedures that, in various embodiments, are carried out by one or more processors under the control of computer-readable and computer-executable instructions that are stored on non-transitory computer-readable storage media. It is further appreciated that one or more procedures described in the flow diagrams may be implemented in hardware, or a combination of hardware with firmware and/or software.

Figure 31A:
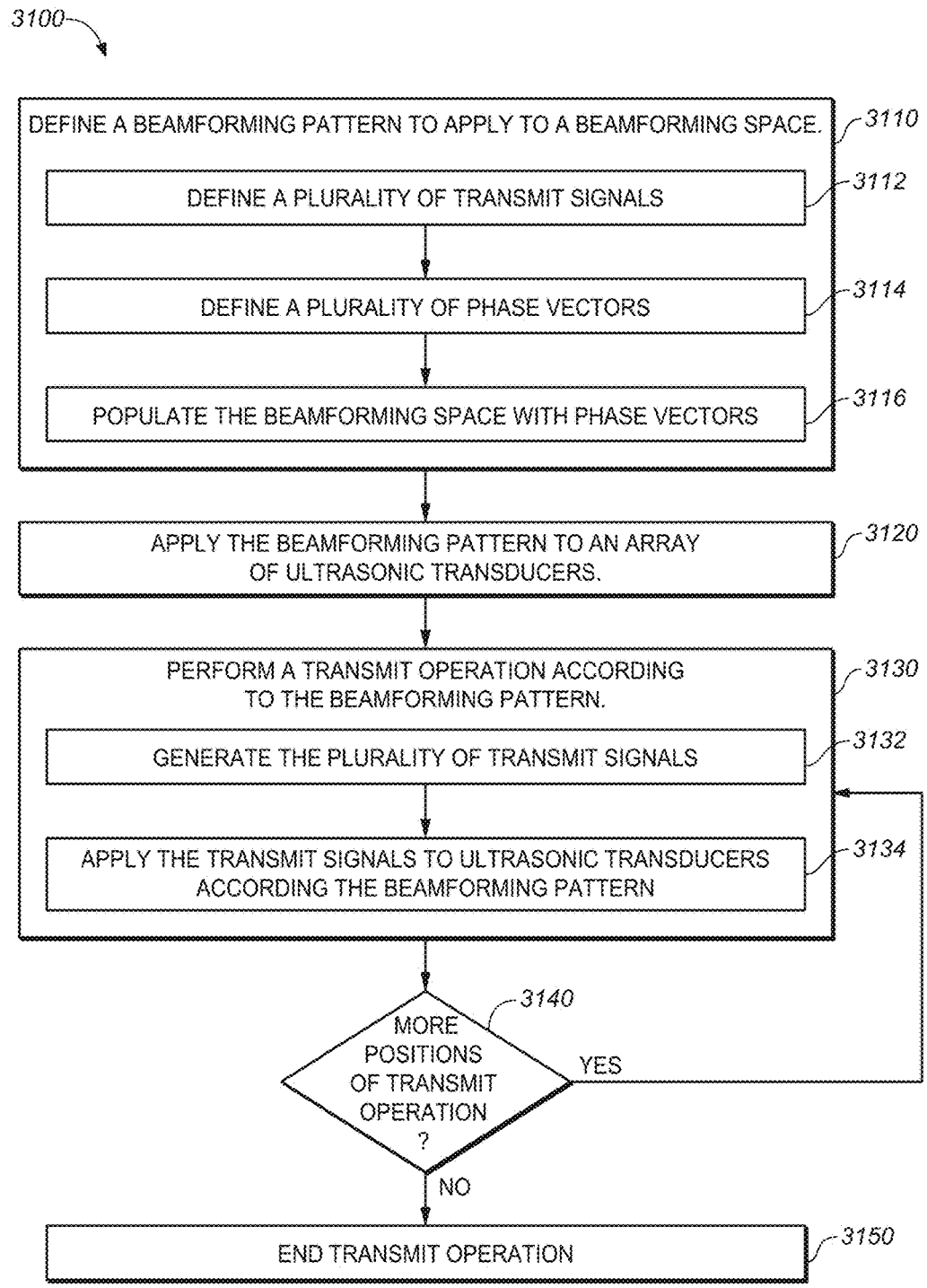
FIGS. 31A and 31B illustrate a flow diagram of an example method for transmit beamforming of a two-dimensional array of ultrasonic transducers, according to various embodiments.
Figure 31B:
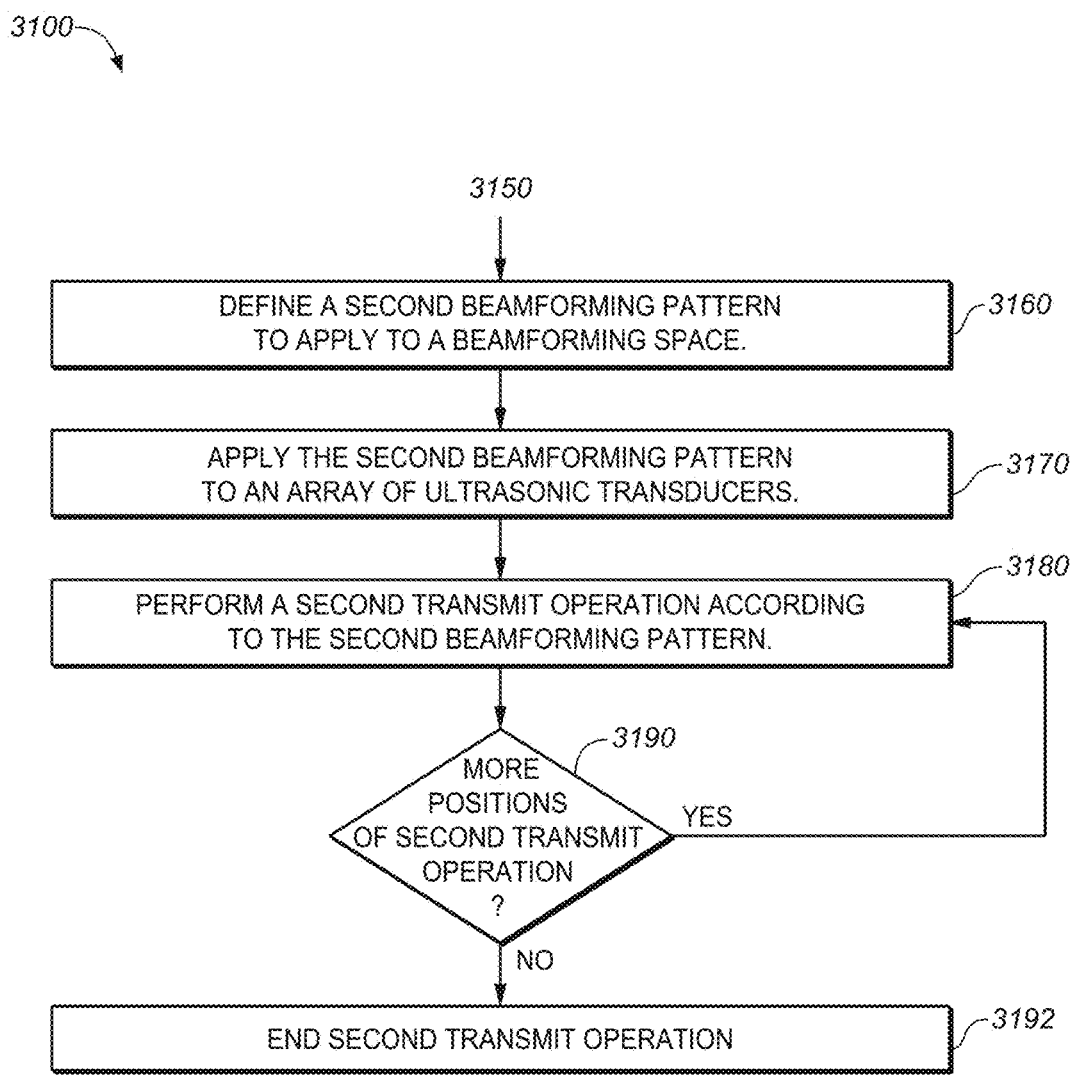

FIGS. 31A and 31B illustrate a flow diagram of an example method for transmit beamforming of a two-dimensional array of ultrasonic transducers, according to various embodiments. With reference to FIG. 31A, at procedure 3110 of flow diagram 3100, a beamforming pattern to apply to a beamforming space of the two-dimensional array of ultrasonic transducers is defined. The beamforming space includes a plurality of elements, where each element of the beamforming space corresponds to an ultrasonic transducer of the two-dimensional array of ultrasonic transducers. The beamforming pattern identifies which ultrasonic transducers within the beamforming space are activated during a transmit operation of the two-dimensional array of ultrasonic transducers, wherein at least some of the ultrasonic transducers that are activated are phase delayed with respect to other ultrasonic transducers that are activated.

In one embodiment, the beamforming pattern is symmetrical about a position of the beamforming space. In one embodiment, the position is a center element of the beamforming space. In one embodiment, the position is an intersection of elements somewhere within the beamforming space. In one embodiment, the position is a line bisecting the beamforming space. In one embodiment, the beamforming space includes n×m elements.

In one embodiment, as shown at procedure 3112, a plurality of transmit signals is defined, where each transmit signal of the plurality of transmit signals has a different phase delay relative to other transmit signals of the plurality of transmit signals, and where elements corresponding to ultrasonic transducers that are activated during the transmit operation include an associated transmit signal of the plurality of transmit signals. In one embodiment, as shown at procedure 3114, a plurality of phase vectors including a one-dimensional subset of elements of the plurality of elements is defined, where elements of a phase vector of the plurality of phase vectors include one of a null signal and the plurality of transmit signals, and where elements corresponding to ultrasonic transducers that are not activated during the transmit operation include the null signal. In one embodiment, as shown at procedure 3116, the beamforming space is populated with phase vectors of the plurality of phase vectors. In one embodiment, the beamforming space includes n×m elements and where each phase vector of the plurality of phase vectors includes n elements.

At procedure 3120, the beamforming pattern is applied to the two-dimensional array of ultrasonic transducers.

At procedure 3130, a transmit operation is performed by activating the ultrasonic transducers of the beamforming space according to the beamforming pattern. In one embodiment, as shown at procedure 3132, the plurality of transmit signals are generated. In one embodiment, as shown at procedure 3134, the plurality of transmit signals is applied to ultrasonic transducers that are activated during the transmit operation according to the beamforming pattern.

In one embodiment, as shown at procedure 3140, it is determined whether there are more positions within the two-dimensional array to perform the transmit operation. If it is determined that there are more positions, flow diagram 3100 returns to procedure 3130 to repeat the transmit operation by activating the ultrasonic transducers of the beamforming space for multiple positions of the beamforming space within the two-dimensional array of ultrasonic transducers. If it is determined that there are no more positions within the two-dimensional array to perform the transmit operation, as shown at procedure 3150, the transmit operation ends.

In accordance with various embodiments, multiple beamforming patterns may be used for imaging in an ultrasonic sensor. With reference to FIG. 31B, in accordance with one embodiment, flow diagram 3100 proceeds to procedure 3160, where a second beamforming pattern to apply to the beamforming space of the two-dimensional array of ultrasonic transducers is defined. The second beamforming pattern identifies which ultrasonic transducers within the beamforming space are activated during a second transmit operation of the two-dimensional array of ultrasonic transducers, and where at least some of the ultrasonic transducers that are activated during the second transmit operation are phase delayed with respect to other ultrasonic transducers that are activated during the second transmit operation.

At procedure 3170, the second beamforming pattern is applied to the two-dimensional array of ultrasonic transducers.

At procedure 3180, a second transmit operation is performed by activating the ultrasonic transducers of the beamforming space according to the second beamforming pattern.

In one embodiment, as shown at procedure 3190, it is determined whether there are more positions within the two-dimensional array to perform the second transmit operation. If it is determined that there are more positions, flow diagram 3100 returns to procedure 3180 to repeat the second transmit operation by activating the ultrasonic transducers of the beamforming space for multiple positions of the beamforming space within the two-dimensional array of ultrasonic transducers. If it is determined that there are no more positions within the two-dimensional array to perform the second transmit operation, as shown at procedure 3192, the second transmit operation ends.

Figure 32:
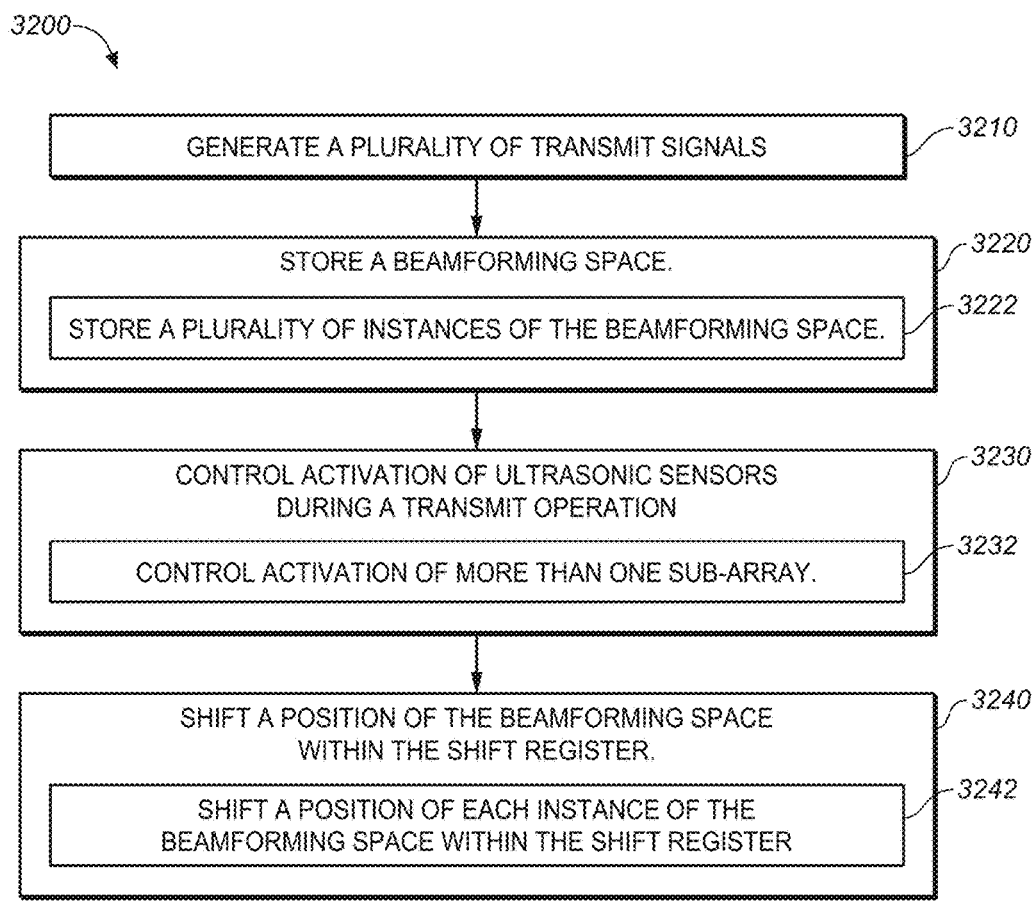
FIG. 32 illustrates a flow diagram of an example method for controlling an ultrasonic sensor during a transmit operation, according to various embodiments.

FIG. 32 illustrates a flow diagram of an example method for controlling an ultrasonic sensor during a transmit operation, according to various embodiments. At procedure 3210 of flow diagram 3200, a plurality of transmit signals is generated at a signal generator of the ultrasonic sensor, where each transmit signal of the plurality of transmit signals has a different phase delay relative to other transmit signals of the plurality of transmit signals.

At procedure 3220, a beamforming space is stored at a shift register of the ultrasonic sensor, the beamforming space including a beamforming pattern to apply to a two-dimensional array of ultrasonic transducers, where the beamforming pattern identifies a transmit signal of the plurality of transmit signals that is applied to each ultrasonic transducer of the beamforming space that is activated during a transmit operation. In one embodiment, the two-dimensional array of ultrasonic transducers includes a plurality of sub-arrays of ultrasonic transducers, wherein a sub-array of ultrasonic transducers of the plurality of sub-arrays of ultrasonic transducers is independently controllable. In one embodiment, as shown at procedure 3222, a plurality of instances of the beamforming space is stored at the shift register of the ultrasonic sensor, where each instance of the beamforming space corresponds to a different sub-array of ultrasonic transducers, and where each instance of the beamforming space includes the beamforming pattern.

At procedure 3230, activation of ultrasonic transducers during a transmit operation is controlled according to the beamforming pattern. In one embodiment, as shown at procedure 3232, activation of ultrasonic transducers of more than one sub-array of ultrasonic transducers during a transmit operation is controlled according to the beamforming pattern of each instance of the beamforming space, wherein the beamforming pattern is applied to the more than one sub-array of ultrasonic transducers in parallel.

At procedure 3240, a position of the beamforming space within the shift register is shifted such that the beamforming space moves relative to the two-dimensional array of ultrasonic transducers. In one embodiment, as shown at procedure 3242, a position of each instance of the beamforming space within the shift register is shifted in parallel across the plurality of sub-arrays of ultrasonic transducers.

Figure 33:
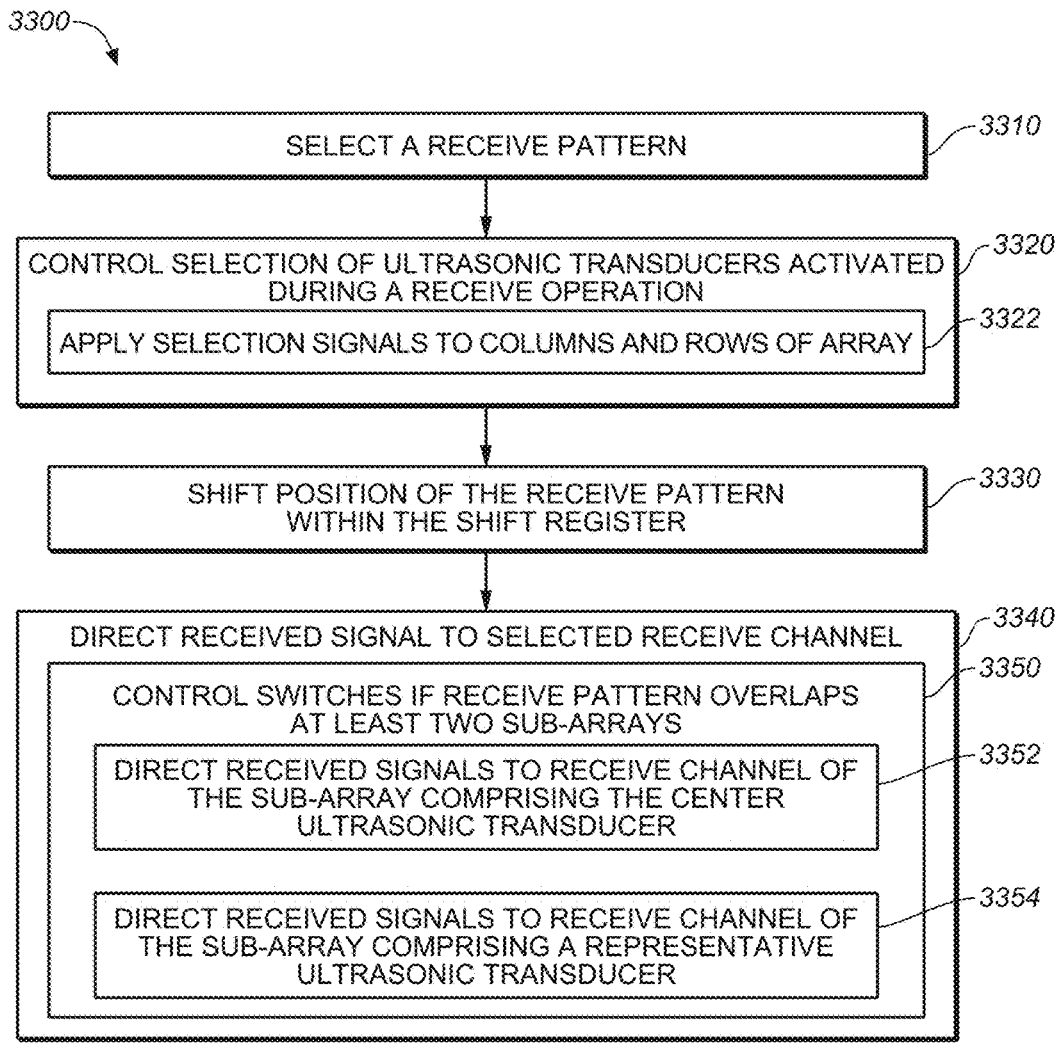
FIG. 33 illustrates a flow diagram of an example method for controlling an ultrasonic sensor during a receive operation, according to various embodiments.

FIG. 33 illustrates a flow diagram of an example method for controlling an ultrasonic sensor during a receive operation, according to various embodiments. At procedure 3310 of flow diagram 3300, a receive pattern of ultrasonic transducers of a two-dimensional array of ultrasonic transducers is selected to activate during a receive operation using a plurality of shift registers. The two-dimensional array of ultrasonic transducers includes a plurality of sub-arrays of ultrasonic transducers, where a sub-array of ultrasonic transducers of the plurality of sub-arrays of ultrasonic transducers is independently or jointly controllable, and where a sub-array of ultrasonic transducers has an associated receive channel. In one embodiment, the receive pattern specifies a 2×2 section of ultrasonic transducers. In one embodiment, the receive pattern specifies a 3×3 section of ultrasonic transducers.

At procedure 3320, selection of the ultrasonic transducers activated during the receive operation is controlled according to the receive pattern. In one embodiment, as shown at procedure 3322, selection signals are applied to columns and rows of the two-dimensional array according to control bits from the plurality of shift registers, where the ultrasonic transducers activated during the receive operation are at intersections of the columns and the rows specified by the selection signals.

At procedure 3330, a position of the receive pattern is shifted within the plurality of shift registers such that the ultrasonic transducers activated during the receive operation moves relative to and within the two-dimensional array of ultrasonic transducers.

In one embodiment, as shown at procedure 3340, a received signal from one or more selected ultrasonic transducers is directed to a selected receive channel during the receive operation. In one embodiment, as shown at procedure 3350, switches of the ultrasonic sensor are controlled responsive to the receive pattern overlapping at least two sub-arrays of the plurality of sub-arrays of ultrasonic transducers, where the received signals for all ultrasonic transducers of the receive pattern are directed to the selected receive channel during the receive operation.

In one embodiment, as shown at procedure 3352, the switches are controlled such that the received signals for all ultrasonic transducers of the receive pattern are directed to the selected receive channel of the sub-array including the center ultrasonic transducer of the receive pattern during the receive operation. In another embodiment, as shown at procedure 3354, the switches are controlled such that the received signals for all ultrasonic transducers of the receive pattern are directed to the selected receive channel of the sub-array including a representative ultrasonic transducer of the receive pattern during the receive operation. It should be appreciated that any ultrasonic transducer of the receive pattern may be selected as the representative ultrasonic transducer. In one embodiment, wherein the receive pattern is 2×2 ultrasonic transducers, the representative ultrasonic transducer is the upper left ultrasonic transducer of the receive pattern.

Figure 34:
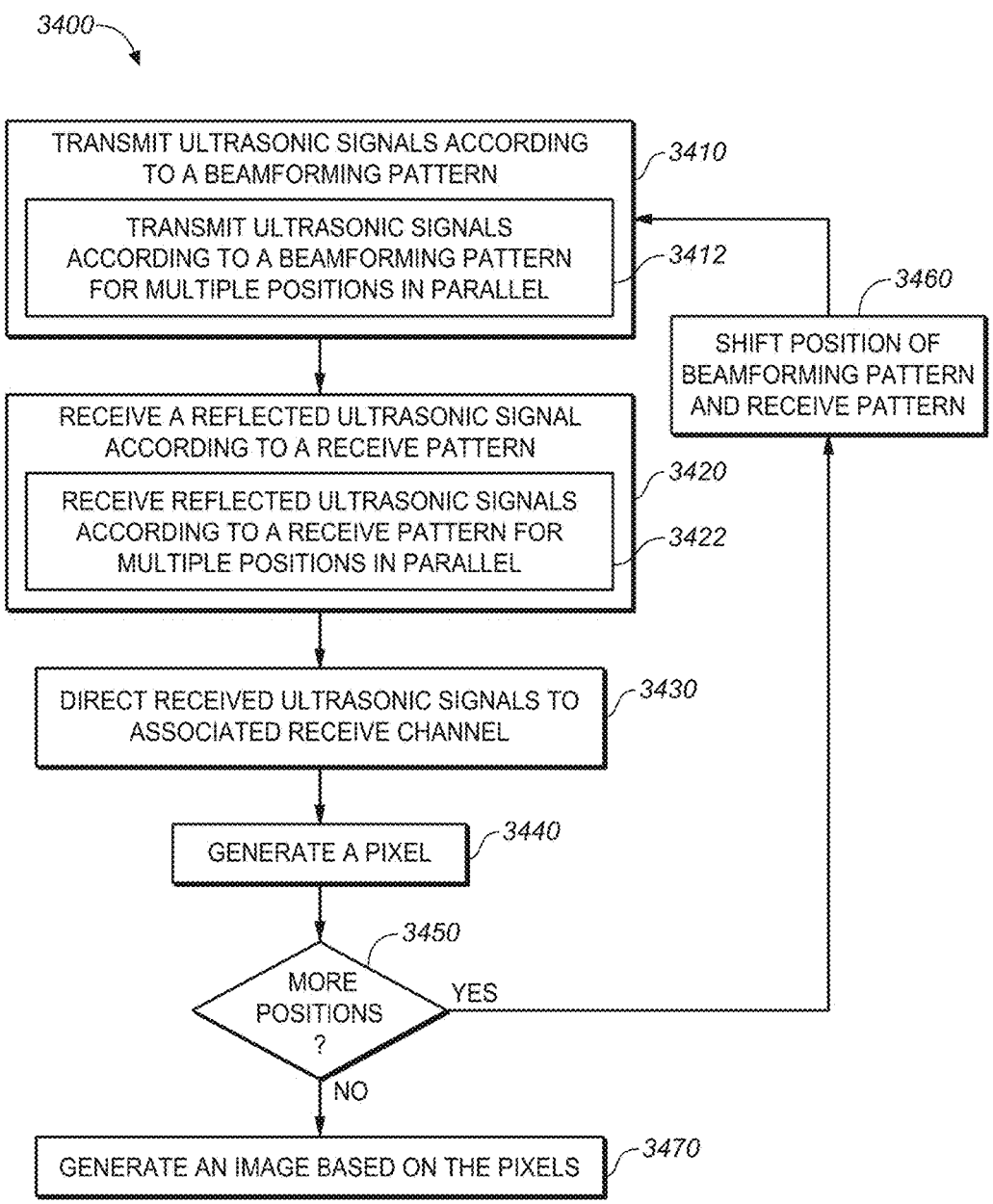
FIG. 34 illustrates a flow diagram of an example method for controlling an ultrasonic sensor during an imaging operation, according to various embodiments.

FIG. 34 illustrates a flow diagram of an example method for controlling an ultrasonic sensor during an imaging operation, according to various embodiments. At procedure 3410 of flow diagram 3400, a plurality of ultrasonic signals are transmitted according to a beamforming pattern at a position of a two-dimensional array of ultrasonic transducers. The beamforming pattern identifies ultrasonic transducers of the two-dimensional array of ultrasonic transducers that are activated during transmission of the ultrasonic signals that, when activated, focus the plurality of ultrasonic signals to a location above the two-dimensional array of ultrasonic transducers. At least some ultrasonic transducers of the beamforming pattern are phase delayed with respect to other ultrasonic transducers of the beamforming pattern. In one embodiment, as shown in procedure 3412, the transmitting of the plurality of ultrasonic signals is performed at multiple positions of the two-dimensional array (e.g., a subset of positions of the plurality of positions of the two-dimensional array) in parallel. For example, with reference to FIG. 23, beamforming patterns 2320a, 2320b, and 2320c, transmit ultrasonic signals in parallel. In one embodiment, the positions of the multiple of positions activated during the transmitting are separated by a plurality of inactive ultrasonic transducers.

At procedure 3420, at least one reflected ultrasonic signal is received according to a receive pattern, where the receive pattern identifies at least one ultrasonic transducers of the two-dimensional array of ultrasonic transducers that is activated during the receiving. In one embodiment, as shown in procedure 3422, the receiving of the plurality of ultrasonic signals is performed at multiple positions of the two-dimensional array (e.g., a subset of positions of the plurality of positions of the two-dimensional array) in parallel. For example, with reference to FIG. 23, receive patterns 2330a, 2330b, and 2330c, receive reflected ultrasonic signals in parallel. In one embodiment, the positions of the multiple of positions activated during the receiving are separated by a plurality of inactive ultrasonic transducers. In one embodiment, the ultrasonic transducers identified by the beamforming pattern are different than ultrasonic transducers identified by the receive pattern (e.g., an ultrasonic transducer is not used for both transmitting and receiving at a position). It should be appreciated that an ultrasonic transducer may be available to transmit ultrasonic signals and receive reflected ultrasonic signals for different positions. In other embodiments, the beamforming pattern and receive pattern may identify at least one ultrasonic transducer for transmitting ultrasonic signals and receiving reflected ultrasonic signals.

In one embodiment, as shown at procedure 3430, for each position, received ultrasonic signals are directed to a receive channel associated with the position. In one embodiment, as shown at procedure 3440, a pixel of an image is generated based on the at least one reflected ultrasonic signal.

At procedure 3450, it is determined whether there are more positions of the two-dimensional array of ultrasonic transducers left to perform the transmitting of ultrasonic signals and receiving of reflected ultrasonic signals. In one embodiment, if it is determined that there are more positions, flow diagram 3400 proceeds to procedure 3460, wherein the position of the beamforming patterns and receive pattern is shifted. In one embodiment, the beamforming pattern is stored in a first plurality of shift registers (e.g., select shift register 2620, phase select shift register 2622, and phase vector select shift register 2640) and the receive pattern is stored in a second plurality of shift registers (e.g., column select shift register 2630, column select shift register 2632, and row select shift register 2650). In one embodiment, the first plurality of shift registers includes a plurality of instances of the beamforming pattern. In one embodiment, the second plurality of shift registers includes a plurality of instances of the receive pattern. In one embodiment, shifting the position of the beamforming pattern includes shifting the beamforming pattern within the first plurality of shift registers and shifting the position of the receive pattern includes shifting the receive pattern within the second plurality of shift registers. Upon completion of procedure 3460, flow diagram 3400 proceeds to procedure 3410, where procedures 3410 and 3420 are repeated for another position or positions.

With reference to procedure 3450, in one embodiment, if it is determined that there are no more positions remaining to perform the transmitting of ultrasonic signals and receiving of reflected ultrasonic signals, flow diagram 3400 proceeds to procedure 3470. In one embodiment, at procedure 3470, an image is generated based on the pixels generated at each position.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. A method of using an ultrasonic sensor comprising a two-dimensional array of ultrasonic transducers, the method comprising:
at a position of the two-dimensional array of ultrasonic transducers, activating a plurality of ultrasonic transducers of the two-dimensional array of ultrasonic transducers for capturing a pixel of an image, the activating comprising:
transmitting a plurality of ultrasonic signals according to a beamforming pattern over a plurality of signal lines, wherein each ultrasonic transducer of the two-dimensional array of ultrasonic transducers is independently and selectively coupled to the plurality of signal lines, wherein the beamforming pattern focuses the plurality of ultrasonic signals to a location above the two-dimensional array of ultrasonic transducers, wherein the beamforming pattern identifies a signal line of the plurality of signal lines to drive each ultrasonic transducer identified by the beamforming pattern, and wherein at least some ultrasonic transducers of the beamforming pattern are phase delayed with respect to other ultrasonic transducers of the beamforming pattern; and
receiving at least one reflected ultrasonic signal according to a receive pattern at a receive input, wherein each ultrasonic transducer of the two-dimensional array of ultrasonic transducers is independently and selectively coupled to the receive input, wherein the receive pattern identifies at least one ultrasonic transducer of the two-dimensional array of ultrasonic transducers that is activated during the receiving; and
repeating the transmitting and the receiving at a plurality of positions of the two-dimensional array of ultrasonic transducers, wherein the plurality of positions are for capturing an image over the two-dimensional array of ultrasonic transducers.

2. The method of claim 1, wherein the repeating the transmitting and the receiving at the plurality of positions of the two-dimensional array of ultrasonic transducers comprises:
performing the transmitting and the receiving for a subset of positions of the plurality of positions in parallel.

3. The method of claim 2, wherein positions of the subset of positions are separated by a plurality of inactive ultrasonic transducers.

4. The method of claim 1, wherein the ultrasonic transducers identified by the beamforming pattern for the position are different than the at least one ultrasonic transducer identified by the receive pattern for the position.

5. The method of claim 1, further comprising:
for each position, directing received ultrasonic signals to a receive channel associated with the position.

6. The method of claim 1, further comprising:
storing control bits for applying the beamforming pattern to the two-dimensional array of ultrasonic transducers in a first plurality of shift registers; and
storing control bits for applying the receive pattern to the two-dimensional array of ultrasonic transducers in a second plurality of shift registers.

7. The method of claim 6, wherein the repeating the transmitting and the receiving at a plurality of positions of the two-dimensional array of ultrasonic transducers comprises:
shifting the beamforming pattern within the first plurality of shift registers; and
shifting the receive pattern within the second plurality of shift registers.

8. The method of claim 6, wherein the storing the beamforming pattern in a first plurality of shift registers comprises:
storing a plurality of instances of the control bits for applying the beamforming pattern to the two-dimensional array of ultrasonic transducers in the first plurality of shift registers.

9. The method of claim 6, wherein the storing the receive pattern in a second plurality of shift registers comprises:
storing a plurality of instances of the control bits for applying the receive pattern to the two-dimensional array of ultrasonic transducers in the second plurality of shift registers.

10. The method of claim 1, further comprising:
for each position, generating a pixel of an image based on the at least one reflected ultrasonic signal.

11. The method of claim 10, further comprising:
generating the image based on the pixel generated at each position.

12. An ultrasonic sensor comprising:
a transmit signal generator for generating a plurality of ultrasonic signals, wherein each ultrasonic signal of the plurality of ultrasonic signals has a different phase delay relative to other ultrasonic signals of the plurality of ultrasonic signals;

a plurality of signal lines, wherein a signal line of the plurality of signal lines is configured to transmit one ultrasonic signal of the plurality of ultrasonic signals;

a two-dimensional array of ultrasonic transducers, wherein each ultrasonic transducer of the two-dimensional array of ultrasonic transducers is independently and selectively coupled to the plurality of signal lines;

a first plurality of shift registers for storing control bits for applying a beamforming pattern of a beamforming space to the two-dimensional array of ultrasonic transducers, wherein the beamforming pattern identifies ultrasonic transducers of the two-dimensional array of ultrasonic transducers that are activated during a transmit operation for transmitting the plurality of ultrasonic signals by identifying a signal line of the plurality of signal lines to drive each ultrasonic transducer identified by the beamforming pattern, wherein the beamforming pattern focuses the plurality of ultrasonic signals to a location above the two-dimensional array of ultrasonic transducers, and wherein at least some ultrasonic transducers of the beamforming pattern are phase delayed with respect to other ultrasonic transducers of the beamforming pattern;

a second plurality of shift registers for storing control bits for applying a receive pattern of the beamforming space to the two-dimensional array of ultrasonic transducers, wherein the receive pattern identifies at least one ultrasonic transducer of the two-dimensional array of ultrasonic transducers that is activated during a receive operation for receiving at least one reflected ultrasonic signal; and an array controller configured to control activation of ultrasonic transducers during the transmit operation according to the beamforming pattern and during the receive operation according to the receive pattern, the array controller configured to shift a position of the beamforming pattern within the first plurality of shift registers and to shift a position of the receive pattern within the second plurality of shift registers, such that the beamforming pattern and the receive pattern moves within and relative to the two-dimensional array of ultrasonic transducers, the array controller configured to repeat the transmit operation and the receive operation at a plurality of positions of the two-dimensional array of ultrasonic transducers.

13. The ultrasonic sensor of claim 12, wherein the ultrasonic transducers are Piezoelectric Micromachined Ultrasonic Transducer (PMUT) devices.

14. The ultrasonic sensor of claim 13, wherein the PMUT devices comprise an interior support structure.

15. The ultrasonic sensor of claim 12, further comprising:
a signal generator configured to generate the plurality of ultrasonic signals, wherein each ultrasonic signal of the plurality of ultrasonic signals has a different phase delay relative to other ultrasonic signals of the plurality of ultrasonic signals.

16. The ultrasonic sensor of claim 12, wherein the first plurality of shift registers is configured to store a plurality of instances of the control bits for applying the beamforming pattern to the two-dimensional array of ultrasonic transducers corresponding to a subset of positions of the plurality of positions of the two-dimensional array of ultrasonic transducers, such that the transmit operation is performed at each position of the subset of positions in parallel.

17. The ultrasonic sensor of claim 16, wherein the second plurality of shift registers is configured to store a plurality of instances of the control bits for applying the receive pattern to the two-dimensional array of ultrasonic transducers corresponding to the subset of positions of the plurality of positions of the two-dimensional array of ultrasonic transducers, such that the receive operation is performed at each position of the subset of positions in parallel.

18. The ultrasonic sensor of claim 12, further comprising:
a plurality of receive channel inputs, where each receive channel input of the plurality of receive channel inputs is associated with a sub-array of ultrasonic transducers of the two-dimensional array of ultrasonic transducers.

19. The ultrasonic sensor of claim 18, further comprising:
switches at boundary regions between adjacent sub-arrays, wherein the switches are controlled to direct a received signal for an ultrasonic transducer to a receive channel of an associated sub-array of ultrasonic transducers during the receive operation.

20. A non-transitory computer-readable storage medium comprising instructions which when executed on one or more data processors, cause the one or more data processors to perform a method of using an ultrasonic sensor comprising a two-dimensional array of ultrasonic transducers, the method comprising:
defining an activation sequence of a plurality of positions, wherein the activation sequence defines movement of the plurality of positions over the two-dimensional array of ultrasonic transducers for forming a focused ultrasonic beam at different locations over the two-dimensional array of ultrasonic transducers, the focused ultrasonic beam for capturing a pixel of an image;
for each array position of the plurality of positions of the two-dimensional array of ultrasonic transducers:
transmitting a plurality of ultrasonic signals according to a beamforming pattern over a plurality of signal lines, wherein each ultrasonic transducer of the two-dimensional array of ultrasonic transducers is independently and selectively coupled to the plurality of signal lines, wherein the beamforming pattern focuses the plurality of ultrasonic signals to a location above the two-dimensional array of ultrasonic transducers, wherein the beamforming pattern identifies a signal line of the plurality of signal lines to drive each ultrasonic transducer identified by the beamforming pattern, and wherein at least some ultrasonic transducers of the beamforming pattern are phase delayed with respect to other ultrasonic transducers of the beamforming pattern; and
receiving at least one reflected ultrasonic signal according to a receive pattern at a receive input, wherein each ultrasonic transducer of the two-dimensional array of ultrasonic transducers is independently and selectively coupled to the receive input, wherein the receive pattern identifies at least one ultrasonic transducer of the two-dimensional array of ultrasonic transducers that is activated during the receiving; and
repeating the transmitting and the receiving at the plurality of positions of the two-dimensional array of ultrasonic transducers, wherein the transmitting and the receiving for a subset of positions of the plurality of positions are performed simultaneously.

* * * * *